US009550987B2

(12) United States Patent
Green et al.

(10) Patent No.: US 9,550,987 B2
(45) Date of Patent: Jan. 24, 2017

(54) RIBOREGULATOR COMPOSITIONS AND METHODS OF USE

(71) Applicants: President and Fellows of Harvard College, Cambridge, MA (US); Trustees of Boston University, Boston, MA (US)

(72) Inventors: Alexander A. Green, Scottsdale, AZ (US); Peng Yin, Brookline, MA (US); James J. Collins, Boston, MA (US)

(73) Assignees: President and Fellows of Harvard College, Cambridge, MA (US); Trustees of Boston University, Boston, MA (US)

(*) Notice: Subject to any disclaimer, the term of this patent is extended or adjusted under 35 U.S.C. 154(b) by 0 days.

(21) Appl. No.: 14/440,917

(22) PCT Filed: Nov. 6, 2013

(86) PCT No.: PCT/US2013/068818
§ 371 (c)(1),
(2) Date: May 6, 2015

(87) PCT Pub. No.: WO2014/074648
PCT Pub. Date: May 15, 2014

(65) Prior Publication Data
US 2015/0275203 A1    Oct. 1, 2015

Related U.S. Application Data

(60) Provisional application No. 61/722,825, filed on Nov. 6, 2012, provisional application No. 61/843,934, filed on Jul. 9, 2013.

(51) Int. Cl.
| | |
|---|---|
| *C07H 21/02* | (2006.01) |
| *C07H 21/04* | (2006.01) |
| *C12N 15/85* | (2006.01) |
| *C12N 15/11* | (2006.01) |
| *C12N 15/113* | (2010.01) |
| *C12N 15/115* | (2010.01) |
| *C12N 15/67* | (2006.01) |
| *C12Q 1/68* | (2006.01) |

(52) U.S. Cl.
CPC ............ *C12N 15/11* (2013.01); *C12N 15/113* (2013.01); *C12N 15/115* (2013.01); *C12N 15/67* (2013.01); *C12Q 1/6897* (2013.01); *C12N 2310/17* (2013.01); *C12Q 1/6816* (2013.01)

(58) Field of Classification Search
CPC .................. C12N 15/113; C12N 2310/11
See application file for complete search history.

(56) References Cited

FOREIGN PATENT DOCUMENTS

| EP | 2 221 371 A1 | 8/2010 |
|---|---|---|
| WO | WO 2004/046321 A2 | 6/2004 |
| WO | WO 2014/074648 A2 | 5/2014 |

OTHER PUBLICATIONS

Barrick et al., Quantitative analysis of ribosome binding sites in E.coli. Nucleic Acids Res. Apr. 11, 1994;22(7):1287-95.
Callura et al., Genetic switchboard for synthetic biology applications. Proc Natl Acad Sci U S A. Apr. 10, 2012;109(15):5850-5.
Culler et al., Reprogramming cellular behavior with RNA controllers responsive to endogenous proteins. Science. Nov. 26, 2010;330(6008):1251-5. doi: 10.1126/science.1192128.
Khalil et al., A synthetic biology framework for programming eukaryotic transcription functions. Cell. Aug. 3, 2012;150(3):647-58.
Qian et al., Scaling up digital circuit computation with DNA strand displacement cascades. Science. Jun. 3, 2011;332(6034):1196-201.
Takahashi et al., A modular strategy for engineering orthogonal chimeric RNA transcription regulators. Nucleic Acids Res. Aug. 2013;41(15):7577-88.
Vimberg et al., Translation initiation region sequence preferences in Escherichia coli. BMC Mol Biol. Oct. 31, 2007;8:100.
International Search Report and Written Opinion for PCT/US2013/068818 mailed Jul. 8, 2014.
International Preliminary Report on Patentability for PCT/US2013/068818 mailed May 21, 2015.
Isaacs et al., Engineered riboregulators enable post-transcriptional control of gene expression. Nat Biotechnol. Jul. 2004;22(7):841-7. Epub Jun. 20, 2004.
Lucks et al., Versatile RNA-sensing transcriptional regulators for engineering genetic networks. Proc Natl Acad Sci U S A. May 24, 2011;108(21):8617-22. doi: 10.1073/pnas.1015741108. Epub May 9, 2011.
Mutalik et al., Rationally designed families of orthogonal RNA regulators of translation. Nat Chem Biol. Mar. 25, 2012;8(5):447-54. doi: 10.1038/nchembio.919.
Rodrigo et al., De novo automated design of small RNA circuits for engineering synthetic riboregulation in living cells. Proc Natl Acad Sci U S A. Sep. 18, 2012;109(38):15271-6. Epub Sep. 4, 2012.
PCT/US2013/068818, Jul. 8, 2014, International Search Report and Written Opinion.
PCT/US2013/068818, May 21, 2015, International Preliminary Report on Patentability.

(Continued)

Primary Examiner — Amy Bowman
(74) Attorney, Agent, or Firm — Wolf, Greenfield & Sacks, P.C.

(57) ABSTRACT

The invention provides novel and versatile classes of riboregulators, including inter alia activating and repressing riboregulators, switches, and trigger and sink RNA, and methods of their use for detecting RNAs in a sample such as a well and in modulating protein synthesis and expression.

35 Claims, 32 Drawing Sheets

(56) References Cited

OTHER PUBLICATIONS

Ausländer et al., Programmable single-cell mammalian biocomputers. Nature. Jul. 5, 2012;487(7405):123-7. doi: 10.1038/nature11149. Abstract only.

Babendure et al., Control of mammalian translation by mRNA structure near caps. RNA. May 2006;12(5):851-61. Epub Mar. 15, 2006.

Bashor et al., Using engineered scaffold interactions to reshape MAP kinase pathway signaling dynamics. Science. Mar. 14, 2008;319(5869):1539-43. doi: 10.1126/science.1151153. Abstract only.

Bonnet et al., Amplifying genetic logic gates. Science. May 3, 2013;340(6132):599-603. doi: 10.1126/science.1232758. Epub Mar. 28, 2013. Abstract only.

Cameron et al., A brief history of synthetic biology. Nat Rev Microbiol. May 2014;12(5):381-90. doi: 10.1038/nrmicro3239. Epub Apr. 1, 2014. Abstract only.

Canton et al., Refinement and standardization of synthetic biological parts and devices. Nat Biotechnol. Jul. 2008;26(7):787-93. doi: 10.1038/nbt1413. Abstract only.

Daniel et al., Synthetic analog computation in living cells. Nature. May 30, 2013;497(7451):619-23. doi: 10.1038/nature12148. Epub May 15, 2013. Abstract only.

Danino et al., A synchronized quorum of genetic clocks. Nature. Jan. 21, 2010;463(7279):326-30. doi: 10.1038/nature08753.

Delebecque et al., Organization of intracellular reactions with rationally designed RNA assemblies. Science. Jul. 22, 2011;333(6041):470-4. doi: 10.1126/science.1206938. Epub Jun. 23, 2011. Abstract only.

Elowitz et al., A synthetic oscillatory network of transcriptional regulators. Nature. Jan. 20, 2000;403(6767):335-8. Abstract only.

Gardner et al., Construction of a genetic toggle switch in *Escherichia coli*. Nature. Jan. 20, 2000;403(6767):339-42. Abstract only.

Grabow et al., RNA modularity for synthetic biology. F1000Prime Rep. Nov. 1, 2013;5:46. doi: 10.12703/P5-46. eCollection 2013.

Green et al., Toehold switches: de-novo-designed regulators of gene expression. Cell. Nov. 6, 2014;159(4):925-39. doi: 10.1016/j.cell.2014.10.002. Epub Oct. 23, 2014.

Liu et al., An adaptor from translational to transcriptional control enables predictable assembly of complex regulation. Nat Methods. Nov. 2012;9(11):1088-94. doi: 10.1038/nmeth.2184. Epub Sep. 30, 2012. Abstract only.

Matthews et al., Expanded sequence dependence of thermodynamic parameters improves prediction of RNA secondary structure. J Mol Biol. May 21, 1999;288(5):911-40. Abstract only.

Rinaudo et al., A universal RNAi-based logic evaluator that operates in mammalian cells. Nat Biotechnol. Jul. 2007;25(7):795-801. Epub May 21, 2007.

Ruder et al., Synthetic biology moving into the clinic. Science. Sep. 2, 2011;333(6047):1248-52. doi: 10.1126/science.1206843. Abstract only.

Tamsir et al., Robust multicellular computing using genetically encoded Nor gates and chemical 'wires'.Nature. Jan. 13, 2011;469(7329):212-5. doi: 10.1038/nature09565. Epub Dec. 8, 2010.

Win et al., Higher-order cellular information processing with synthetic RNA devices. Science. Oct. 17, 2008;322(5900):456-60. doi: 10.1126/science.1160311.

Xie et al., Multi-input RNAi-based logic circuit for identification of specific cancer cells. Science. Sep. 2, 2011;333(6047):1307-11. doi: 10.1126/science.1205527. Abstract only.

Zadeh et al., Nupack: Analysis and design of nucleic acid systems. J Comput Chem. Jan. 15, 2011;32(1):170-3. doi: 10.1002/jcc.21596. Abstract only.

Zadeh et al., Nucleic acid sequence design via efficient ensemble defect optimization. J Comput Chem. Feb. 2011;32(3):439-52. doi: 10.1002/jcc.21633. Epub Aug. 17, 2010. Abstract only.

Zhang et al., Control of DNA strand displacement kinetics using toehold exchange. J Am Chem Soc. Dec. 2, 2009;131(47):17303-14. doi: 10.1021/ja906987s. Abstract only.

Zhang et al., Dynamic DNA nanotechnology using strand-displacement reactions. Nature Chemistry 3, 103-113 (2011) doi:10.1038/nchem.957. Abstract only.

Zhang et el., Function of hexameric RNA in packaging of bacteriophage phi 29 DNA in vitro. Mol Cell. Jul. 1998;2(1):141-7.

taRNA Input A taRNA Input B crRNA OR Gate C

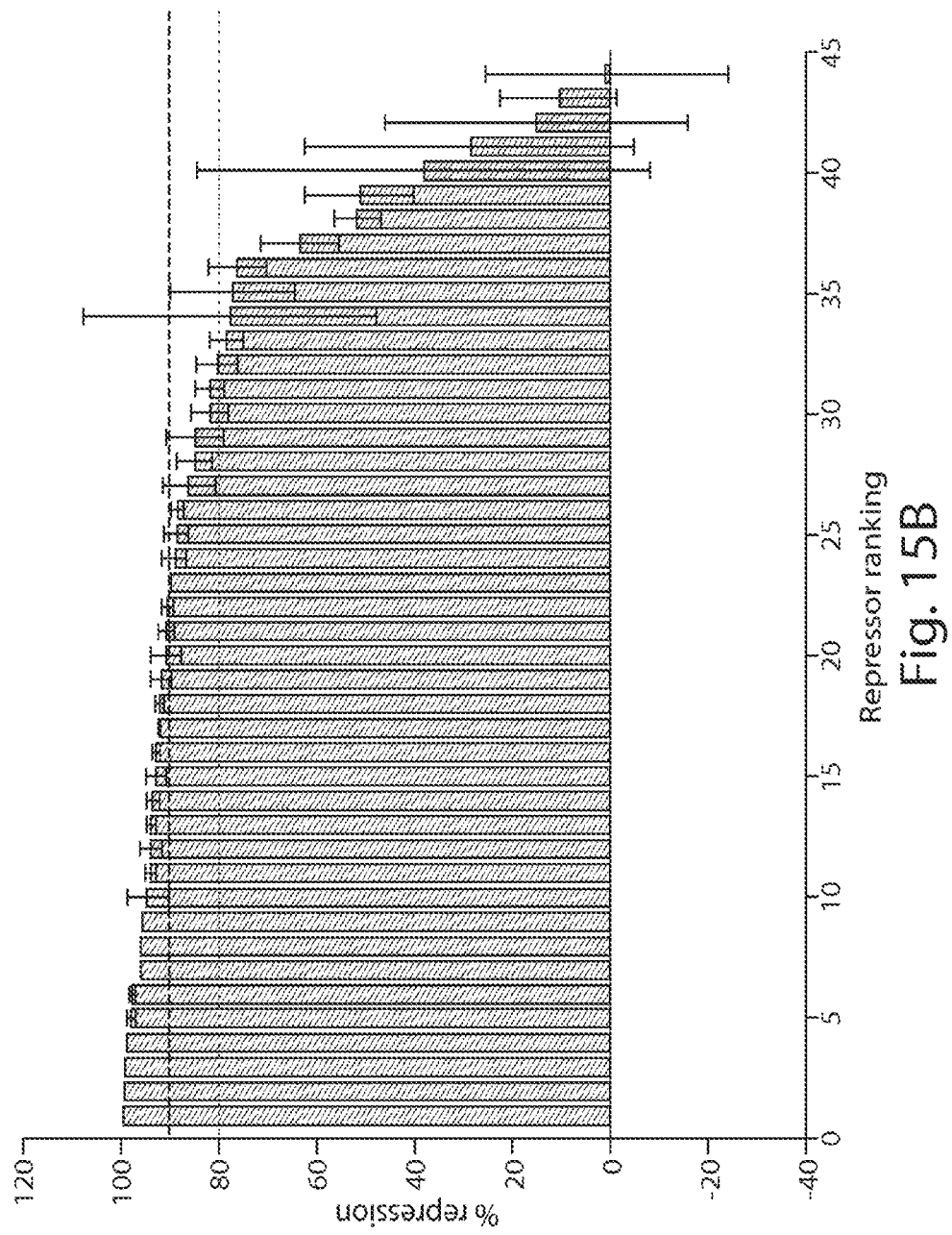

RIBOREGULATOR COMPOSITIONS AND METHODS OF USE

RELATED APPLICATIONS

This application is a national stage filing under 35 U.S.C. §371 of international application number PCT/US2013/068818, filed Nov. 6, 2013, which was published under PCT Article 21(2) in English and claims the benefit of U.S. Provisional Application No. 61/722,825, filed Nov. 6, 2012, and U.S. Provisional Application No. 61/843,934, filed Jul. 9, 2013, each of which is incorporated by reference herein in its entirety.

FEDERALLY SPONSORED RESEARCH

This invention was made with U.S. Government support under grant number 635-67116-XXXX-167832-435548-0002.66625 awarded by DARPA and grant number 1DP2OD007292 awarded by the National Institutes of Health. The Government has certain rights in the invention.

BACKGROUND OF INVENTION

Riboregulators are sequences of RNA that effect changes in cells in response to a nucleic acid sequence. These RNA-based devices, which typically regulate protein translation or trigger mRNA degradation, have been used for a number of applications in synthetic biology, including sensitive control over gene expression, shunting of metabolic flux through different metabolic pathways, and synthetic control over cell death.

In riboregulators that control gene expression, repression of protein translation has relied on sequestration of the normally single-stranded ribosome binding site (RBS) within a duplex RNA region that is upstream of a gene of interest (GOI). An mRNA in which the RBS is sequestered within a hairpin upstream of the GOI is thus a cis-repressed RNA (crRNA). A riboregulator based on an engineered crRNA can be constructed in which a trans-activating RNA (taRNA) binds to the crRNA and unwinds the repressing RNA duplex thereby exposing a now single-stranded RBS and activating translation of the downstream gene. In riboregulators that decrease expression of the GOI, the RBS and initiation codon of the GOI are both exposed in the absence of the trigger RNA. However, a trans-repressing RNA (trRNA), which bears anti-sense to the RBS and start codon, can bind to the riboregulator and strongly suppress translation of the downstream gene.

Over the past decade, researchers have developed a number of different riboregulator systems to control gene expression in prokaryotic cells. These previous systems have utilized a number of recurring design motifs. The vast majority of riboregulators have employed loop-linear interactions to drive the crRNA/trans-RNA hybridization reaction forward. In these interactions, a linear, single-stranded region in one of the strands binds to a loop established at the end of a duplex in the other strand. Essential in this interaction is the formation of a kissing loop structure in which the tertiary structure of the RNA sequence causes bases within the loop to flip outwards, facilitating binding with the linear RNA strand. Importantly, this kissing loop structure is only established with specific sequences inside the loop region, which can severely limit the number of possible crRNA designs.

All previous riboregulator systems have relied on sequestration of the RBS to impede translation of the GOI. This design choice has two crucial implications. First, much of the work in optimization of genetic circuits in synthetic biology relies on varying the strength of the RBS to finely tune protein levels inside the cell. Since the RBS sequence is a functional part of these riboregulators, one cannot simply replace the riboregulator RBS with variants and expect the output characteristics of the device to vary in a predictable manner following the strength of the new RBS. Furthermore, changes to the RBS will require corresponding modifications in the sequence of the trans-RNA. Second, for riboregulators that activate gene expression, riboregulators that sequester the RBS must be activated by taRNA sequences that are at least partially complementary to the crRNA RBS sequence. Consequently, unbound taRNAs can compete with de-repressed crRNA species for ribosome binding. Alternatively, RBS sequences within the taRNAs can also be sequestered within stem regions. This additional secondary structure can decrease the kinetics of binding with the crRNA and the dynamic range of the riboregulator.

SUMMARY OF INVENTION

The invention provides, in part, programmable riboregulators that can be activated by RNAs, including RNAs endogenous, to a cell or sample of interest. Such programmable riboregulators have not been possible previously due in part to the severe constraints, including sequence constraints, outlined herein. The novel riboregulators of the invention provide sufficient freedom in the sequence of the taRNA (trigger RNA) (and corresponding region of crRNA (e.g., switch RNA) to which the taRNA hybridizes) to allow for activation by, for example, RNAs such as but not limited to endogenous RNAs. When coupled to protein reporters such as fluorescent reporters, such riboregulators would act as sensors to probe RNA levels in real time in living cells or other types of RNA-containing samples. The invention can be used to detect and quantitate endogenous RNA in real time without having to harvest the RNA from the cell (or sample). The method is sufficiently sensitive to detect RNA present at physiological copy numbers.

The riboregulators of the invention are less constrained in sequence than are those of the prior art, and accordingly a variety of riboregulators may be generated and importantly used together in a single system such as a cell. Such orthogonality has not been possible heretofore using the riboregulators of the prior art. The riboregulators of the invention also do not depend upon the RBS for their structure. As a result, it is possible to modify the RBS without affecting the function of the riboregulator. The programmable nature of the riboregulators of the invention allow "plug and play" implementations of higher order cellular logic.

The invention therefore provides methods for detecting (sensing) and measuring levels of one or more endogenous RNA, effecting sensitive control over one or more proteins simultaneously in a cell or sample (including translational control), performing complex logic operations in a cell or a sample, programming in a cell or sample, detecting single-nucleotide polymorphisms (SNPs) in living systems, and detecting RNAs and SNP RNAs in in vitro translation systems, using the riboregulator (including the toehold switch RNA and/or the toehold repressors) and/or the taRNA (trigger RNA) and/or the sink RNA compositions of the invention.

The cis-repressing RNA (crRNA) and trans-activating RNA (taRNA) of the invention may be comprised of RNA in whole or in part. They may comprise naturally occurring nucleotides and/or non-naturally occurring nucleotides. The crRNA may also be referred to herein as switch RNA. A crRNA intends an RNA that is typically repressed until bound to a taRNA (or trigger RNA), as such binding results in translation of a protein of interest from the crRNA/switch RNA. Binding of the trigger RNA to the crRNA/switch typically occurs via a toehold domain, in some instances, and as described in greater detail herein.

The invention contemplates crRNA that may be modularly used via operable linkage to a coding domain. The invention further contemplates taRNA that may be modularly used to de-repress or activate crRNA.

Thus, in one aspect, the invention provides a toehold crRNA (toehold switch) riboregulator comprising a single-stranded toehold domain, a fully or partially double-stranded stem domain comprising an initiation codon, and a loop domain comprising a ribosome binding site. The toehold crRNA/toehold switch may comprise an RBS sequence located in the loop domain.

In another aspect, the invention provides an RNA comprising more than one crRNA, optionally operably linked to a coding domain (as described below), wherein the multiple crRNA may be activated by the same or by different taRNA (trigger RNA). In some embodiments, a single taRNA may activate expression of a downstream coding sequence. In such embodiments, the toehold crRNA riboregulator may be used to detect expression of a plurality of taRNA using a single readout.

In another aspect, the invention provides a toehold riboregulator system comprising (1) a crRNA riboregulator comprising a single-stranded toehold domain, a fully or partially double-stranded stem domain comprising an initiation codon, and a loop domain comprising a ribosome binding site, and (2) a coding domain. In some embodiments, taRNAs that hybridize to complementary regions in the stem domain activate expression of a downstream coding sequence. In some embodiments, 2, 3, 4, 5, 6, or more or all of the taRNAs are required in order to activate expression of the downstream coding sequence. The terms system and device are used interchangeably herein to refer to a collection of riboregulator components including but not limited to and in any combination crRNA (switch RNA), taRNA (trigger RNA), sink RNA, and the like.

In some embodiments, the riboregulator further comprises a spacer domain. In some embodiments, the spacer domain encodes low molecular weight amino acids. In some embodiments, the spacer domain is about 9-33 nucleotides in length. In some embodiments, the spacer domain is about 21 nucleotides in length. In some embodiments, the spacer domain is situated between the stem domain and the coding domain. In some embodiments, the spacer domain is greater than 33 nucleotides in length and can contain single- and double-stranded regions, including other riboregulators.

In some embodiments, the stem domain comprises sequence upstream (5') and/or downstream (3') of the initiation codon. In some embodiments, the sequence upstream of the initiation codon is about 6 nucleotides. In some embodiments, the sequence downstream of the initiation codon is about 9 nucleotides. In some embodiments, the sequence downstream of the initiation codon does not encode a stop codon.

In some embodiments, the coding domain encodes a reporter protein. In some embodiments, the reporter protein is green fluorescent protein (GFP). In some embodiments, the coding domain encodes a non-reporter protein. As used herein, a non-reporter protein is any protein that is used or that functions in a manner in addition to or instead of as a reporter protein. A non-reporter protein may interact with another entity in the cell or sample, and may thereby effect a change in the cell or sample or in another moiety.

In some embodiments, the toehold domain is complementary in sequence to a naturally occurring RNA. A naturally occurring RNA may be an RNA that is capable of being expressed from the cell of interest (e.g., from an endogenous gene locus). In some embodiments, the toehold domain is complementary in sequence to a non-naturally occurring RNA. A non-naturally occurring RNA may be an RNA that is not naturally expressed in a cell of interest (e.g., it is not expressed from an endogenous gene locus), and may instead be expressed from an exogenous nucleic acid introduced into the cell of interest.

In another aspect, the invention provides a trans-activating RNA (taRNA) comprising a first domain that hybridizes to a toehold domain of any of the foregoing riboregulators and that comprises no or minimal secondary structure, and a second domain that hybridizes to a sequence downstream (3') of the toehold domain. In some embodiments, the first domain is 100% complementary to the toehold domain. In some embodiments, the second domain may be less than 100% complementary to the sequence downstream of the toehold domain.

The taRNA may consist of more than one strand of RNA, and such multiple RNAs in combination provide the first and second domain for hybridization with the crRNA. In some embodiments, one or more RNAs may be used to bring multiple taRNAs into close proximity via hybridization to enable them to efficiently hybridize with the riboregulator. Examples of such embodiments are illustrated in FIGS. 9 and 10.

In another aspect, the invention provides a system comprising one or more of any of the foregoing crRNA riboregulators, and/or one or more of any of the foregoing trans-activating RNA (taRNA). The taRNA may all be naturally occurring RNA, or they may all be non-naturally occurring RNA, or they may be a mixture of naturally occurring RNA and non-naturally occurring RNA.

The systems of the invention may include a plurality of riboregulators (e.g., a plurality of crRNA/switches, optionally together with cognate taRNA/trigger RNA) having minimal cross-talk amongst themselves. In some embodiments, the systems may comprise at least 2, 3, 4, 5, 6, 7, 8, 9, 10, 11, 12, 13, 14, 15, 16, 17, 18, 19, 20 or more toehold crRNA/switches, having minimal cross-talk (e.g., on the level of less than 20%, 19%, 18%, 17%, 16%, 15%, 14%, 13%, 12%, 11%, 10%, 9%, 8%, 7%, 6%, 5%, 4%, 3%, 2% or less). In some embodiments, the toehold crRNA/switches have an average ON/OFF fluorescence ratio of more than 50, 100, 150, 200, 250, 300, 350, 400, or more. In some instances, the invention provides systems having a plurality of toehold crRNA/switches having an average ON/OFF fluorescence ratio in the range of about 200-665, including about 400. In some embodiments, the level of cross-talk amongst a plurality of toehold riboregulators in a system ranges from about 2% to less than 20%, or from about 2% to about 15%, or from about 5% to about 15%. Such systems may comprise 7 or more, including 8, 9, 10, etc. toehold riboregulators.

In some embodiments, the system is a cell. In some embodiments, the cell is a prokaryotic cell.

In some embodiments, the system is a cell-free in vitro system.

In some embodiments, the crRNA riboregulator and the taRNA are hybridized to each other.

In some embodiments, the ratio of crRNA riboregulator to taRNA is less than 1, less than 0.5, or less than 0.1.

In some embodiments, the crRNA riboregulator or riboregulator system is comprised in a first nucleic acid and the taRNA is comprised in a second nucleic acid. In some embodiments, the first nucleic acid is a first plasmid and the second nucleic acid is a second plasmid. In some embodiments, the first plasmid comprises a medium copy origin of replication and the second plasmid comprises a high copy origin of replication. The plasmids may be DNA plasmids or RNA plasmids.

In another aspect, the invention provides a nucleic acid comprising any of the foregoing crRNA riboregulators or riboregulator systems or comprising sequences that encode any of the foregoing crRNA riboregulators or riboregulator systems. In another aspect, the invention provides a host cell comprising any of the foregoing nucleic acids.

In another aspect, the invention provides a nucleic acid comprising any of the foregoing trans-activating RNA (taRNA) or comprising sequences that encode any of the foregoing taRNA. In another aspect, the invention provides a host cell comprising the nucleic acid.

In another aspect, the invention provides a method of detecting presence of an RNA in a sample, comprising combining any of the foregoing toehold crRNA riboregulator systems with a sample, wherein the crRNA riboregulator comprises a toehold domain that is complementary to an endogenous RNA, and wherein the riboregulator system comprises a coding domain that encodes a reporter protein, under conditions that allow translation of the coding domain in the presence of the endogenous RNA but not in the absence of the endogenous RNA, and detecting the reporter protein as an indicator of the endogenous RNA. As used herein, conditions that allow translation of the coding domain are conditions that include all the necessary machinery to produce a protein from an RNA such as but not limited to ribosomes, tRNAs, and the like.

In another aspect, the invention provides a method of detecting presence of an RNA in a cell, comprising introducing into the cell any of the foregoing toehold riboregulator systems, wherein the crRNA riboregulator comprises a toehold domain that is complementary to an endogenous RNA in the cell, and wherein the riboregulator system comprises a coding domain that encodes a reporter protein, and detecting the reporter protein as an indicator of the endogenous RNA. In some embodiments, the reporter protein is green fluorescent protein (GFP). In some embodiments, amount of reporter protein is an indicator of amount of endogenous RNA.

In another aspect, the invention provides a method of controlling protein translation, comprising combining any of the foregoing toehold riboregulator systems with any of the foregoing complementary taRNA, wherein the toehold crRNA riboregulator comprises a toehold domain that is complementary to the taRNA, and wherein the toehold riboregulator system comprises a coding domain that encodes a non-reporter protein, under conditions that allow translation of the coding domain in the presence of the taRNA but not in the absence of the taRNA.

In another aspect, the invention provides a beacon riboregulator system comprising (1) a beacon crRNA riboregulator comprising a fully or partially double-stranded stem domain comprising a ribosome binding site, and a loop domain, (2) a coding domain, and (3) an initiation codon present between the stem domain and the coding domain.

In some embodiments, the stem domain comprises sequence upstream (5') of the initiation codon. In some embodiments, the sequence upstream of the initiation codon is about 6 nucleotides.

In some embodiments, the coding domain encodes a reporter protein. In some embodiments, the reporter protein is green fluorescent protein (GFP). In some embodiments, the coding domain encodes a non-reporter protein.

In some embodiments, the loop domain is complementary in sequence to a naturally occurring RNA. In some embodiments, the loop domain is complementary in sequence to a non-naturally occurring RNA. In some embodiments, the loop domain is about 21 nucleotides in length. In some embodiments, the loop domain ranges in length from about 15-30 nucleotides.

In some embodiments, the beacon crRNA riboregulator comprises a binding domain (i.e., a domain that hybridizes to its complementary taRNA) that includes but is not limited to the loop domain. The binding domain may comprise a region upstream (5') of the loop domain that may be about 9 nucleotides in length and which may exist in the stem domain.

The stem domain may be about 23 bps in length. The stem domain may range from about 15 bp to about 30 bps.

In another aspect, the invention provides a trans-activating RNA (taRNA) comprising a first domain that hybridizes to a loop domain of any of the foregoing beacon riboregulators and that comprises no or minimal secondary structure, and a second domain that hybridizes to a sequence upstream (5') of the loop domain and present in the stem domain. In some embodiments, the first domain is 100% complementary to the loop domain.

In another aspect, the invention provides a system comprising one or more of any of the foregoing beacon crRNA riboregulators, optionally operably linked to a coding domain, and any of the foregoing complementary trans-activating RNA (taRNA).

In some embodiments, the system is a cell. In some embodiments, the cell is a prokaryotic cell. In some embodiments, the system is a cell-free in vitro system.

In some embodiments, the beacon crRNA riboregulator and the taRNA are hybridized to each other.

In some embodiments, the ratio of beacon crRNA riboregulator to taRNA is less than 1, less than 0.5, or less than 0.1.

In some embodiments, the beacon crRNA riboregulator (or system) is comprised in a first nucleic acid and the taRNA is comprised in a second nucleic acid. In some embodiments, the first nucleic acid is a first plasmid and the second nucleic acid is a second plasmid. In some embodiments, the first plasmid comprises a medium copy origin of replication and the second plasmid comprises a high copy origin of replication. The plasmids may be DNA plasmids or RNA plasmids.

In another aspect, the invention provides a nucleic acid comprising any of the foregoing beacon crRNA riboregulators (or systems) or sequences that encode any of the foregoing beacon crRNA riboregulators (or systems). In another aspect, the invention provides a host cell comprising said nucleic acid.

In another aspect, the invention provides a nucleic acid comprising any of the foregoing trans-activating RNA (taRNA) or sequences that encode any of the foregoing taRNA. In another aspect, the invention provides a host cell comprising said nucleic acid.

In another aspect, the invention provides a method of detecting presence of an RNA in a sample, comprising combining a beacon riboregulator system with a sample, wherein the beacon crRNA riboregulator comprises a loop domain that is complementary to an endogenous RNA, and wherein the beacon riboregulator system comprises a coding domain that encodes a reporter protein, under conditions that allow translation of the coding domain in the presence of the endogenous RNA but not in the absence of the endogenous RNA, and detecting the reporter protein as an indicator of the endogenous RNA.

In another aspect, the invention provides a method of detecting presence of an RNA in a cell, comprising introducing into the cell a beacon riboregulator system, wherein the beacon crRNA riboregulator comprises a loop domain that is complementary to an endogenous RNA in the cell, and wherein the beacon riboregulator system comprises a coding domain that encodes a reporter protein, and detecting the reporter protein as an indicator of the endogenous RNA.

In some embodiments, the reporter protein is green fluorescent protein (GFP).

In some embodiments, amount of reporter protein is an indicator of amount of endogenous RNA.

In another aspect, the invention provides a method of controlling protein translation, comprising combining a beacon riboregulator system with a complementary taRNA, wherein the beacon crRNA riboregulator comprises a loop domain that is complementary to the taRNA, and wherein the beacon riboregulator system comprises a coding domain that encodes a non-reporter protein, under conditions that allow translation of the coding domain in the presence of the taRNA but not in the absence of the taRNA.

These and other aspects and embodiments of the invention will be described in greater detail herein.

DETAILED DESCRIPTION OF INVENTION

Figure 1:
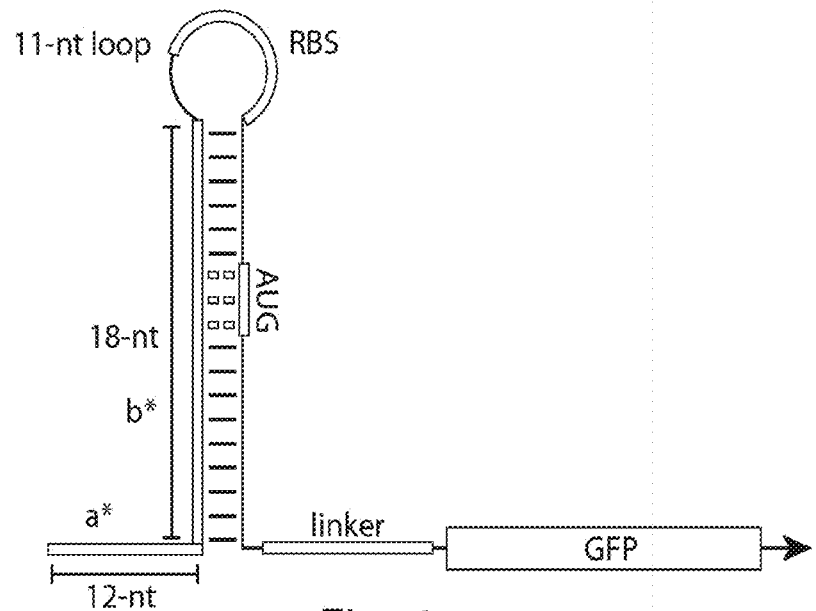
FIG. 1. Schematic of the toehold riboregulator crRNA base design. The corresponding taRNA has the sequence 5'-b-a-3' where domains a and b are the reverse complements of domains a* and b*, respectively.

The invention provides two general classes of riboregulators: toehold riboregulators and beacon riboregulators. Both can be used to activate protein production (or translation) in various systems including cells such as prokaryotic cells. Unlike previous engineered riboregulators of gene expression, these "devices" can be trans-activated using separate RNAs of virtually arbitrary sequence. The sequence of the activating RNA need not be related to a ribosome binding site (RBS) sequence.

The advantages of these new riboregulators are multifold. First, many riboregulators of the invention can be active in a single cell simultaneously, with each interacting only with its cognate (specific) targets. This allows simultaneous control over multiple cellular activities. Second, riboregulators of the invention can be incorporated into complex nucleic acid circuits in vivo with low system cross-talk and high programmability. Third, riboregulators of the invention can trigger protein (e.g., reporter protein) production from endogenous RNAs. When riboregulator output is coupled to a fluorescent protein reporter, these riboregulators act as genetically encodable sensors and imaging probes for endogenous RNAs in cells. For other proteins, such as those involved in cellular metabolism, activation of gene expression using these riboregulators can facilitate the interaction between pathways endogenous to the cell and synthetic gene networks for new applications in biotechnology.

The invention therefore provides a variety of novel riboregulators and "devices" derived therefrom that offer greatly improved diversity, orthogonality, and functionality compared to previously described riboregulators. In contrast to prior art riboregulators that inhibit translation solely by disrupting binding of the ribosome to the RBS, certain riboregulators of the invention allow ribosome docking (in some cases) but prevent translation initiation by blocking ribosome access to the initiation codon (in all cases) and usually extension from it. A benefit of this approach is that the RBS is no longer required to be part of the trans-RNA sequence enabling new riboregulators to be designed without any dependence on the Shine-Dalgarno sequence and with only few overall sequence constraints. In addition, these new riboregulators do not rely on kissing-loop interactions to drive hybridization between the crRNA and the trans-RNA. Instead, they utilize linear-linear (or large-loop-linear) RNA interactions, whose strength can be rationally controlled simply by changing the number of nucleotides driving the initial RNA-RNA interaction and/or by changing its base composition. In contrast, changes in base composition and/or sequence length in a kissing loop interaction can affect the tertiary structure of interacting domains and decrease the kinetics of the hybridization reaction.

Riboregulators Generally

Riboregulators are RNA molecules that can be used to repress or activate translation of an open reading frame and thus production of a protein. Repression is achieved through the presence of a regulatory nucleic acid element (the cis-repressive RNA or crRNA) within the 5' untranslated region (5' UTR) of an mRNA molecule. The nucleic acid element forms a hairpin structure comprising a stem domain and a loop domain through complementary base pairing. The hairpin structure blocks access to the mRNA transcript by the ribosome, thereby preventing translation. In some embodiments, including for example embodiments involving prokaryotic cells, the stem domain of the hairpin structure sequesters the ribosome binding site (RBS). In some embodiments, including for example embodiments involving eukaryotic cells, the stem domain of the hairpin structure is positioned upstream of the start (or initiation) codon, within the 5' UTR of an mRNA. RNA expressed and acting in trans (and thus referred to as trans-activating RNA, or taRNA) interacts with the crRNA and alters the hairpin structure. This alteration allows the ribosome to gain access to the region of the transcript upstream of the start codon, thereby releasing the RNA from its repressed state and facilitating protein translation from the transcript. The crRNA are typically engineered RNA molecules. The taRNA may be engineering molecules although in some instances, as described herein, they may be regions of endogenous, naturally occurring RNAs within a system such as a cell.

The invention generally provides nucleic acids, constructs, plasmids, host cells and methods for post-transcriptional regulation of protein expression using RNA molecules to modulate and thus control translation of an open reading frame.

It is to be understood that the invention contemplates modular crRNA encoding nucleic acids and modular taRNA encoding nucleic acids. Modular crRNA encoding nucleic acids as used herein refer to nucleic acid sequences that do not comprise an open reading frame (or coding domain for a gene of interest). Such modular crRNA may be toehold crRNA or beacon crRNA. Thus the invention contemplates riboregulators in their final form (e.g., comprising a coding domain for a gene of interest) or riboregulator components (e.g., a toehold crRNA or a beacon crRNA not operably linked to gene of interest).

The invention further provides oligonucleotides comprising a crRNA sequence and oligonucleotides comprising a taRNA sequence. In addition, the invention provides sets of two or more oligonucleotides. A first set of oligonucleotides includes two or more oligonucleotides whose sequences together comprise a crRNA sequence. The invention also provides a second set of oligonucleotides whose sequences together comprise a taRNA sequence. For ease of cloning, it may be preferable to employ two oligonucleotides each of which includes a single stem-forming portion, in different cloning steps, rather than a single oligonucleotide comprising two stem-forming portions, in order to avoid formation of a stem within the oligonucleotide, which may hinder cloning. The oligonucleotides may be provided in kits with any of the additional components mentioned herein. The oligonucleotides may include restriction sites at one or both ends.

Toehold Riboregulators

In a toehold riboregulator system, the interaction between the crRNA and the trans-RNA species is mediated through a single-stranded RNA domain that is located to the 5' end of the crRNA stem. This domain, which is referred to as the toehold domain, provides the trans-RNA with sufficient binding affinity to enable it to unwind the crRNA stem. The degree of complementarity between the trans-RNA and the toehold domain may vary. It some embodiments, it is at least 60%, at least 70%, at least 80%, at least 90%, at least 95%, or 100%. For optimal riboregulator kinetics, the trans-RNA should possess minimal secondary structure and full complementarity (i.e., 100%) to the toehold domain of the crRNA. As used herein, secondary structure refers to non-linear structures including for example hairpin structures, stem loop structures, and the like. Accordingly, it is preferable that the trans-RNA consists of a sequence with little to no probability of forming secondary structure under the conditions of its use. Those of ordinary skill in the art are able to determine such sequences either manually or through the use of computer programs available in the art.

Toehold riboregulator crRNAs do not sequester the RBS within their stem domain. Instead, RBS are confined to the loop domain formed by the repressing stem domain. This allows the region immediately before (upstream or 5') and after (downstream or 3') the initiation codon to be sequestered within the stem domain, thus frustrating translation initiation. The respective lengths of the crRNA toehold, stem, and loop domains can be changed to a large extent without affecting the performance of the toehold riboregulator as will be detailed below. In addition, the crRNA stem domain can retain its repression efficiency even if it contains a number of bulges or mispaired bases, which enables trans-RNAs that do not contain the start codon AUG sequence to trigger the riboregulator. In principle, the tolerance of bulges enables arbitrary taRNA sequences, including endogenous RNAs, to act as input RNAs into the toehold riboregulator, although other criteria such as high secondary structure can affect the response of the regulator.

An exemplary, non-limiting, class of toehold riboregulators has design parameters shown in FIG. 1. crRNAs of this class possess a toehold domain that is about 12-nucleotides (nts) long and a loop domain that is about 11-nts long and that contains, optionally at its 3' end, an RBS sequence AGAGGAGA Immediately adjacent to this loop domain is a stem domain comprising a 6-bp duplex spacer region and a 9-bp duplex region flanking a start codon (i.e., AUG). The 9-nts downstream (3') of the start codon were programmed to ensure they did not code for any stop codons since this would lead to early termination of translation. In addition, the 3-nt region opposite the start codon triad was completely unpaired leading to a crRNA stem domain having a 3-nt long bulge. To reduce the likelihood that the 9-nt duplex region code for amino acids that affect folding of the gene of interest (GOI), a common 21-nt (7-amino-acid) spacer domain containing a number of low molecular weight residues was inserted between the crRNA stem domain and the coding domain (e.g., the domain coding the GOI or the reporter protein.

It is to be understood that the embodiment illustrated in FIG. 1 is non-limiting and that other riboregulators of differing lengths and functions are contemplated and encompassed by the invention. Thus, the length of the toehold domain, the stem domain, the loop domain and the linker domain, as well as the duplex regions within the stem domain may differ in length from the embodiment shown in FIG. 1.

Further toehold riboregulator system designs are described in Example 7.

Figure 3:
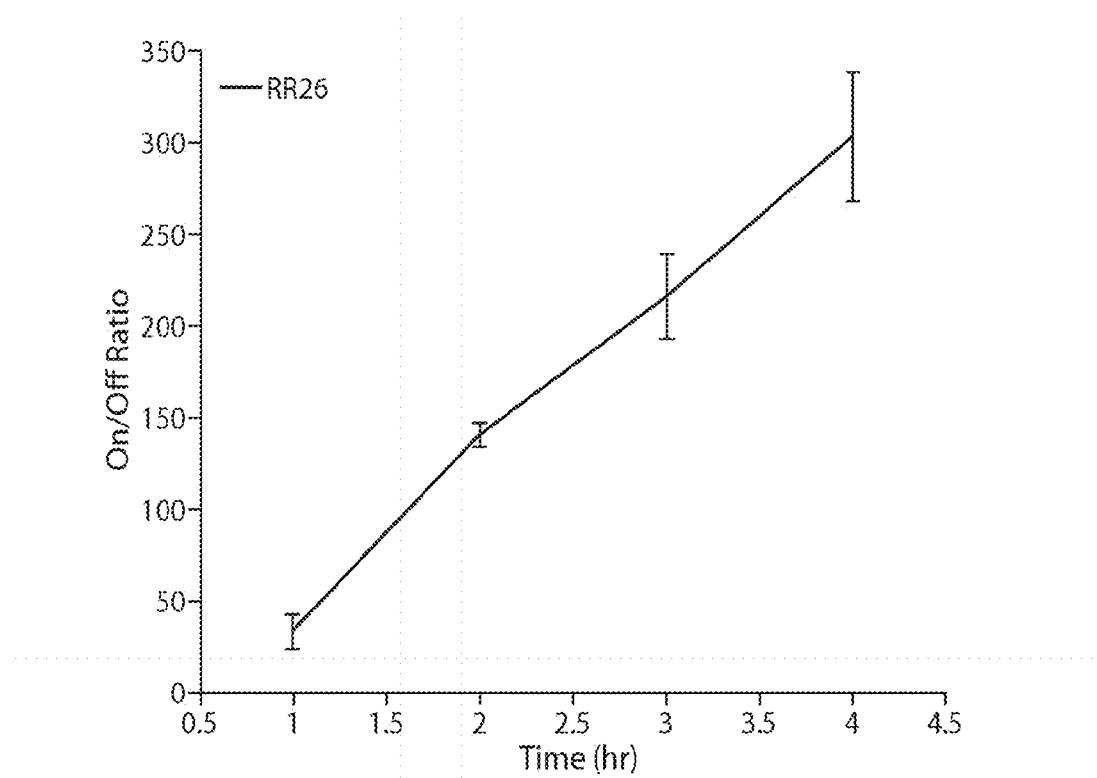
FIG. 3. On/off mode fluorescence ratio obtained for a high performance toehold riboregulator.

As shown in FIG. 3, toehold riboregulators can display strong trans-activation using a target RNA at the taRNA species, with fluorescence increasing by a factor of over 200 only two to three hours after induction. The same measurements were performed in vivo on an additional 60 toehold riboregulator designs and the on/off ratios are displayed in FIG. 4. Roughly one third of the riboregulators tested increase GFP output by a factor of 50 or more in the presence of their cognate taRNA.

Figure 8A:
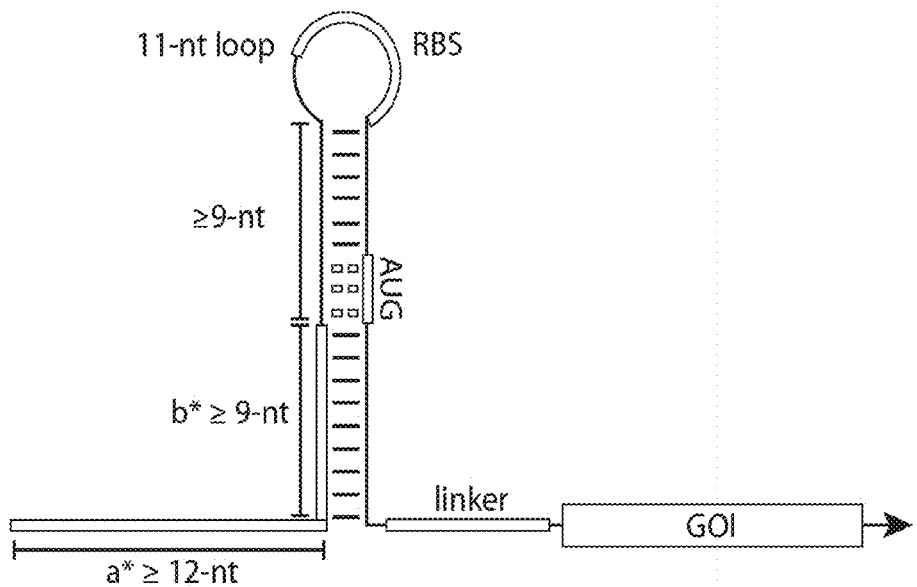
FIG. 8. Design schematics for other endogenous sensors based on the (A) toehold and (B) beacon riboregulators that are programmed to sense targets with the sequence 5'-b-a-3'. Both designs employ strong RNA duplexes before and after the AUG start codon to repress protein translation. (A) Toehold riboregulator with an extended toehold (more than 21 nucleotides (nts) in some implementations) to encourage strong binding of an RNA target with significant secondary structure. crRNA stem unwinding region is reduced in size but will allow trans-activation of translation since the stem nearest RBS is short (typically 6 base pairs (bp)) and likely to spontaneously unwind. (B) Beacon riboregulator possesses a larger loop (typically 32-nts) for target binding and the RBS is now in the loop to allow greater programmability.

Additional experimental testing has also enabled us to gain a better understanding of the crRNA secondary structure and domain lengths required for optimal toehold riboregulator operation. A toehold domain of at least 5 or 6 nts in length is preferable for taRNA initial binding. The toehold domain can therefore be 5, 6, 7, 8, 9, 10, 11, 12, 13, 14, 15, 16, 17, 18, 19, 20, or more nucleotides in length. Moreover, it was also found that the taRNA need only unwind two-thirds of the crRNA stem in order to allow translation of the GOI. Based on these findings, the stem domain may be as small as 12 bps for adequate repression in the crRNA. The stem domain may however be longer than 12 bps, including 13, 14, 15, 16, 17, 18, 19, 20, or more base pairs in length. Furthermore, expanding the loop length to 12-nts and replacement of the RBS with a slightly stronger version with the canonical Shine-Dalgarno sequence did not decrease the degree of repression by the crRNA. Accordingly, the length of the loop domain may be 11, 12, 13, 14, 15, 16, 17, 18, 19, 20 or more nucleotides. Variations of toehold riboregulators are shown in FIG. 8A and are described in greater detail in Example 7.

The invention further provides crRNA/switches having additional features. In some instances, the top three bases of the hairpin stem may be A-U base pairs. In some instances, the bottom three base pairs of the stem may comprise two strong G-C base pairs and one A-U base pair. In some instances, the length of the switch toehold may range from about 12- to about 15-nts. This latter feature may in some instances strengthen the initial binding between a trigger RNA and its switch RNA. In some instances, the size of the hairpin loop may range from about 11- to about 15-nts to enhance translation of the output protein upon switch activation. In some instances, the loop size is 15-nts. In yet other instances, the cognate trigger may be used that unwinds the first 15 of the 18 bases in the switch stem. In some instances, one or more, including all, of these features may be used simultaneously. The Examples demonstrate the results using such riboregulators.

Figure 12A:
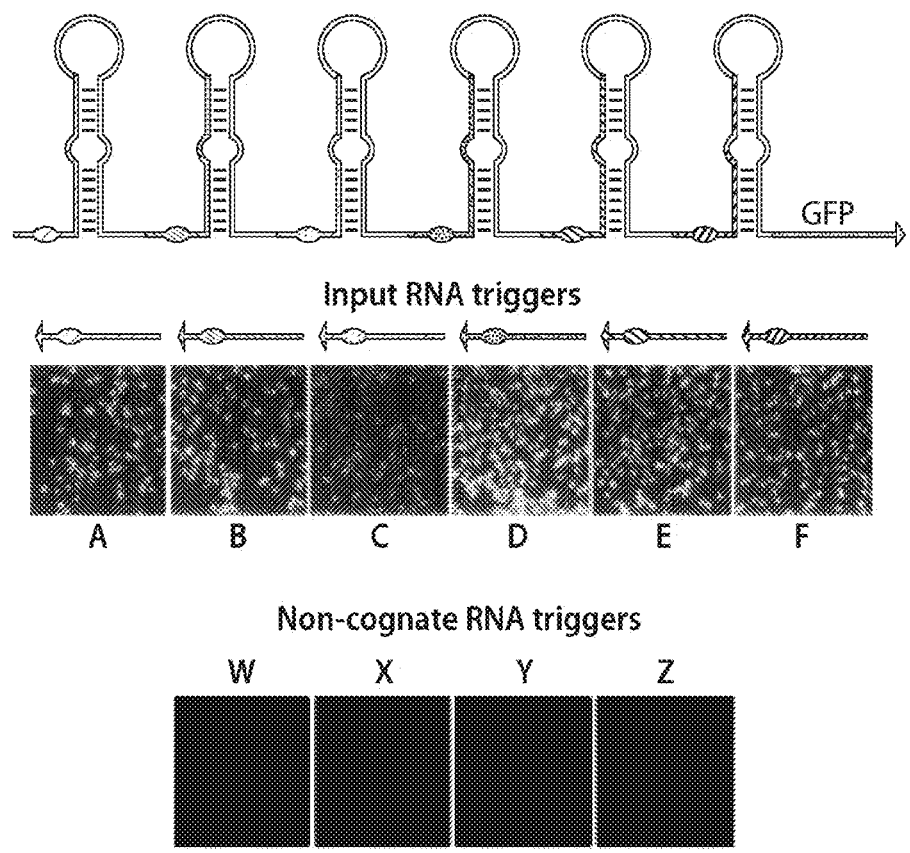
FIG. 12. Implementation of a 6-input OR gate in vivo. (A, top) The OR gate system is comprised of six crRNA arranged in series upstream of the GFP gene. (A, middle) The corresponding six taRNA inputs were all found to activate GFP expression from E. coli colonies induced on LB/IPTG plates. In contrast, four different non-cognate taRNAs did not elicit GFP production when co-expressed with OR gate construct. (B) Flow cytometry measurements of the On/Off mode GFP fluorescence ratio for the OR gate system. All six programmed input RNA tarRNAs exhibit greater than 10-fold higher GFP expression compared to the non-cognate taRNA with lowest GFP leakage levels (Y).
Figure 12B:
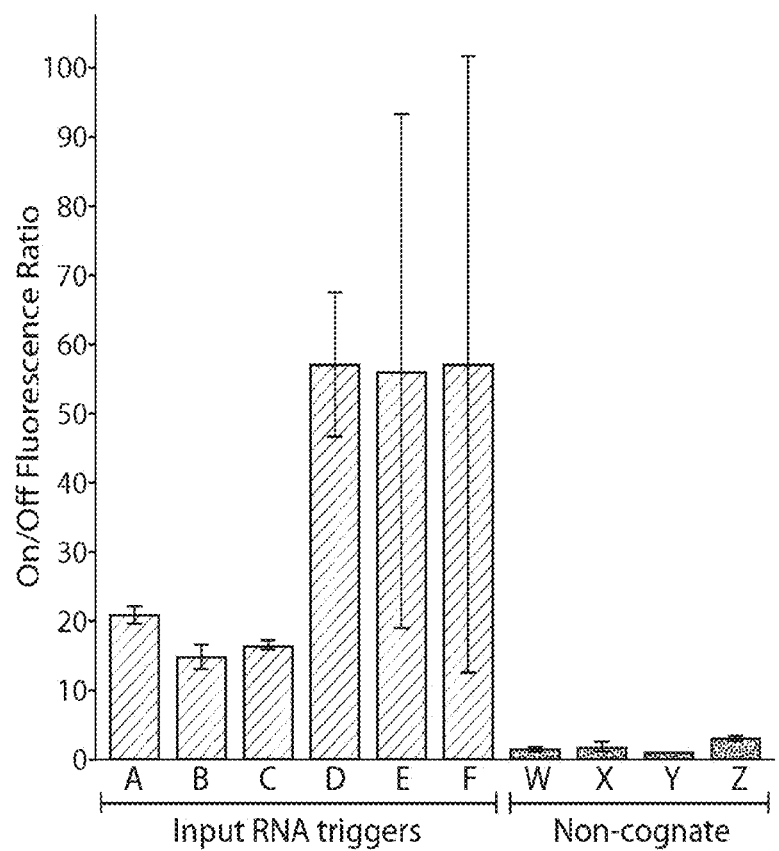

The toehold riboregulators described herein may be used in logic gates that function through more than one trigger RNA or that sense more than one trigger RNA. FIGS. 12 and 13 illustrate these additional embodiments of the invention. FIG. 12 illustrates a toehold riboregulator comprising a plurality of hairpin structures (i.e., stem-loop structures, crRNAs) connected together in a linear manner, and a downstream GOI coding sequence. In the Figure, the riboregulator comprises 6 hairpin structures and a GOI is GFP. Each hairpin structure is connected to a toehold sequence that is complementary to an input RNA trigger (or taRNA). Each of the input RNA triggers (or taRNA) is capable of activating expression of the downstream GOI. This riboregulator is referred to as an "OR" gate because it requires the presence of only one of the input RNA in order to observe expression of the GOI. This OR gate activates expression of GFP when any of the input RNA triggers (or taRNAs) is expressed and binds to its corresponding crRNA sequence. The Figure further shows the on/off fluorescence ratio in the presence of individual input RNA triggers A-F or non-cognate RNA triggers W-Z. The on/off ratios are much greater in the presence of the input RNA triggers as compared to the non-cognate RNA triggers.

FIG. 13 illustrates an "AND" gate which comprises a single hairpin (crRNA) structure with an extended stem region. The crRNA encodes a plurality of regions each acting as a binding domain for a taRNA. Input RNA (or taRNAs) hybridize with one another and can also unwind corresponding portions of the crRNA stem. This system only activates when all input RNA triggers are present to completely unwind the crRNA. It is referred to as an AND gate because it requires all of the input RNA in order to observe expression of the GOI. The Figure further provides photographs showing GFP fluorescence in the presence of different combinations of 3, 4, 5 and 6 input RNA triggers.

Figure 14A:
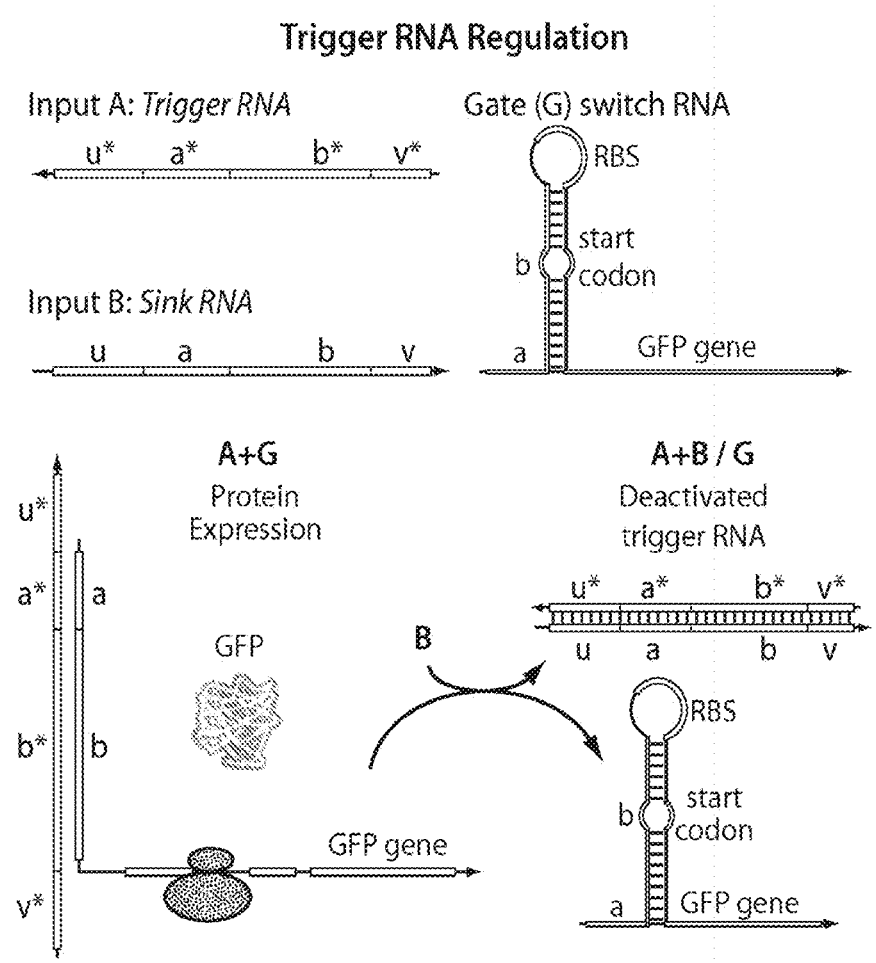
FIG. 14. In vivo demonstration of trigger RNA inactivation by a sink RNA. (A) Schematic showing the molecular interactions underlying the logic operations. The sink RNA is designed to outcompete the switch RNA for binding to the trigger. This preferential binding prevents the trigger from activating the switch whenever the sink is also present. (B) GFP fluorescence measured from the switch RNA with different combinations of trigger and sink RNAs. Ninety percent (90%) repression of fluorescence is observed when the sink is co-expressed with the trigger RNA compared to when the trigger alone is expressed.

In still other aspects, the invention recognizes that it is useful to prevent a trigger RNA from acting on its cognate switch RNA to prevent activation of a system or as a means of adding another layer of logic to an in vivo circuit. Provided herein is a method to reduce or eliminate the activity of a trigger RNA using an RNA referred to herein as a "sink RNA". The sink RNA is designed to outcompete the switch RNA for binding to its cognate trigger strand. In these systems, flanking sequences v* and u* are added to the 5' and 3' ends of the trigger RNA, respectively (FIG. 14A). The cognate sink RNA for the trigger is completely complementary to the central b*-a* region of the trigger and its flanking domains. Consequently, the thermodynamics of the sink-trigger RNA interaction are much stronger than the interaction between the trigger RNA and its cognate switch, which occurs through the shorter b*-a* sequence. This effect leads to preferential binding of the trigger to the sink, and in the event a trigger RNA is bound to a switch, the v* and u* domains will behave as exposed toeholds that the sink RNA can use to complete a branch migration process to drive the trigger off the switch. To make sink-trigger hybridization still more likely, the sink RNA is expressed at a higher level than the trigger RNA. The lengths of the v* and u* domains can vary depending on the particular system. Either domain can be completely removed from the system and still retain the desired network behavior as long as the other domain is present. In other words, the sink RNA may comprise one or both flanking domains. The v* and u* domains may be 12 to 21 nts long, in some instances.

Figure 14B:
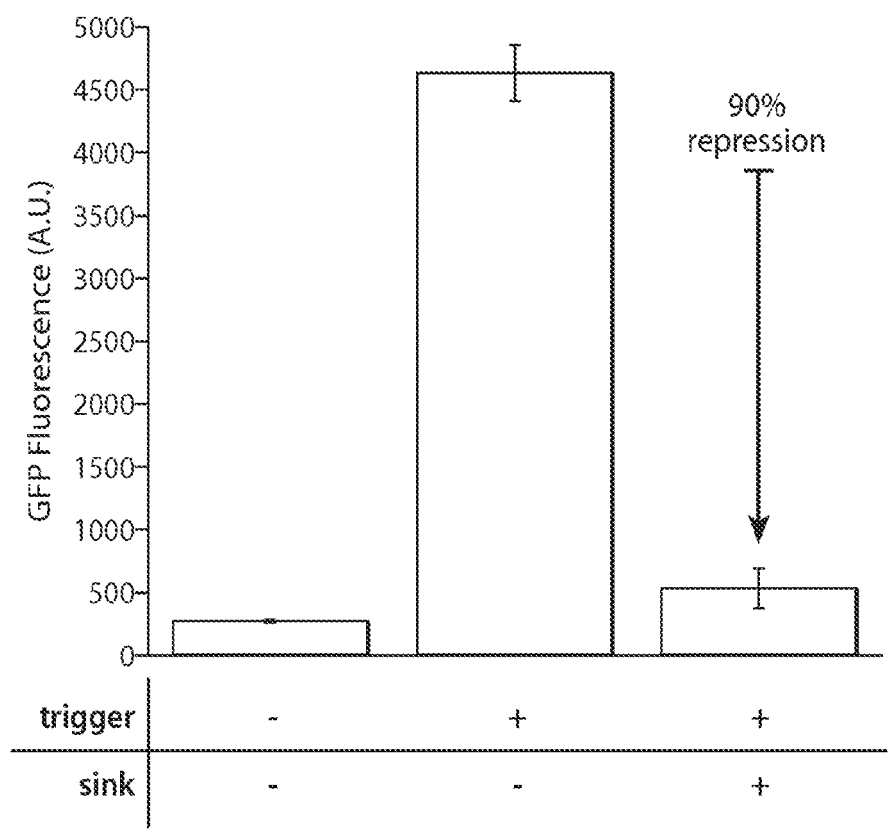

FIG. 14B displays the behavior of the sink-trigger-switch RNA system in *E. coli* using GFP as a model readout. It will be understood that the invention contemplates other systems in which GFP is replaced with a protein (or gene) or interest. When the switch RNA is expressed on its own, there is low output of the GFP reporter protein. When the trigger and switch are co-expressed, binding occurs and the switch activates strongly leading to an increase in GFP output. However, when all three RNAs are co-expressed GFP output drops ~90% from its fully activated level as a result of preferential sink-trigger RNA binding. Overall, the output protein is expressed only when the trigger RNA is present in the absence of the sink; otherwise, protein output from the device is low. As a result, this system carries out the logical operation A N-IMPLY B where the trigger RNA represents the A input and the sink RNA is the B input. The switch RNA in this case acts as the gate performing the A N-IMPLY B operation and the output is protein regulated by the switch RNA.

This approach can also be directly applied to the toehold repressors discussed below. When a trigger/sink combination is used with a repressor, the system turns off only when the trigger RNA is expressed in the absence of the sink RNA. This behavior is equivalent to an A IMPLY B operation where the trigger serves as the A input and the sink is the B input.

The sink RNA/trigger RNA system can be applied to thresholding circuits. The experiments shown in FIG. 14 employed constant levels of each of the trigger, switch, and sink RNAs. A stoichiometric excess of the sink RNA was also expressed over the trigger RNA to ensure complete elimination of free trigger RNAs from the cell. However, if the levels of both the trigger and sink RNAs are allowed to vary, this system can provide thresholding behavior. For instance, if the expression of the sink RNA is held constant at a medium level but the expression of trigger RNA is varied from low to high levels, the switch RNA will be activated once the trigger RNA concentration exceeds that of the sink RNA concentration (or a particular percentage of the sink RNA concentration subject to variability in RNA hybridization behavior in the cell or non-cellular environment). Alternatively, if the expression of the trigger RNA is held constant and the expression of the sink RNA is varied, the sink RNA acts as a modulator of trigger RNA activity, tuning protein output from the switch RNA up or down as a function of sink RNA concentration. These behaviors can be used for neural network type behavior (see for example Qian et al. Nature, 475:368-372, 2011), and for constructing majority and minority gates.

The invention therefore contemplates toehold riboregulator compositions (or systems or devices) comprising a switch RNA (comprising a coding sequence for a gene of interest), a trigger RNA, and a sink RNA. In some instances, the trigger RNA is an activating RNA (i.e., its presence, at a sufficient level, activates protein expression (or translation) from the switch RNA and thus of the coding sequence of interest). In some instances, the trigger RNA is a repressing RNA (i.e., its presence, at a sufficient level, represses protein expression (or translation) from the switch RNA and thus of the coding sequence of interest). The inter-related structural features of the switch RNA, trigger RNA and sink RNA are as described herein.

Figure 15A:
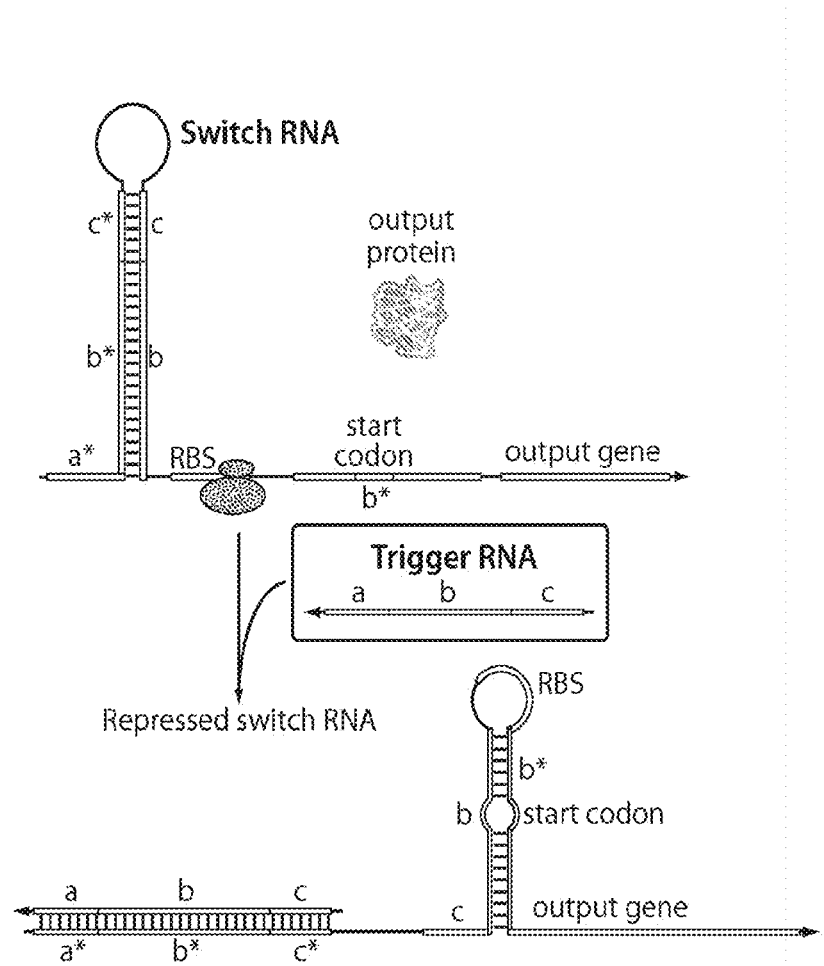
FIG. 15. Toehold repressor design and performance. (A) Schematic illustration showing the molecular interactions of a toehold repressor system. The trigger RNA causes the switch RNA to refold into a configuration that prevents the ribosome from accessing binding elements on the RNA. (B) Repression levels measured from a library of 44 toehold repressors. Half of the systems provide greater than 90% repression. Dashed and dotted lines at 90% and 80% repression, respectively, are provided.

As discussed briefly herein, toehold riboregulators may also function as repressors of protein translation. In accordance with the invention, a new class of riboregulators is provided that can repress translation of a gene of interest in response to a trigger RNA by a novel strand reconfiguration mechanism. These switch RNA/trigger RNA riboregulator systems are referred to herein as toehold repressors as a result of their toehold-based interaction mechanism. The molecular implementation of these RNA devices is shown in FIG. 15A. The toehold repressors consist of two RNAs: a switch RNA that contains the coding sequence(s) of the gene of interest, and a trigger RNA that causes protein translation from the switch to stop. In the illustrated example, the switch RNA contains a 5'-toehold domain that is about 15-nts in length. This toehold is followed by a stem-loop region with a stem that is about 30-nts long and contains a 9-nt loop. The domains b and c that form the stem are about 18- and 12-nts, respectively. The stem contains bulges at three locations 8-, 16-, and 24-nts from the bottom of the stem. These bulges are incorporated to reduce the likelihood of transcriptional termination, but are not required for successful operation. The bulges can also be moved to other locations and increased in number without necessarily preventing successful switch operation. The size of the loop can also be changed without affecting operation. The stem region is followed by a single-stranded region that contains (in the 5' to 3' direction): a 4-nt spacer, the RBS sequence (8-nt in this implementation), a 6-nt spacer, the start codon AUG, a 9-nt spacer, a 21-nt linker, and then the coding sequence for the gene of interest. As a result of the exposed RBS to start codon region in the switch RNA, expression is turned on in the absence of the trigger RNA.

The trigger RNA is a single-stranded RNA containing a sequence that is perfectly complementary to the early region of the switch RNA as shown in FIG. 15A, and thus it has a total length of 45-nts. When the trigger and switch RNAs are co-expressed, the trigger RNA binds to the toehold domain of the switch RNA and completes a branch migration reaction with the switch stem. Displacement of the stem completely exposes 30-nts and the loop of the switch RNA. These newly exposed bases can rapidly refold. This strand reconfiguration causes the downstream bases of the switch RNA to form a new hairpin domain. This hairpin sequesters the region surrounding the start codon of the gene, repressing in an identical manner to the switch RNA in toehold switch translational activator system. In addition, it is worth noting that the trigger-switch RNA complex formed by the toehold repressors yields a hairpin with an extended toehold that can in turn interact with an activating trigger RNA having the sequence 5'-b*-a*-3' to reactivate translation of the gene/protein of interest. The behavior of this system with separate repressing and activating triggers is equivalent to an A IMPLY B gate, where A is the repressing trigger and B is the activating trigger.

Like the toehold activator switches, toehold repressors can adopt trigger RNAs with virtually arbitrary sequences. Consequently, it is possible to design large repressor libraries with a high degree of orthogonality. In addition, they can be used to trigger translational repression in response to exogenous and endogenous RNAs.

The invention further contemplates and provides higher order logic circuitry based on toehold repressors. Given their similarities to the toehold activator switches, toehold repressor switches can be incorporated into complex logic systems in much the same way as the translational activators.

Figure 9A:
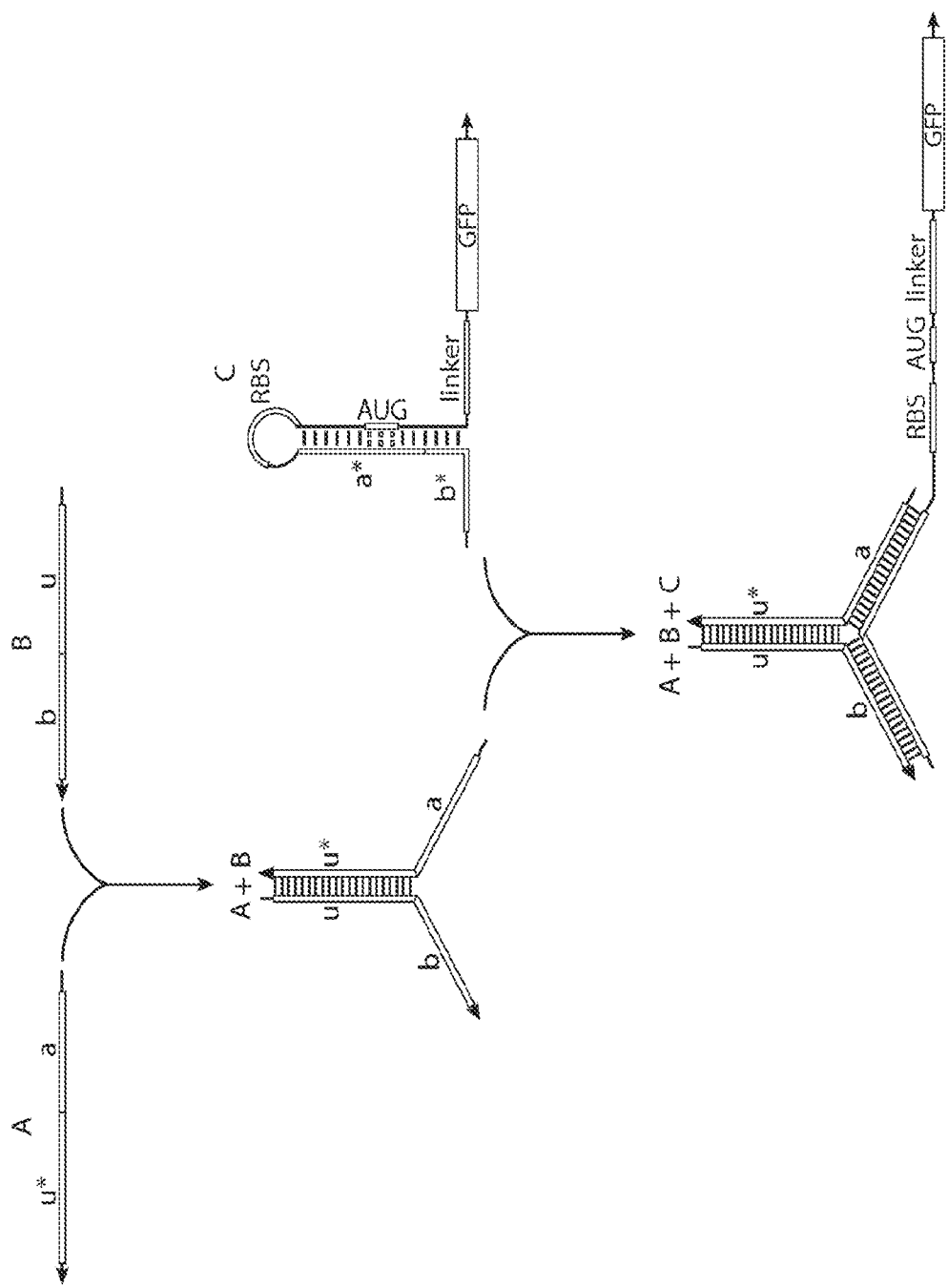
FIG. 9 illustrates a system in which two taRNAs work together and contribute to the 5'-a-b-3' sequence that hybridizes to a riboregulator crRNA. (A) Schematic illustration of a two-input AND gate system in which RNA strands A and B are inputs and strand C, a crRNA, functions as the gate. (B) On/off fluorescence ratios obtained for all combinations of RNA strands A, B, and C.
Figure 9B:
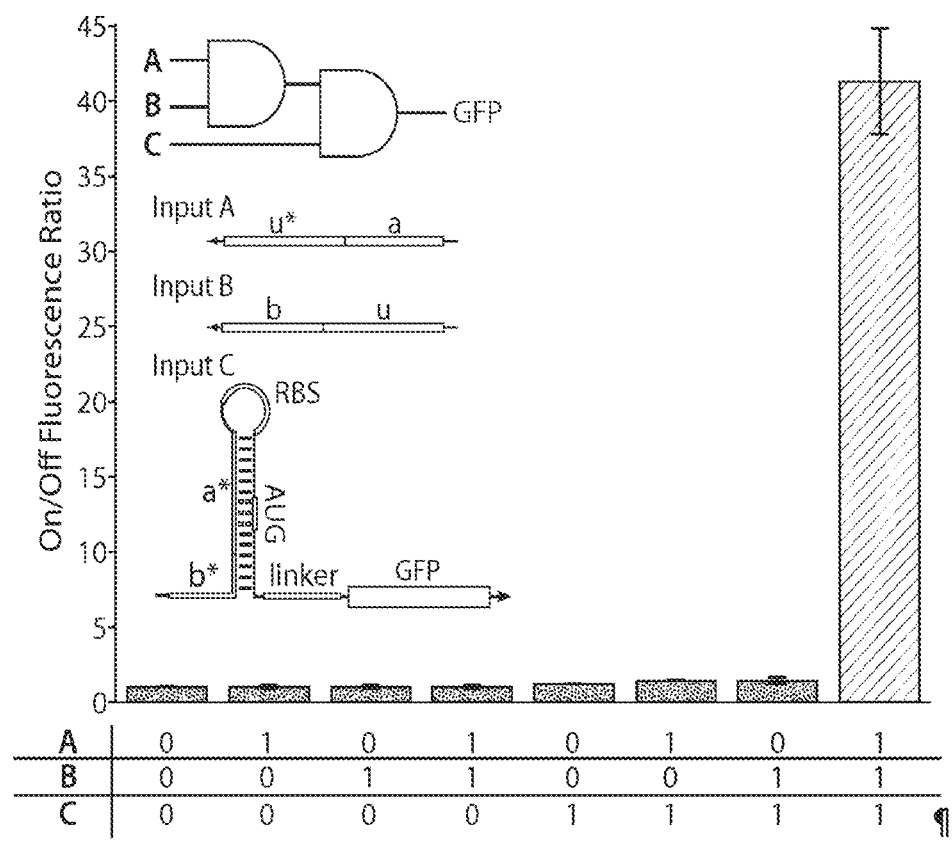
Figure 10:
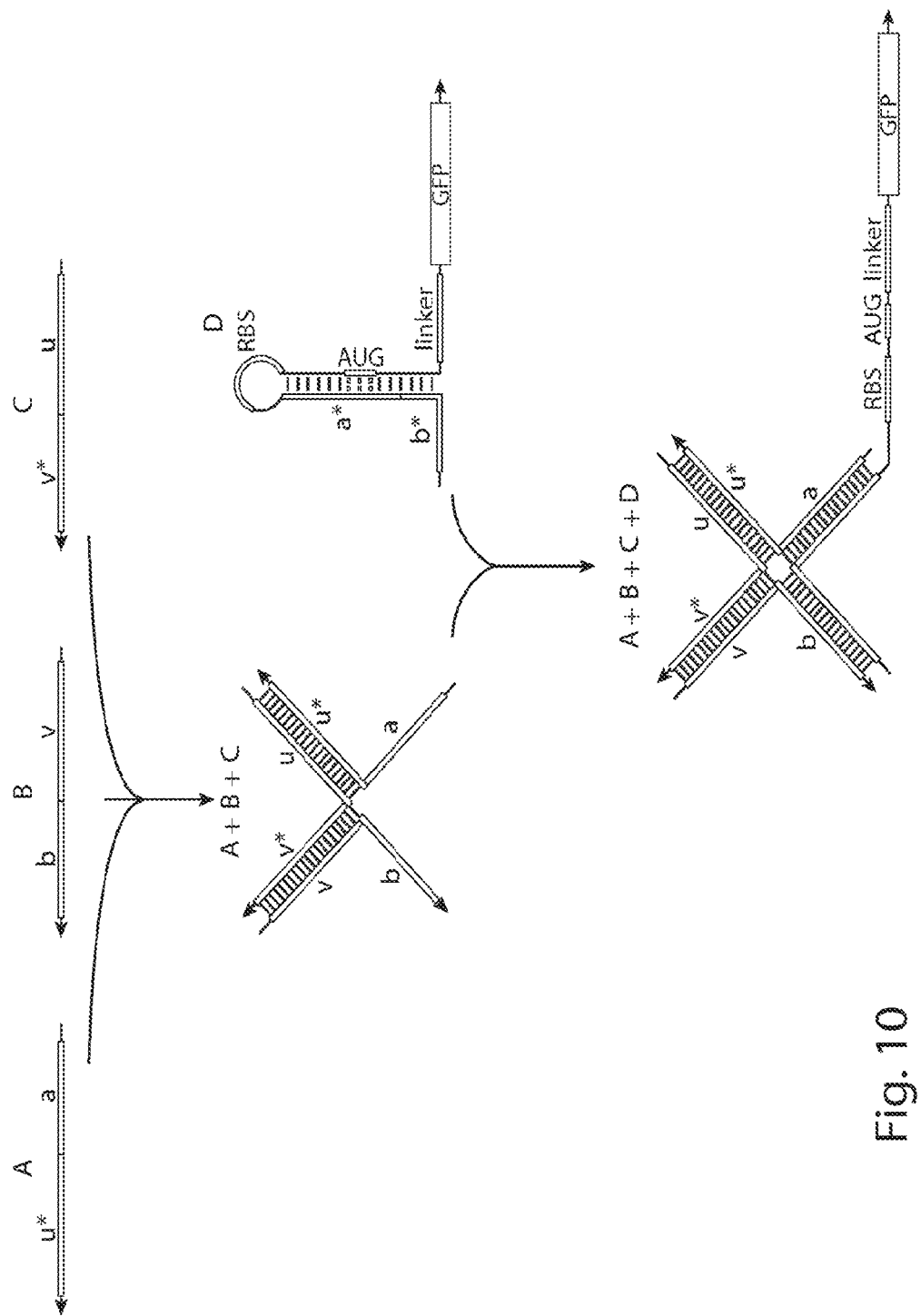
FIG. 10 illustrates a system in which two taRNAs each with part of the 5'-a-b-3' sequence are brought into close proximity by a third taRNA that does not contain any part of the 5'-a-b-3' sequence.

Thus, some aspects provide NAND logic gates, which are repressor versions of the systems shown in FIGS. 9, 10 and 13. N-bit NAND logic can be carried out using complexes formed by N-input RNA strands that produce a functional trigger RNA. For the simple 2-bit case, two input RNAs are programmed to bind to one another in the same fashion as the taRNA used for the 2-bit AND system. Each of these input RNAs contains only part of the cognate trigger for the switch RNA and thus each is incapable on its own of carrying out the branch migration required to change the state of the switch. However, when both input RNAs bind, they form a complete trigger RNA sequence and can bind to the switch toehold and unwind its stem to trigger repression of translation. This base concept can be extended to N-bit operation by dividing the complete trigger RNA sequence among multiple input RNAs that bind together in the proper order to provide the trigger sequence. In an alternative approach, two inputs can be used to each provide roughly half of the trigger sequence. These two inputs are then brought into close proximity through the assembly of N-2 programmed input RNAs.

Other aspects provide NOR logic gates, which are repressor versions of the systems shown in FIGS. 11 and 12. N-bit NOR logic can be evaluated by using concatenated toehold repressor hairpins positioned upstream of the coding sequence for the protein of interest. For the simple two-bit NOR case, the NOR gate is composed of a pair of orthogonal toehold repressors upstream of the gene. In the absence of either trigger RNA, the RBS and start codon for both toehold repressors are exposed and available for translation. When only one of the trigger RNAs is expressed, one of the RBS-start codons regions remains free for translation and the ribosome has sufficient processivity to unwind strong hairpins along its path. Consequently, the 2-bit NOR gate can only turn OFF when both trigger RNAs are expressed and cause strand reconfiguration for both of the toehold repressor domains. These base concepts can be extended to N-bit NOR gate operation.

The riboregulators provided herein can be used in complex logic circuitry. As an example, toehold switches and toehold repressors can be incorporated into higher-order logic circuits for AND/NAND, OR/NOR, and IMPLY/N-IMPLY operations. The modularity of this computational approach enables even more complex calculations by combining all these operations in a single extended gate RNA containing concatenated toehold regulator hairpins along with a network of affiliated input trigger and sink RNAs. Importantly, the base set of computational elements provided herein enables evaluation of any logic operation by decomposing it into an expression in disjunctive normal form (i.e., an outer OR operation applied to nested NOT and AND expressions), such as:

(A AND B) OR (C AND D) OR (E AND F AND G), or with the addition of sink RNAs:

NOT (A AND B) OR (C AND (NOT D)) OR (E AND F AND G).

Analogous expressions can be evaluated with the NAND and NOR gates incorporated as well. Computations using the toehold regulators operate in a single computational layer (i.e., they do not require the output from one operation to be used as an input for a later operation) and can readily integrate multiple input species, which increases their computation speed and enables fewer gates to be used. This is in contrast to other molecular computation techniques such as those described by Qian et al. Science, 332:1196-1201, 2011 and Moon et al. Nature, 491:249-253, 2012.

Still further embodiments provide and apply multiple input XOR and XNOR logic. As an example, N-bit XOR (XNOR) calculations can be performed using a combination of the OR (NOR) gates and trigger/sink RNAs. The main concepts behind this operation can be described using the simple 2-bit XOR case. The constitutively-expressed gate RNA for this operation is a 2-bit OR system containing a pair of concatenated orthogonal toehold switches upstream of the regulated gene. These switches accept cognate triggers A and B. Expression of triggers A and B is controlled by two orthogonal chemical inducers indA and indB, respectively. Each of the triggers has a cognate sink RNA A* and B* that preferentially bind to their corresponding trigger to prevent activation of the switch hairpin in the gate. Importantly, these sink RNAs are expressed from a higher copy plasmid or using a stronger promoter than the trigger RNAs to ensure they reach higher concentrations when induced in the cell. Furthermore, production of sink RNAs A* and B* is tied to indB and indA, respectively. Consequently, addition of indA to the growth media will cause expression of trigger A and sink B*, while addition indB will cause trigger B and sink A* to be produced.

When only one inducer is present, expression of the trigger RNA and a non-cognate sink RNA allows activation of one of the switch hairpins within the gate RNA. However, when both inducers are present, the two trigger RNAs are expressed, but sink RNAs are also transcribed at higher levels. These sink RNAs outcompete the gate RNA for trigger molecules and prevent activation of protein translation. In the case where neither inducer is present, triggers are not expressed and the gate remains off. As a result, this synthetic gene network carries out 2-bit XOR logic.

This general approach can be extended to N-bit XOR logic in which each of the N inducers initiates expression of a single trigger RNA along with a complement of N-1 non-cognate sink RNAs. Lastly, N-bit XNOR is evaluated by replacing the N-bit OR gate formed from N concatenated toehold switches with a set of N concatenated toehold repressors.

Beacon Riboregulators

Figure 5:
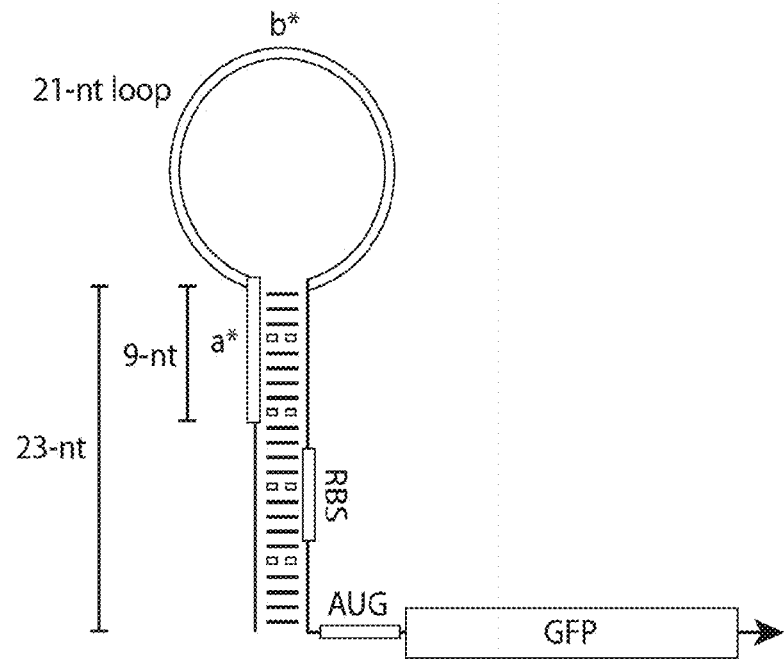
FIG. 5. Beacon riboregulator base design. The taRNA has the sequence 5'-b-a-3'.

In a beacon riboregulator system, the crRNA comprise a stem domain of variable length that contains the RBS and, in some cases, the start codon (see FIG. 5 for an exemplary embodiment). The stem domain also includes a ~9 bp region upstream of the RBS containing nucleotides complementary to the taRNA target. Binding of the taRNA target is initiated through a large (~21-nt) loop domain in the crRNA and proceeds into the 5' portion of the crRNA stem domain. Binding of the taRNA target through this big-loop-linear interaction results in a rigid duplex that provides mechanical force to encourage the rest of the crRNA to unwind. After unwinding, both the RBS and start codon of the activated crRNA are exposed, enabling translation of the GOI. Since the target binding region of the crRNA is independent of both the RBS and start codon, the taRNA of the beacon riboregulator can, in principle, adopt arbitrary sequences. taRNAs having little secondary structure will offer the better reaction kinetics. In addition, the target taRNA must be sufficiently long to force unwinding of the crRNA stem domain.

Figure 6:
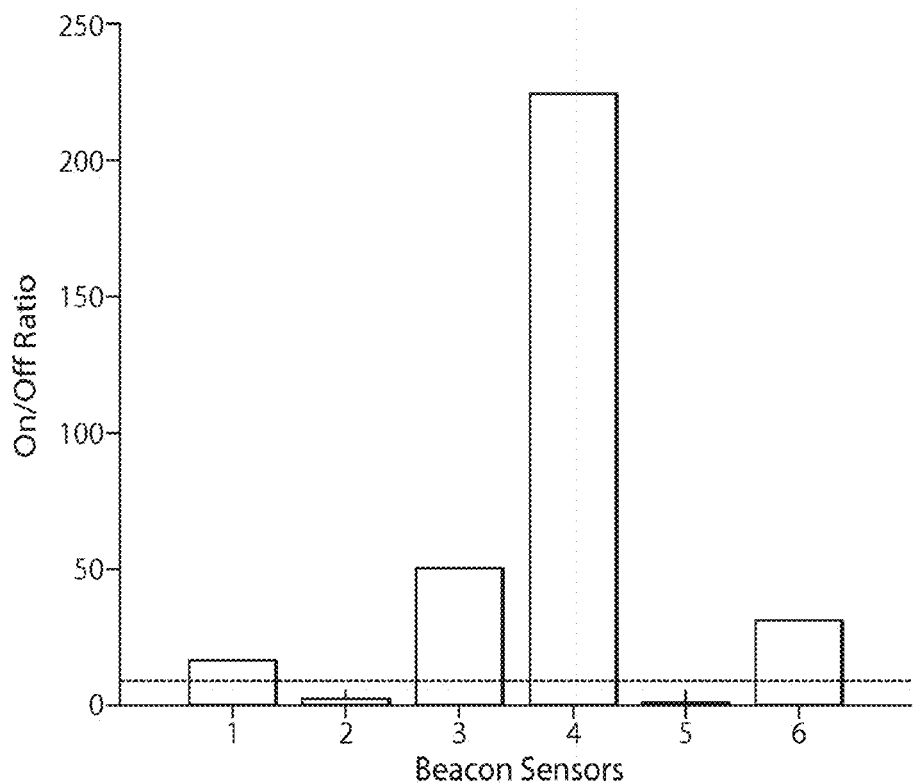
FIG. 6. On/off median fluorescence intensity obtained for a set of six beacon riboregulator devices. Dotted red line marks an on/off ratio of 10.

Beacon riboregulators were tested using identical conditions to those used for the toehold riboregulator devices. FIG. 6 shows the on/off median fluorescence intensity ratios obtained for six beacon riboregulators. Four of the devices show on/off ratios exceeding ten with one design exceeding a factor of 200.

Figure 8B:
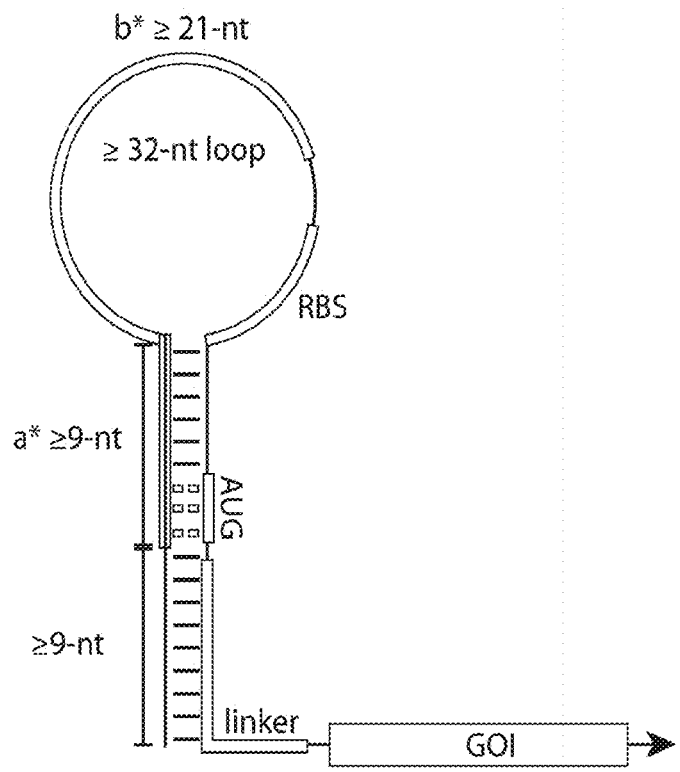

Variations of toehold riboregulators are shown in FIG. 8B.

As described herein, the trans-activating RNA (taRNA) (also referred to herein as trigger RNA) may be small RNA molecules encompassing only those sequences that hybridize to the binding domains (first or second or first and second domains) of the toehold or beacon riboregulators, or they may be longer RNA molecules such as mRNA molecules that hybridize to the binding domains of the toehold or beacon riboregulators using only part of their sequence. In still other instances, activation of the crRNA may require two or more RNA or other nucleic acid molecules that work in concert to unwind the hairpin structure of the crRNA. The taRNA may be of varied length. In some instances, the taRNA is about 30 nts in length. Such a taRNA may bind to a crRNA having a 12 nt toehold domain, as described in herein including in Example 7.

The crRNA of the invention comprise a hairpin structure that minimally comprises a stem domain and a loop domain. The crRNA and its hairpin typically comprise a single nucleic acid molecule or portion thereof that adopts secondary structure to form (a) a duplex (double helical, partially or fully double-stranded) region (referred to herein as the stem domain) when complementary sequences within the molecule hybridize to each other via base pairing interactions and (b) a single-stranded loop domain at one end of the duplex. FIGS. 1, 5 and 8 show various stem-loop structures. In various embodiments of the invention the stem domain, while predominately double-stranded, may include one or more mismatches, bulges, or inner loops. The length of a stem domain may be measured from the first pair of complementary nucleotides to the last pair of complementary bases and includes mismatched nucleotides (e.g., pairs other than AT, AU, GC), nucleotides that form a bulge, or nucleotides that form an inner loop.

It will be appreciated that although a hairpin is formed from a single nucleic acid molecule, the two regions or sequences of the molecule that form the stem domain may be referred to herein as "strands". Thus the stem may be referred to herein as being partially or fully double-stranded. Nucleic acid sequences within a single molecule that are complementary to each other and are capable of forming a stem domain are said to be "self-complementary" or to "self-hybridizing" or able to "self-hybridize". In general, the hairpin and stem domains described herein form at and are stable under physiological conditions, e.g., conditions present within a cell (e.g., conditions such as pH, temperature, and salt concentration that approximate physiological conditions). Such conditions include a pH between 6.8 and 7.6, more preferably approximately 7.4. Typical temperatures are approximately 37° C., although prokaryotes and some eukaryotic cells such as fungal cells can grow at a wider temperature range including at temperatures below or above 37° C.

Various of the nucleic acids of the invention may be referred to herein as non-naturally occurring, artificial, engineered or synthetic. This means that the nucleic acid is not found naturally or in naturally occurring, unmanipulated, sources. A non-naturally occurring, artificial, engineered or synthetic nucleic acid may be similar in sequence to a naturally occurring nucleic acid but may contain at least one artificially created insertion, deletion, inversion, or substitution relative to the sequence found in its naturally occurring counterpart. A cell that contains an engineered nucleic acid may be referred to as an engineered cell.

Various embodiments of the invention involve nucleic acid sequences that are complementary to each other. In some instances, the sequences are preferably fully complementary (i.e., 100% complementary). In other instances, however the sequences are only partially complementary. Partially complementary sequences may be at least 60%, at least 70%, at least 80%, at least 90%, or at least 95% complementary. Sequences that are only partially complementary, when hybridized to each other, will comprise double-stranded regions and single-stranded regions. The single-stranded regions may be single mismatches, loops (where for instances a series of consecutive nucleotides on one strand are unhybridized), bulges (where for instances a series of consecutive nucleotides on both strands, opposite to each other, are unhybridized). It will be appreciated that complementarity may be determined with respect to the entire length of the two sequences or with respect to portions of the sequences.

Nucleic acids and/or other moieties of the invention may be isolated. As used herein, "isolated" means separate from at least some of the components with which it is usually associated whether it be from a naturally occurring source or made synthetically.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Nucleic acids may be single-stranded, double-stranded, and also tripled-stranded.

A naturally occurring nucleotide consists of a nucleoside, i.e., a nitrogenous base linked to a pentose sugar, and one or more phosphate groups which is usually esterified at the hydroxyl group attached to C-5 of the pentose sugar (indicated as 5') of the nucleoside. Such compounds are called nucleoside 5'-phosphates or 5'-nucleotides. In DNA the pentose sugar is deoxyribose, whereas in RNA the pentose sugar is ribose. The nitrogenous base can be a purine such as adenine or guanine (found in DNA and RNA), or a pyrimidine such as cytosine (found in DNA and RNA), thymine (found in DNA) or uracil (found in RNA). Thus, the major nucleotides of DNA are deoxyadenosine 5'-triphosphate (dATP), deoxyguanosine 5'-triphosphate (dGTP), deoxycytidine 5'-triphosphate (dCTP), and deoxythymidine 5'-triphosphate (dTTP). The major nucleotides of RNA are adenosine 5'-triphosphate (ATP), guanosine 5'-triphosphate (GTP), cytidine 5'-triphosphate (CTP) and uridine 5'-triphosphate (UTP). In general, stable base pairing interactions occur between adenine and thymine (AT), adenine and uracil (AU), and guanine and cytosine (GC). Thus adenine and thymidine, adenine and uracil, and guanine and cytosine (and the corresponding nucleosides and nucleotides) are referred to as being complementary to each other.

In general, one end of a nucleic acid has a 5'-hydroxyl group and the other end of the nucleic acid has a 3'-hydroxyl group. As a result, the nucleic acid has polarity. The position or location of a sequence or moiety or domain in a nucleic acid may be denoted as being upstream or 5' of a particular marker, intending that it is between the marker and the 5' end of the nucleic acid. Similarly, the position or location of a sequence or moiety or domain in a nucleic acid may be denoted as being downstream or 3' of a particular marker, intending that it is between the marker and the 3' end of the nucleic acid.

Nucleic acids may comprise nucleotide analogs including non-naturally occurring nucleotide analogs. Such analogs include nucleoside analogs (e.g., 2-aminoadenosine, 2-thiothymidine, inosine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

The nucleic acids of the invention, including the crRNA and taRNA, may be provided or present in a larger nucleic acid. The larger nucleic acid may be responsible for the transcription and thus production of the crRNA and taRNA, as described in Example 1, for example. The larger nucleic acid may comprise a nucleotide sequence that is transcribed to produce the crRNA and taRNA of the invention. For convenience, the invention may refer to the larger nucleic acid as comprising the crRNA and/or taRNA although it is to be understood that in practice this intends that the larger nucleic acid comprises a sequence that encodes the crRNA and/or taRNA. Such encoding sequences may be operable linked to other sequences in the larger nucleic acid such as but not limited to origins of replication. As used herein, "operably linked" refers to a relationship between two nucleic acid sequences wherein the production or expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective association is acceptable.

As used herein, a regulatory sequence or element intends a region of nucleic acid sequence that directs, enhances, or inhibits the expression (e.g., transcription, translation, processing, etc.) of sequence(s) with which it is operatively linked. The term includes promoters, enhancers and other transcriptional and/or translational control elements. The crRNA and taRNA moieties of the invention may be considered to be regulatory sequences or elements to the extent they control translation of a gene of interest that is operably linked to the crRNA. The invention contemplates that the crRNA and taRNA of the invention may direct constitutive or inducible protein expression. Inducible protein expression may be controlled in a temporal or developmental manner.

The term vector refers to a nucleic acid capable of mediating entry of, e.g., transferring, transporting, etc., a second nucleic acid molecule into a cell. The transferred nucleic acid is generally linked to, e.g., inserted into, the vector nucleic acid. A vector may include sequences that direct autonomous replication, or may include sequences sufficient to allow integration into host cell DNA. Useful vectors include, for example, plasmids (typically DNA molecules although RNA plasmids are also known), cosmids, and viral vectors.

In the context of the invention, reporter proteins are typically used to visualize activation of the crRNA. Reporter proteins suitable for this purpose include but are not limited to fluorescent or chemiluminescent reporters (e.g., GFP variants, luciferase, e.g., luciferase derived from the firefly (*Photinus pyralis*) or the sea pansy (*Renilla reniformis*) and mutants thereof), enzymatic reporters (e.g., β-galactosidase, alkaline phosphatase, DHFR, CAT), etc. The eGFPs are a class of proteins that has various substitutions (e.g., Thr, Ala, Gly) of the serine at position 65 (Ser65). The blue fluorescent proteins (BFP) have a mutation at position 66 (Tyr to His mutation) which alters emission and excitation properties. This Y66H mutation in BFP causes the spectra to be blue-shifted compared to the wtGFP. Cyan fluorescent proteins (CFP) have a Y66W mutation with excitation and emission spectra wavelengths between those of BFP and eGFP. Sapphire is a mutant with the suppressed excitation peak at 495 nM but still retaining an excitation peak at 395 and the emission peak at 511 nM. Yellow FP (YFP) mutants have an aromatic amino acid (e.g. Phe, Tyr, etc.) at position 203 and have red-shifted emission and excitation spectra.

It is to be understood that although various embodiments of the invention are described in the context of RNA, the nucleic acids of the invention can be RNA or DNA. In general, RNA and DNA can be produced using in vitro systems, within cells, or by chemical synthesis using methods known in the art. It will be appreciated that insertion of crRNA elements upstream of an open reading frame (ORF) can be accomplished by modifying a nucleic acid comprising the ORF.

The invention provides DNA templates for transcription of a crRNA or taRNA. The invention also provides DNA constructs and plasmids comprising such DNA templates. In certain embodiments, the invention provides a construct comprising the template for transcription of a crRNA or a taRNA operably linked to a promoter.

In certain embodiments, the invention provides a DNA construct comprising (i) a template for transcription of a crRNA; and (ii) a promoter located upstream of the template. In certain embodiments, a construct or plasmid of the invention includes a restriction site downstream of the 3' end of the portion of the construct that serves as a template for the crRNA, to allow insertion of an ORF of choice. The construct may include part or all of a polylinker or multiple cloning site downstream of the portion that serves as a template for the crRNA. The construct may also include an ORF downstream of the crRNA.

In certain embodiments, the invention provides a DNA construct comprising (i) a template for transcription of a taRNA; and (ii) a promoter located upstream of the template. The invention further provides a DNA construct comprising: (i) a template for transcription of a crRNA; (ii) a promoter located upstream of the template for transcription of the crRNA; (iii) a template for transcription of a taRNA; and (iv) a promoter located upstream of the template for transcription of the taRNA. The promoters may be the same or different.

The constructs may be incorporated into plasmids, e.g., plasmids capable of replicating in bacteria. In certain embodiments, the plasmid is a high copy number plasmid (e.g., a pUC-based or pBR322-based plasmid), while in other embodiments, the plasmid is a low or medium copy number plasmid, as these terms are understood and known in the art. The plasmid may include any of a variety of origins of replication, which may provide different copy numbers. For example, any of the following may be used (copy numbers are listed in parenthesis): ColE1 (50-70 (high)), p15A (20-30 (medium)), pSC1O1 (10-12 (low)), pSOO1* (<4 (lowest). It may be desirable to use plasmids with different copy numbers for transcription of the crRNA and the taRNA in order to alter their relative amounts in a cell or system. In addition, in certain embodiments a tunable copy number plasmid is employed.

The invention further provides viruses and cells comprising the nucleic acids, constructs (such as DNA constructs), and plasmids described above. In various embodiments, the cell is a prokaryotic cell. In various embodiments, the cell is a eukaryotic cell (e.g., a fungal cell, mammalian cell, insect cell, plant cell, etc.). The nucleic acids or constructs may be integrated into a viral genome using recombinant nucleic acid technology, and infectious virus particles comprising the nucleic acid molecules and/or templates for their transcription can be produced. The nucleic acid molecules, DNA constructs, plasmids, or viruses may be introduced into cells using any of a variety of methods known in the art, e.g., electroporation, calcium-phosphate mediated transfection, viral infection, etc.

As discussed herein, the nucleic acid constructs can be integrated into the genome of a cell. Such cells may be present in vitro (e.g., in culture) or in vivo (e.g., in an organism). The invention further provides transgenic plants and non-human transgenic animals comprising the nucleic acids, DNA constructs, and/or plasmids of the invention. Methods for generating such transgenic organisms are known in the art.

The invention further provides a variety of kits. For example, the invention provides a kit comprising a plasmid, wherein a first plasmid comprises (i) a template for transcription of a crRNA, and (ii) a promoter located upstream of the template for transcription of the crRNA element, and optionally a second plasmid that comprises (i) a template for transcription of a cognate (complementary) taRNA element, and (ii) a promoter located upstream of the template for transcription of the taRNA element. The promoters may be the same or, preferably, different. One or more of the promoters may be inducible. The plasmids may have the same or different copy numbers. The invention further provides a kit comprising a single plasmid that comprises a template for transcription of a crRNA element and a promoter located upstream of the template for transcription of the crRNA element and further comprises a template for transcription of a cognate taRNA element and a promoter located upstream of the template for transcription of the cognate taRNA element. In certain embodiments, the plasmids comprise one or more restriction sites upstream or downstream of the template for transcription of the crRNA element. If downstream, the restriction sites may be used for insertion of an open reading frame of choice. The kits may further include one or more of the following components: (i) one or more inducers; (ii) host cells (e.g., prokaryotic or eukaryotic host cells); (iii) one or more buffers; (iv) one or more enzymes, e.g., a restriction enzyme; (v) nucleic acid isolation and/or purification reagents; (vi) a control plasmid lacking a crRNA or taRNA sequence; (vii) a control plasmid containing a crRNA or taRNA sequence or both; (viii) sequencing primers; (ix) instructions for use. The control plasmids may comprise a reporter sequence.

The riboregulators of the invention in some instances comprise a consensus prokaryotic RBS. However, in various embodiments of the invention any of a variety of alternative sequences may be used as the RBS. The sequences of a large number of bacterial ribosome binding sites have been determined, and the important features of these sequences are known. Preferred RBS sequences for high level translation contain a G-rich region at positions −6 to −11 with respect to the AUG and typically contain an A at position −3. Exemplary RBS sequences for use in the present invention include, but are not limited to, AGAGGAGA (or subsequences of this sequence, e.g., subsequences at least 6 nucleotides in length, such as AGGAGG). Shorter sequences are also acceptable, e.g., AGGA, AGGGAG, GAGGAG, etc. Numerous synthetic ribosome binding sites have been created, and their translation initiation activity has been tested. In various embodiments any naturally occurring RBS may be used in the crRNA constructs. The activity of any candidate sequence to function as an RBS may be tested using any suitable method. For example, expression may be measured as described in Example 1 of published PCT application WO 2004/046321, or as described in reference 53 of that published PCT application, e.g., by measuring the activity of a reporter protein encoded by an mRNA that contains the candidate RBS appropriately positioned upstream of the AUG. Preferably an RBS sequence for use in the invention supports translation at a level of at least 10% of the level at which the consensus RBS supports translation (e.g., as measured by the activity of a reporter protein). For example, if the candidate RBS is inserted into a control plasmid in place of the consensus RBS, the measured fluorescence will be at least 10% of that measured using the consensus RBS. In certain embodiments, an RBS that supports translation at a level of at least 1%, 5%, 10%, 20%, 30%, 40%, 50%, 60%, 70%, 80%, 90%, or more relative to the level at which the consensus RBS supports translation is used. In certain embodiments of the invention an RBS that supports translation at higher levels than the consensus RBS is used.

Further general teachings relating to riboregulators are found in published PCT application WO 2004/046321, the entire contents of which are incorporated by reference herein.

Advantages of Toehold and Beacon Riboregulators

Riboregulators of the invention offer a number of benefits compared to existing techniques. For instance, quantitative real-time PCR (qRT-PCR) offers highly sensitive detection of RNA levels, northern blots exhibit high specificity, and microarrays enable simultaneous detection of thousands of targets. However, in all these techniques, cells must be sacrificed to obtain the RNA for quantitation and thus it is challenging to measure RNA levels in real time. Fluorescence in situ hybridization (FISH) and the use of fluorescent RNA aptamers enable visualization of RNA localization inside cells. FISH requires cells to be fixed for visualization and hybridization takes a number of hours using expensive probes. RNA aptamers can be used to image RNA in living cells; however, those aptamers with the highest fluorescence intensity still require copy numbers far exceeding those of endogenous RNAs in order to be detected in most optical microscopes. RNA levels can also be measured using a fluorescent reporter protein driven from the same promoter as the RNA target. The reporter in this method can reflect the level of RNA target, yet it cannot recapitulate regulatory behavior from chromosomal regions distant (e.g. multiple kilobases) from the promoter region. Furthermore, the presence of additional copies of the promoter can titrate RNA polymerase activity away from the target gene. Lastly, RNAs tagged with protein binding aptamers have also been used to measure localization and levels of RNAs inside cells using fusions of the binding protein with fluorescent protein reporters. This technique, however, requires chromosomal modifications to either tag or knockout the gene corresponding to the RNA to be visualized. The riboregulators of the invention are not encumbered by these various limitations of the prior art techniques.

EXAMPLES

Example 1

Toehold Riboregulator and Reporter Protein/GOI

An exemplary riboregulator of FIG. 1 was tested experimentally. The GOI was an EGFP variant GFPmut3b, which was tagged with an ASV degradation signal to set its half-life to approximately 110 minutes. taRNAs cognate to the crRNA were designed using the software package NUPACK to have minimal secondary structure and perfect complementarity to the 30-nt long target binding site of the crRNA.

The riboregulator was tested in *E. coli* BL21 DE3 star, an RNase E deficient strain that contained a lambda phage lysogen bearing T7 RNA polymerase under the control of the IPTG inducible lacUV5 promoter. crRNA and taRNA constructs were expressed from separate plasmids to enable rapid characterization of the interaction of the crRNA with cognate and non-cognate taRNA sequences. For both the crRNA and the taRNA, transcription was initiated from an upstream T7 promoter and transcription terminated using a T7 RNA polymerase termination signal. The crRNA-GFP transcripts were generated from a plasmid with a medium copy number colA origin, while the taRNAs transcripts were generated from a higher copy number plasmid with a colE1 origin. These variations in plasmid copy number led to an estimated 7-fold excess of taRNA compared to crRNAs inside fully-induced cells. This ratio is similar to previous studies and typical copy number differences observed for anti-sense RNAs and their targets.

In vivo testing was performed in *E. coli* transformed with either a crRNA and its cognate taRNA target (ON state strains) or a crRNA and a non-cognate taRNA (OFF state strains) and grown overnight in 1 mL of selective LB media at 37° C. in deep well 96-well plates covered with a gas permeable seal. Transformation of *E. coli* with two plasmids in both ON and OFF state riboregulator conditions ensured that both strains were subject to similar metabolic loads, at least with respect to the number of exogenous RNAs that were being transcribed. Overnight cultures were diluted 100-fold and grown up for 80 minutes at 37° C. in the deep well plates. The early log phase cells were then induced with 0.1 mM of IPTG with aliquots taken at 1 hour time points for characterization via flow cytometry. For comparison of GFP fluorescence intensity between samples, the mode GFP intensity was calculated from fluorescence intensity histograms generate from flow cytometry data.

Figure 2:
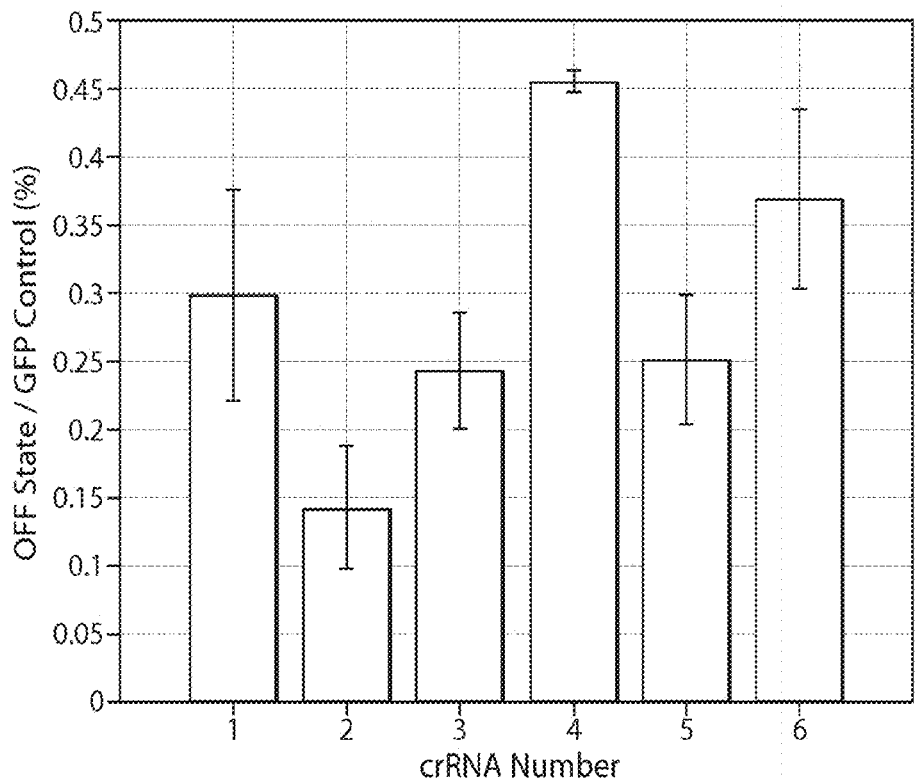
FIG. 2. Characterization of the repression level of six inactivated toehold riboregulator crRNAs.

As a first measure of riboregulator performance, the fluorescence intensity of the crRNA-GFP constructs was compared to the fluorescence from a non-cis-repressed GFP construct induced at the same level of IPTG in the same BL21 DE3 star *E. coli* strain. These measurements demonstrated extremely high levels of translational repression with six tested riboregulator crRNAs reducing fluorescence output by 99.5% or more (see FIG. 2). To calculate the effectiveness of the trans-activation of the riboregulator, mode GFP fluorescence of the crRNA-GFP in the presence of its cognate taRNA was compared to the fluorescence of the crRNA-GFP in the presence of a non-cognate taRNA. By dividing these two numbers, the on/off ratio was calculated for all the riboregulators tested. FIG. 3 presents this on/off ratio taken at one hour time points for a high performance toehold riboregulator. Error bars are the standard deviation in the on/off ratio calculated from three biological replicates. From these data, it is clear that the toehold riboregulator can display strong trans-activation by a target RNA, with fluorescence increasing by a factor of over 200 only two to three hours after induction.

Figure 4:
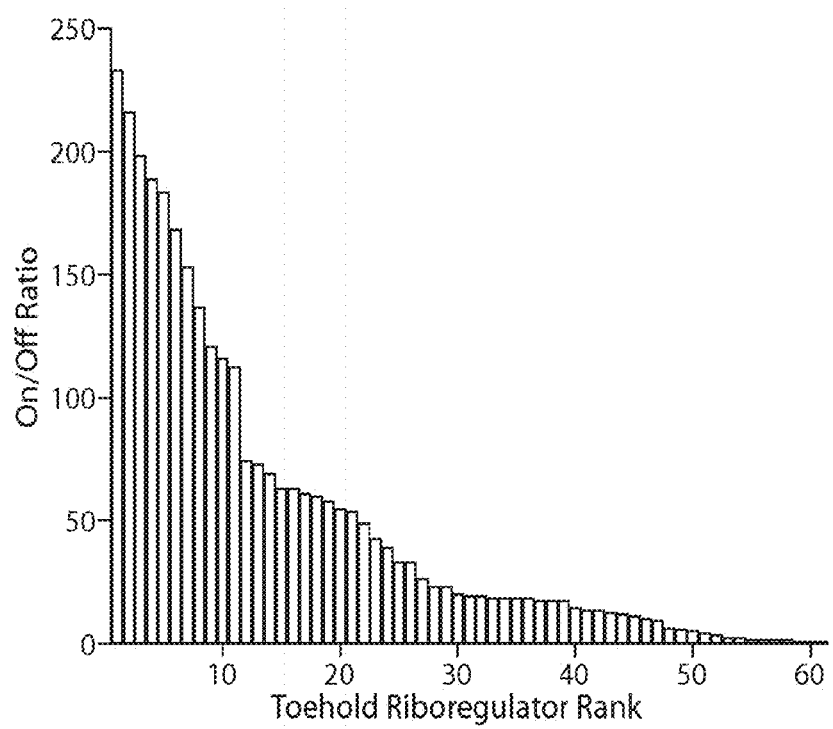
FIG. 4. On/off mode fluorescence ratios obtained for a set of 61 toehold riboregulators three hours after induction with IPTG.

The same measurements were performed in vivo on an additional 60 toehold riboregulator designs and the on/off ratios are displayed in FIG. 4. Roughly one third of the riboregulators tested increase GFP output by a factor of 50 or more in the presence of their cognate target.

Example 2

Beacon Riboregulators

Beacon riboregulators, such as those having a structure shown in FIG. 5, were tested using identical conditions to those used for the toehold riboregulators. FIG. 6 shows the on/off median fluorescence intensity ratios obtained for six beacon riboregulators. Four of the devices show on/off ratios exceeding ten with one design exceeding a factor of 200.

Example 3

Endogenous RNA Sensing

The novel riboregulators described herein can be used for the detection of endogenous RNAs. As a proof of concept, a beacon riboregulator was designed and generated that could be triggered by the small RNA ryhB in *E. coli*. RyhB is a 90-nt long non-coding RNA that is upregulated when iron levels are low in *E. coli*. This RNA can be induced through the addition of the iron chelator 2,2'-dipyridyl to the culture medium.

Figure 7:
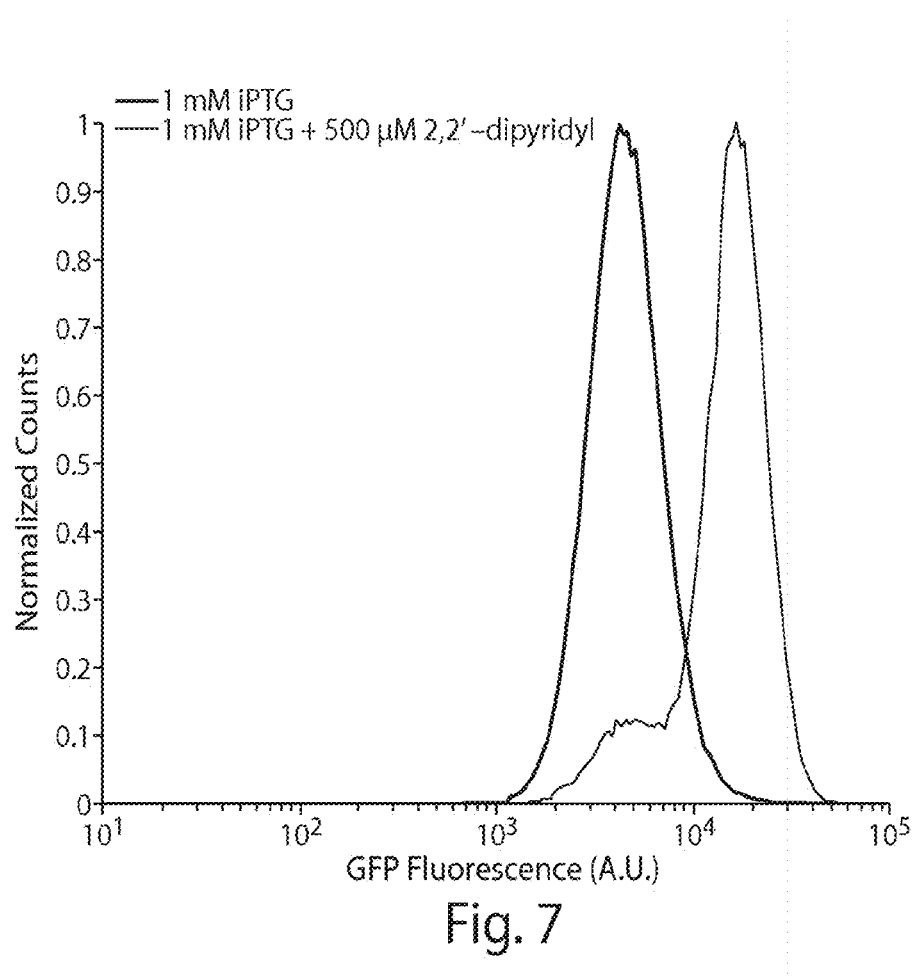
FIG. 7. Response of a beacon riboregulator targeting the small RNA ryhB. The riboregulator sensor was induced using 1 mM IPTG and ryhB was induced using 0.5 mM 2,2'-dipyridyl. The riboregulator sensor responded to increased intracellular ryhB levels by increasing output of GFP by a factor ~5.

To test this endogenous sensor, a plasmid was constructed that contained the beacon riboregulator upstream of a GFP reporter. Expression of the crRNA transcript was controlled using the IPTG-inducible PllacO-1 promoter. MG1655 *E. coli* cells transformed with the riboregulator sensor plasmid were induced with 1 mM IPTG in early log phase. At the same time, ryhB expression was induced through the addition of the iron chelator. Flow cytometry measurements taken from cells harvested after 2 hours demonstrated a five-fold increase in GFP fluorescence intensity for the ryhB containing cells compared to a control population that was not induced with 2,2'-dipyridyl (FIG. 7). In addition, control cells containing a non-cis-repressed GFP reporter under the PllacO-1 promoter exhibited a decrease in fluorescence intensity when induced with both IPTG and 2,2'-dipyridyl compared to those induced with IPTG alone. This additional control demonstrates that GFP output from the sensor was not caused by an increase in transcription levels caused by the addition of the iron chelator.

Example 4

Genetic Encoding of Complex OR Logic Operations Using Riboregulators

Figure 11A:
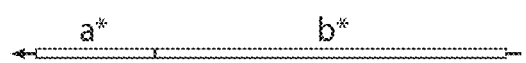
FIG. 11. Implementation of 2-input OR logic in vivo using riboregulators. (a) Three programmed RNA strands in the system. (b) Schematic of OR gate activation in vivo. (c) Flow cytometry measurements of on/off fluorescence from GFP upon transcription of different input RNAs to the system. In the off case, a non-cognate taRNA to the gate is expressed.
Figure 11A:
Figure 11A:
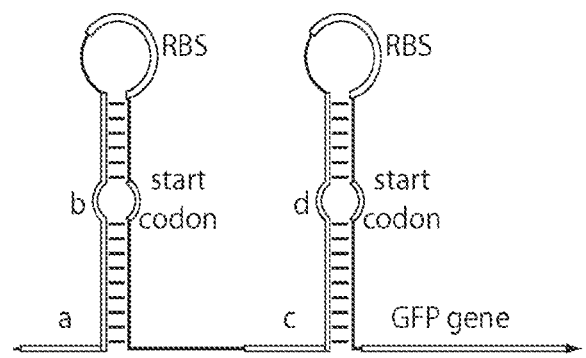
Figure 11B:
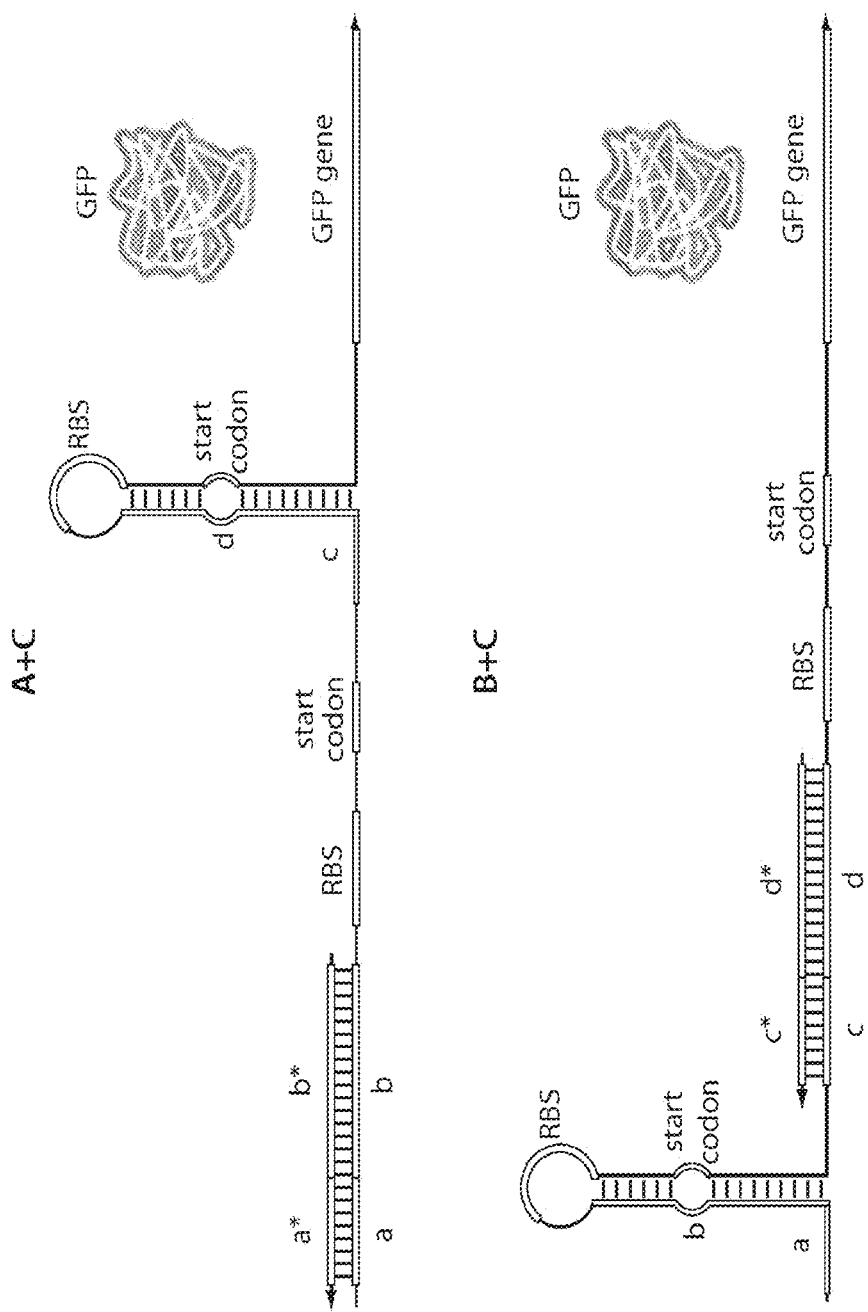
Figure 11C:
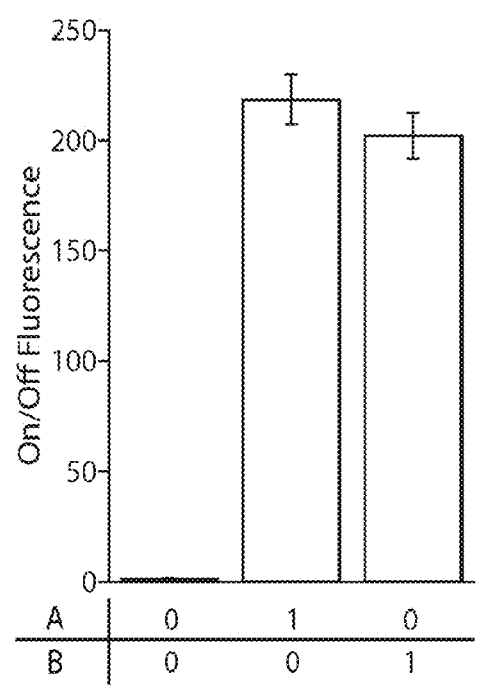

We have used members of the riboregulator library to successfully carry out multiple logical OR operations in vivo. The simplest OR operation involves two inputs, A and B, that activate a logic gate if either of the inputs is present. We implemented this system in vivo simply by taking two high performance riboregulators and placing them one after the other along the same mRNA upstream of the coding sequence for GFP (FIG. 11a). The intended operation of this gate in vivo is shown in FIG. 11b. When either input RNA molecule is present in the cell, it will bind to its corresponding crRNA module and de-repress the module by unwinding its stem. Since a ribosome engaged in protein translation has strong RNA helicase activity, it can unwind downstream crRNAs in its path, continuing translation unimpeded. Flow cytometry of the 2-input OR gate revealed strong activation of GFP expression when either programmed taRNA input was transcribed (FIG. 11c). In addition, parallel experiments in which the positions of the crRNAs were interchanged showed similar system performance.

Motivated by the successful implementation of the 2-input gate, we pursued a 6-input OR logic system featuring six crRNA modules placed upstream of GFP (FIG. 12). Since three of the parent crRNAs in the OR logic system contained stop codons, we modified their sequences to eliminate these unwanted codons and tested them individually to ensure the stop-codon-free variants retained the activities of their parents. Following these tests, the 474-bp six-crRNA construct was synthesized using gene assembly and transformed into E. coli along with plasmids expressing different taRNA elements. Cells expressing both the 6-input OR mRNA and one of the cognate taRNAs exhibit strong GFP fluorescence when measured on plates containing the inducer IPTG. A set of 4 non-cognate taRNAs, however, did not activate significant expression of GFP, highlighting the impressive orthogonality of our in vivo logic framework. Flow cytometry measurements from these transformants also confirmed successful OR gate operation, with all six inputs providing at least 5-fold higher GFP output compared to the set of 4 non-cognate taRNAs.

Example 5

Genetic Encoding of Complex AND Logic Operations Using Riboregulators

We have developed generalizable systems for carrying out AND logic operations using toehold riboregulators. FIG. 9 depicts a two input AND gate that features a crRNA sequence upstream of a GFP reporter sequence. The two inputs in the system are two RNA sequences A and B that contain one half of the cognate taRNA sequence of the crRNA gate (FIG. 9A). The two input RNAs also possess a hybridization domain (u-u*) that enables both RNAs to bind to one another when they are present inside the cell. When this hybridization event occurs, the two halves of the taRNA are brought into close proximity providing a sequence capable of unwinding the gate crRNA to trigger translation of GFP. Each of the input RNAs when expressed on its own is unable to derepress that crRNA since they are either: (1) unable to unwind a long enough region of the crRNA stem, which is the case for input B, or (2) they are kinetically and thermodynamically disfavored from binding to the crRNA, which is the case for input A. Flow cytometry measurements for the 2-input AND logic system validate its operation in E. coli (FIG. 9B). GFP output is activated only if all three RNAs in the system are expressed inside the cell, while it is low in all other cases.

Figures 13A, 13B:
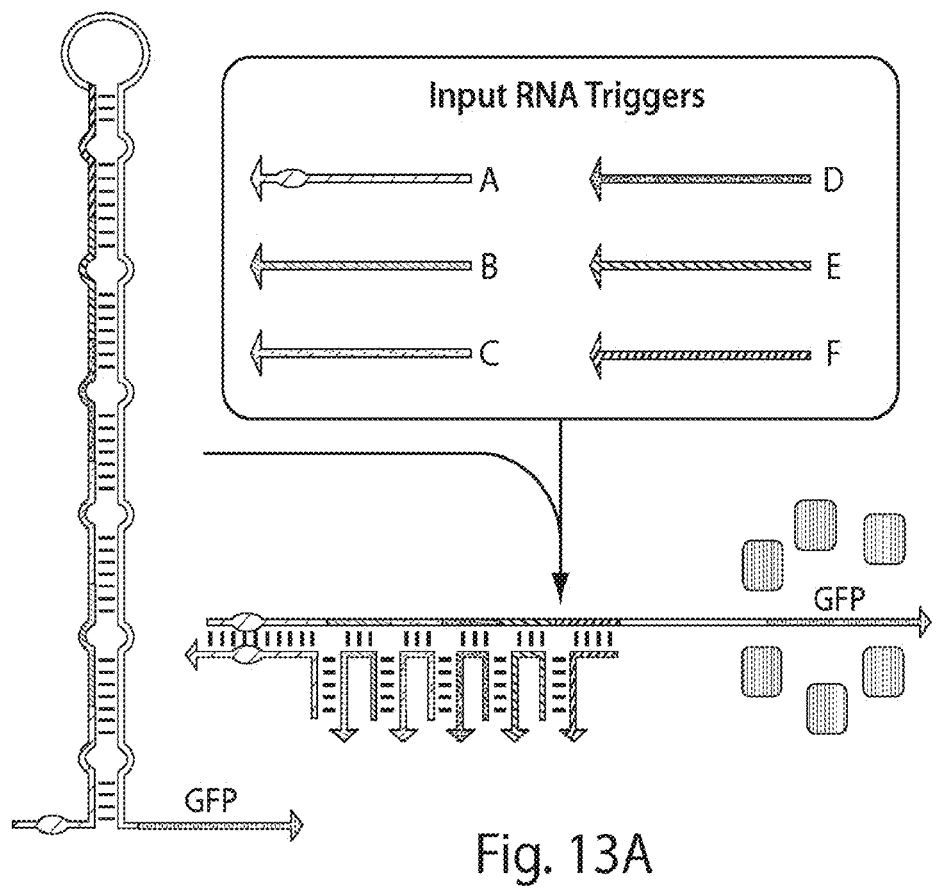
FIG. 13. (A) Schematic illustration of the six-input AND gate system. The gate consists of an extended hairpin containing sequences from validated toehold riboregulator crRNAs. The six input RNA triggers contain sequences from the corresponding taRNAs and hybridization domains for binding to neighboring input strands. (B) Images of GFP fluorescence from E. coli colonies for the 6-bit AND gate exposed to the specified combinations of inputs A through F. Strong GFP expression is observed only when all six inputs are present, as shown in the far right column.

AND gates based on toehold riboregulators have been successfully extended to 6-bit operation. As shown in FIG. 13A, the gate in this system consists of a hairpin with an extended stem consisting of the stem sequences of six validated toehold riboregulator crRNAs and a toehold sequence from the bottommost crRNA. The input RNAs thus contain the corresponding taRNA sequences and also possess hybridization sequences to their neighboring input strands. The hybridization sequence of a given input is complementary to the toehold binding domain of the next input RNA. For example, input A contains a 12- to 15-nt sequence to which input B binds, and this sequence is the toehold for the cognate crRNA of input B. Consequently, binding of input A to the gate unwinds the bottom bases of its stem, and also provides a new toehold for binding of input B. This stem unwinding/toehold presentation process repeats until all inputs are bound to the gate. Upon binding of all inputs, the RBS and start codon are de-repressed thereby triggering production of GFP or another protein of interest. We have validated this gate by expressing different combinations of the input RNAs in E. coli also expressing the gate mRNA. FIG. 13B shows GFP intensities measured from colonies induced on LB plates. Strong GFP fluorescence is only visible when all six inputs are expressed in the cell. GFP expression is low in the six other input combinations, including stringent tests where all but one of the input RNAs is expressed.

Example 6

Riboregulator Toehold Repressors

We constructed a library of 44 toehold repressors (devices/systems) and tested their function in E. coli BL21 Star DE3. We used flow cytometry to test the performance of the systems, calculating the mode GFP fluorescence from the switch in its OFF state (i.e., in the presence of its cognate trigger); and in its ON state (i.e., in the absence of its cognate trigger). We then calculated percent repression levels using the equation:

% repression=1−[OFF state mode fluorescence÷ON state mode fluorescence].

Figure 16:
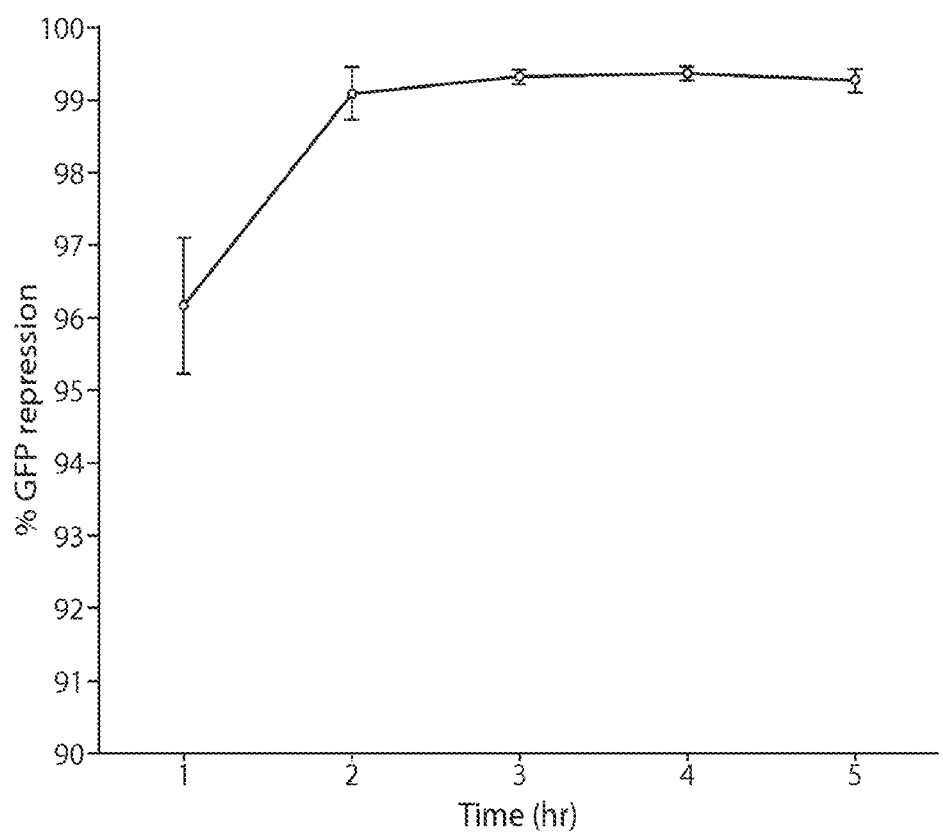
FIG. 16. Time course measurements for a high performance toehold repressor. Measurements were taken at hour time points following addition of the inducer IPTG.

FIG. 15B displays the % repression levels obtained for the 44 repressors in the library. Repressors 40 to 44 have highly variable performance. We postulate that their behavior is due to instability of the folding of the switch RNA, which causes fluctuations between the ON and the OFF state configurations of the switch RNA even when the trigger RNA is not present. The rest of the devices/systems perform quite well on average. 73% of the total library has repression levels of at least 80%. Moreover, 50% of the library exhibits repression of greater than 90%. This impressive 90% repression level exceeds the performance of almost all previously reported translational repressors (see Mutalik et al., Nat. Chem. Biol. 8:447-454, 2012). Additional measurements also demonstrated that the highest performance toehold switches could achieve translational repression greater than 95% within 1 hour and increase the level to above 99% in subsequent time points (FIG. 16).

Example 7

Toehold Switches

As described herein, the invention provides a new class of post-transcriptional riboregulators of gene expression in called toehold switches that have no known natural counterparts. Toehold switches activate expression of a regulated gene in response to a trans-acting trigger RNA. Their operation in living cells is facilitated by two novel mechanisms: toehold-based linear-linear RNA interactions pioneered in in vitro studies and efficient translational repression via base pairing in regions surrounding the initiation codon. We demonstrate that toehold switches routinely enable modulation of protein expression by over 100 fold, with the best switches rivaling the dynamic range of protein-based regulators. We validate large sets of orthogonal components, including a library of 18 toehold switches exhibiting system cross talk levels below 2%, which constitutes the largest and most stringent family of orthogonal regulatory elements, protein or RNA based, ever reported. We then forward engineered a set of 13 toehold switches with an average on/off fluorescence ratio of 406. We further applied thermodynamic analyses to predict variations in system performance. Furthermore, we demonstrate a set of toehold switches that are capable of effective triggering from functional mRNA molecules. The high dynamic range, orthogonality, programmability, and versatility of these toehold switches suggest they will be powerful new tools for synthetic biology.

Methods

Strains, plasmids, and growth conditions. The following E. coli strains were used in this study: BL21 Star DE3 (F$^-$ ompT hsdS$_B$ (r$_B^-$m$_B^-$) gal dcm rne131 (DE3); Invitrogen), BL21 DE3 (F$^-$ ompT hsdS$_B$ (r$_B^-$m$_B^-$) gal dcm (DE3); Invitrogen), MG1655Pro (F$^-$ λ$^-$ilvG-rfb-50 rph-1 Sp$^R$ lacR tetR), and DH5a (endA1 recA1 gyrA96 thi-1 glnV44 relA1 hsdR17(r$_K^-$m$_K^+$) λ$^-$). All strains were grown in LB medium with appropriate antibiotics. Antibiotics were used at the following concentrations: ampicillin (50 µg mL$^{-1}$), kanamycin (30 µg mL$^{-1}$), and chloramphenicol (34 µg mL$^{-1}$).

To characterize the toehold switches, chemically competent E. coli were transformed with the desired combination of toehold switch and trigger plasmids, and spread onto LB/agar plates containing the appropriate pair of antibiotics. For colony GFP fluorescence measurements, LB/agar plates were supplemented with 0.1 mM isopropyl β-D-1-thiogalactopyranoside (IPTG) to induce RNA expression. For flow cytometry measurements, LB medium containing antibiotics was inoculated with cells picked from individual colonies and incubated overnight with shaking at 37° C. Cells were then diluted 100-fold into fresh selective LB medium and returned to shaking at 37° C. in 96-well plates. For T7 RNA polymerase driven expression in BL21 Star DE3 and BL21 DE3, cells were induced with 0.1 mM IPTG at 0.2-0.3 OD600 after 80 minutes of growth. Unless otherwise noted, measurements on cell cultures were taken 3 hours after addition of IPTG. For expression using the constitutive PN25 promoter, overnight cultures were diluted 100-fold into selective LB media. The time of this dilution was defined as t=0 for subsequent measurements.

Plasmid Construction.

All DNA oligonucleotides were purchased from Integrated DNA Technologies, Inc. Double-stranded trigger and switch DNA was produced from either single >100-nt oligonucleotides amplified using universal primers or using gene assembly from short <50-nt oligonucleotides segmented using gene2oligo (Rouillard et al., Nucleic Acids Res 32:W176-180, 2004). These PCR products were then inserted into vector backbones using Gibson assembly with 30-bp overlap regions (Gibson et al., Nat. Methods 6:343-345, 2009). Vector backbones were PCR amplified using the universal backbone primers and digested prior to assembly using DpnI (New England Biolabs, Inc.). Backbones were generated from the T7-based expression plasmids pET15b, pCOLADuet, and pACYCDuet (EMD Millipore). pET15b, pCOLADuet, and pACYCDuet plasmids all contain a constitutively expressed lad gene, a T7 RNA polymerase promoter and terminator pair, and the following respective resistance markers/replication origins: ampicillin/ColE1, kanamycin/ColA, and chloramphenicol/P15A. All trigger RNAs presented herein were expressed using pET15b backbones, and the switch mRNAs were expressed using either pCOLADuet or pACYCDuet backbones. Reverse primers for the backbones were designed to bind to the region upstream of the T7 promoter. Forward primers for trigger backbones amplified from the beginning of the T7 promoter. Forward primers for the switch backbones were designed to prime off the 5' end of either GFPmut3b-ASV or mCherry and add a 30-nt sequence containing the linker for Gibson assembly. Constructs were cloned inside DH5a and sequenced to ensure all toehold switch components were synthesized correctly. All transformations were performed using established chemical transformation protocols (Inoue et al., Gene, 96:23-28, 1990).

Flow Cytometry Measurements and Analysis.

Flow cytometry was performed using a BD LSRFortessa cell analyzer equipped with a high throughput sampler. GFP fluorescence intensities were measured using 488 nm excitation laser and a 530/30 nm filter. mCherry fluorescence intensities were measured using a 561 nm laser and a 610/20 nm emission filter. In a typical experiment, cells were diluted by a factor of ~65 into phosphate buffered saline (PBS) and sampled from 96-well plates. Forward scatter (FSC) was used for trigger and ~30,000 individual cells analyzed.

Error levels for the fluorescence measurements of on state and off state cells were calculated from the standard deviation of measurements from at least three biological replicates. The relative error levels for the on/off fluorescence ratios were then determined by adding the relative errors of on and off state fluorescence in quadrature. For measurements of in vivo system cross talk, single colonies of each of the 676 strains of transformed cells were measured using flow cytometry. To estimate colony-to-colony variations in GFP output for these strains, we measured a randomly selected subset of 18 transformants and measured them in sextuplicate. The relative uncertainties for these measurements was 12% on average, which is comparable to uncertainties obtained for flow cytometry experiments used for determining on/off fluorescence ratios for library components.

Colony Fluorescence Imaging.

Images of fluorescence from E. coli colonies were obtained using a Typhoon FLA 9000 biomolecular imaging system. All images were obtained using the same PMT voltage, an imaging resolution of 0.1 mm, 473 nm laser excitation, and an LPB (>510 nm long pass) filter for detection of GFP. Induced cells were imaged ~18 hours after they were plated. Since IPTG exhibits low-level fluorescence in the same channel as GFP, variations in the thickness of the LB/agar in the plates result in variations in background fluorescence levels. To compensate for this effect, the minimum GFP intensity measured over each plate was subtracted from the intensity levels of the entire plate, thereby removing most background IPTG fluorescence.

Results

Provided herein is a new system of riboregulators that enable post-transcriptional activation of protein translation. Unlike conventional riboregulators, the synthetic riboregulators of the invention take advantage of toehold-mediated linear-linear interactions to initiate RNA-RNA strand displacement interactions. Furthermore, they rely on sequestration of the region around the start codon to repress protein translation, eschewing any base pairing to the RBS or start codon itself to frustrate translation. As a result, these riboregulators can be designed to activate protein translation in response to a trigger RNA with virtually arbitrary sequence, enabling substantial improvements in component orthogonality. The absence of binding to the RBS and use of thermodynamically favorable linear-linear interactions also enables facile tuning of translational efficiency via RBS engineering. Consequently, these systems routinely enable modulation of protein expression over two orders of magnitude. Based on their interaction mechanism near-digital signal processing behavior, these riboregulator systems are referred to herein as toehold switches.

This disclosure further demonstrates the utility of toehold switches by validating dozens of translational activators in E. coli that increase protein production by more than 100-fold in response to a prescribed trigger RNA. Furthermore, we capitalize on the expanded RNA sequence space afforded by the novel riboregulator design to construct libraries of components with unprecedented part orthogonality, including a set of 26 systems that exhibit less than 12% cross talk across the entire set, which exceeds the size of all previous orthogonal regulator libraries by a factor of more than 3. Sequence and thermodynamic analyses of the toehold switches yield a set of design principles that can be used to forward engineer new riboregulators. These forward engineered parts on average exhibit on/off ratios exceeding 400, a dynamic range typically reserved for protein-based genetic networks using components constructed from a purely rational design framework.

Toehold Switch Design.

Figure 17A:
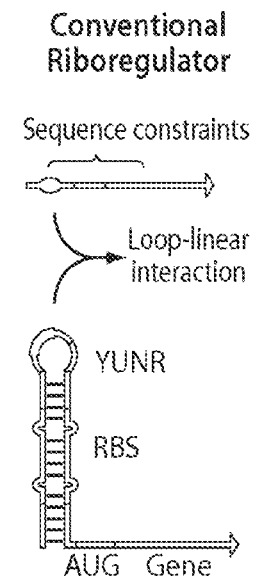
FIG. 17. Toehold switch design and output characteristics. (A) Conventional riboregulator systems repress translation by base pairing directly to the RBS region. RNA-RNA interactions are initiated via a loop-linear interaction at the YUNR-loop in an RNA hairpin. Interaction initiation region is denoted by thicker lines. (B) Toehold switches repress translation through base pairs programmed before and after the start codon AUG, leaving the RBS and start codon regions completely unpaired. RNA-RNA interactions are initiated via linear-linear interaction domains called toeholds. The toehold domain (a*) binds to a complementary a domain on the trigger RNA. The ensuing branch migration de-represses the toehold switch mRNA to enable translation of the downstream gene. (C) GFP mode fluorescence levels measured for switches in their on and off states as well as positive controls in which GFP with an identical sequence is expressed. Dashed black line marks the background fluorescence level obtained from IPTG-induced cells not bearing a GFP expressing plasmid. (D) On/off GFP fluorescence levels obtained for a set of 168 toehold switches with 20 displaying on/off ≥100. Inset: On/off GFP fluorescence measured for four toehold switches of varying performance levels at different time points following induction with IPTG.
Figure 17B:
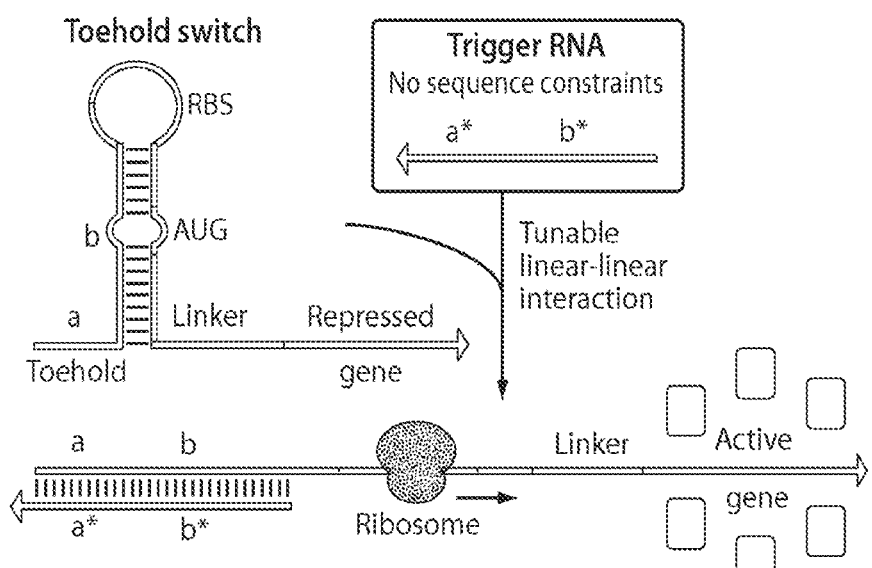

The toehold switch systems are composed of two programmed RNA strands referred to as the switch and trigger (FIG. 17B). The switch mRNA contains the coding sequence of a gene being regulated. Upstream of this coding sequence is a hairpin-based processing module containing both a strong ribosome binding site and a start codon followed by a short linker sequence coding for amino acids added to the N-terminus of the gene of interest. A single-stranded toehold sequence at the 5' end of the hairpin module provides the initial binding site for the trigger RNA strand. This trigger molecule is a single-stranded RNA that completes a branch migration process with the hairpin that exposes the RBS and initiation codon, thereby causing activation of translation of the gene of interest.

The hairpin processing unit functions as a repressor of translation in the absence of the trigger strand. Unlike previous riboregulators, the RBS sequence is left completely unpaired within the 11-nt loop of the hairpin. Instead, the bases immediately before and after the initiation codon are sequestered within RNA duplexes that are six and nine base pairs long, respectively. The start codon itself is left unpaired in the switches we tested, leaving a 3-nt bulge near the midpoint of the 18-nt hairpin stem. Since the repressing domain b (FIG. 17B) does not possess complementary bases to the start codon, the cognate trigger strand in turn does not need to contain corresponding start codon bases, thereby increasing the number of potential trigger sequences. The sequences of the hairpin sequence added after the start codon were also screened for the presence of stop codons, as they would prematurely terminate translation of the gene of interest when the riboregulator was activated. Studies of the GFP expression from the repressed toehold switch mRNA revealed typical repression levels of 98% or higher compared to unrepressed GFP mRNAs. After confirming successful translational repression with this design, we employed a 12-nt toehold domain at the 5' end of the hairpin to initiate its interaction with the cognate trigger strand. The trigger strand bears a 30-nt single-stranded RNA sequence that is perfectly complementary to early bases in the switch mRNA.

From this base toehold switch design, we used the NUPACK nucleic acid sequence design package (Zadeh et al., J. Comput. Chem. 32:170-173, 2011) to generate a library of translational activators. A common 21-nt sequence was used to link the hairpin module of the switch mRNAs to the coding sequence of the gene of interest. This linker sequence was programmed to encode low molecular weight amino acids to minimize its effect on folding of the gene of interest, which was selected in this case to be a GFP reporter. To reduce computational load, only the first 29-nts of GFP were considered for secondary structure analysis. The complete trigger transcript, however, was simulated during the design process. This transcript included a GGG leader sequence to promote efficient transcription from the T7 RNA polymerase promoter, a 5' hairpin domain to increase RNA stability, and the 47-nt T7 RNA polymerase terminator at the 3' end of the transcript. NUPACK was used to generate toehold switch designs satisfying the prescribed secondary structures and having the specified RBS and terminator sequences. Unspecified bases in the designs were random and thus allowed to become any of the four RNA bases, with some sequence constraints applied to NUPACK to preclude extended runs of the same bases. We initially designed a set of 24 toehold switches to gauge in vivo performance and constructed them as described in the Methods section. After confirming that a number of these switches exhibited high dynamic range, we began to design an extended library of toehold switches containing elements selected for low crosstalk with the rest of the library.

To generate this library, a total of 672 toehold switch designs with randomized sequences were generated using NUPACK. Of the resulting designs, 25 were found to encode stop codons in the hairpin region after the start codon. In the remaining systems, one duplicate design was found leaving 646 unique riboregulator designs in the library.

We next selected a subset of 144 of these toehold switch designs for testing in E. coli that exhibited the lowest levels of unintended riboregulator-trigger cross talk. In silico screening for cross talk served two purposes. First, the resulting library of orthogonal regulators could provide a large set of components to independently regulate translation in vivo. Second, systems screened for orthogonality would necessarily span a large portion of the sequence space of possible toehold switches and inform future system designs. We simulated pairwise interactions between riboregulator and trigger strands for the complete set of 646 corresponding to 417,316 RNA-RNA interactions. These simulations determined the concentration of any resulting riboregulator-trigger complexes and their secondary structures. The integrity of the toehold switch stem in these riboregulator-trigger complexes was used to determine the likelihood of unintended trigger activation, since the destruction of the duplex regions nearby the start codon would lead to translation of the gene of interest. Through this stem integrity metric, we used a Monte Carlo algorithm to select 144 toehold switch designs with the predicted lowest net system cross talk. This resulted in a toehold switch library composed of 168 different components with random sequences subject to the same secondary structure constraints.

Component Validation.

The toehold switches were tested in E. coli BL21 Star DE3 with the switch mRNA expressed off a medium copy plasmid (ColA origin) and the trigger RNA expressed from a high copy plasmid (ColE1 origin). Expression of both strands was induced using IPTG, which triggered production of both RNA species through T7 RNA polymerase. To enable quantitative assessment of switch performance, we used an ASV-tagged GFPmut3b with a reported half-life of 110 min (Andersen et al., Appl. Environ. Microbiol. 64:2240-2246, 1998) as a fluorescent reporter. In these experimental conditions, the copy number differences in the plasmids expressing switch and trigger RNAs led to a 6-8 fold excess of trigger compared to switch molecules as determined by fluorescence measurements of GFPmut3b-ASV expressed separately from each plasmid.

Figure 17C:
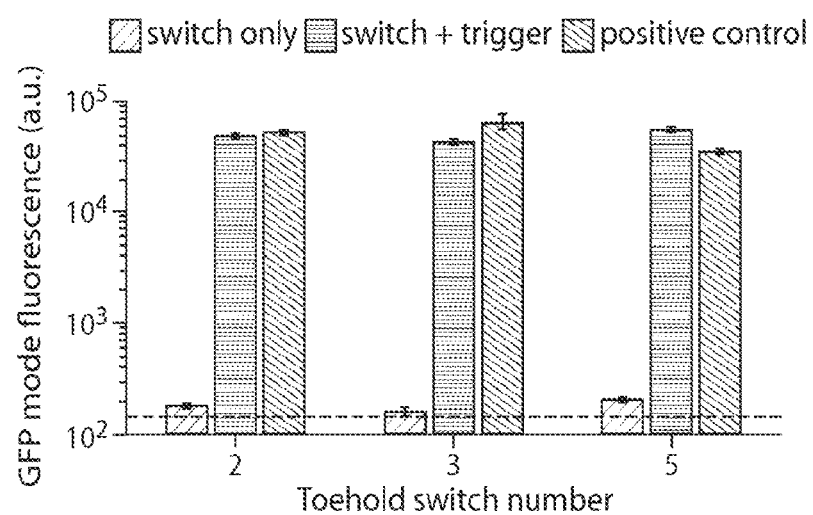

Flow cytometry was used to characterize the performance of the toehold switches. Cells were measured at one-hour intervals after induction with IPTG. ON fluorescence was measured for cells transformed with the riboregulator and its cognate trigger, while OFF fluorescence was determined from cells containing the riboregulator and a randomly selected non-cognate trigger. Fluorescence histograms from both activated and repressed toehold switches are almost exclusively unimodal, highlighting their potential use in cellular digital logic (data not shown). The mode fluorescence value from the histograms was used to calculate the on/off ratios of each riboregulator design. FIG. 17C displays the mode GFP fluorescence measured from three toehold switches (numbers 2, 3 and 5) in their on and off states (switch only is first bar, switch and trigger is second bar, and positive control is third bar). For comparison, unrepressed versions of each switch mRNA containing the same sequences for the GFP reporter were also evaluated as positive controls. The off state fluorescence of the switches is near the background fluorescence levels measured for induced cells not expressing GFP. On state fluorescence for the activated toehold switches was comparable to the positive controls, indicating that nearly all switch mRNAs were bound by their trigger RNAs.

Figure 17D:
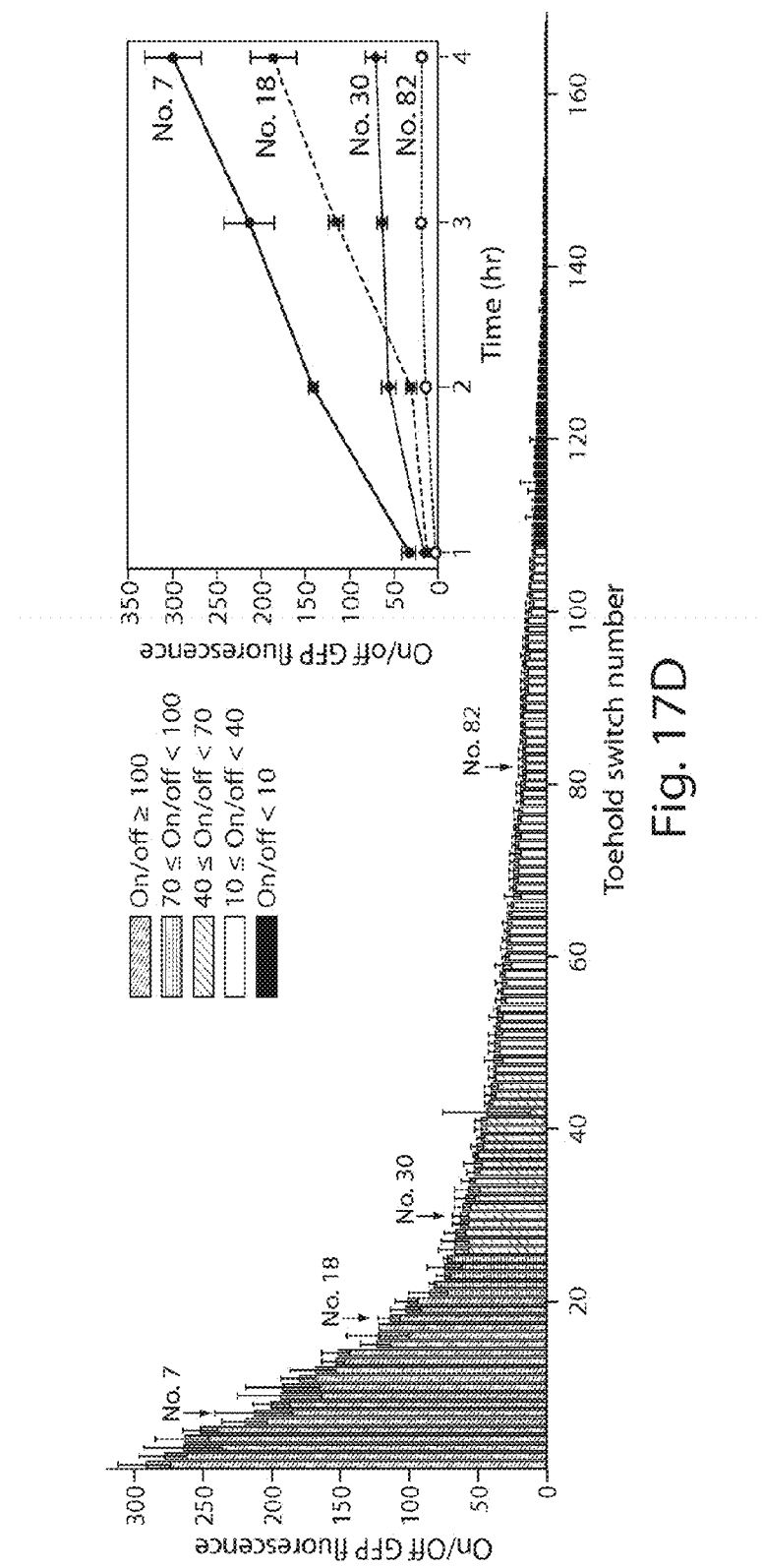

Activation of the systems was observed within one hour of induction and increased over time with accumulation of GFP (FIG. 17D, inset). FIG. 17D presents the on/off mode GFP fluorescence ratio determined three hours after induction for all 168 of the switches in the random sequence library. Of the systems tested, 20 exhibit on/off ratios exceeding 100 and nearly two thirds display at least an on/off greater than 10. In comparison, we also characterized the widely used engineered riboregulators crRNA 10 and 12 (described by Isaacs et al., Nat. Biotechnol. 22:841-847, 2004) in identical conditions. These earlier riboregulation systems exhibited significantly lower dynamic range with on/off values of 11±2 and 13±4 for crRNA systems 10 and 12, respectively.

Evaluation of Toehold Switch Orthogonality.

Figure 18A:
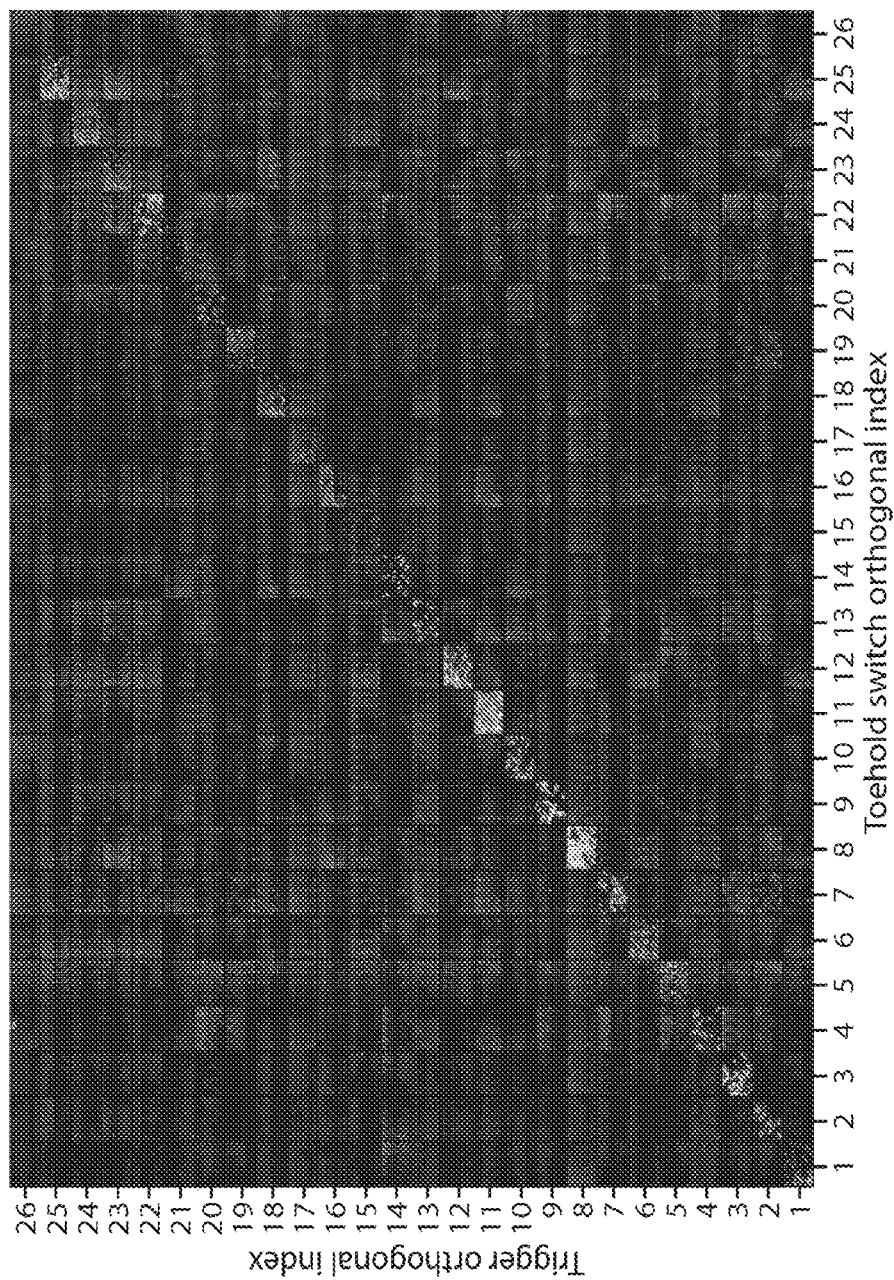
FIG. 18. Comprehensive assessment of toehold switch orthogonality. (A) GFP fluorescence from colonies of *E. coli* expressing 676 pairwise combinations of switch mRNAs and trigger RNAs. GFP expressing colonies are visible along the diagonal in cells containing cognate switch and trigger strands. Off diagonal components have low fluorescence as a result of minimal interaction between non-cognate RNA components. (B) Crosstalk measured by flow cytometry for all trigger-switch combinations confirming strong overall system orthogonality. (C) Comparison of orthogonal library dynamic range (reciprocal of the threshold crosstalk level) and orthogonal library size for the toehold switches and a number of previous RNA-based regulators.

To evaluate the orthogonality of the translational activators, we selected the top 35 riboregulators from the 144 orthogonal component library and performed additional in silico screening to isolate a subset of 26 that displayed extremely low levels of cross talk, both in terms of stem integrity and unwanted binding between non-cognate trigger and switch strands. The pairwise interactions between the 26 riboregulators were then assayed in $E.\ coli$ by transforming cells with all 676 combinations of riboregulator and trigger plasmids. FIG. 18A displays images of GFP fluorescence from colonies of $E.\ coli$ induced on LB plates. The set of orthogonal switches are shown in order of decreasing on/off fluorescence ratio measured in FIG. 17D. Clearly visible is the strong emission from cognate switch and trigger pairs along the diagonal of the grid with the final switch at index 26 displaying lower fluorescence as a result of its low on/off ratio. In contrast, low fluorescence levels are observed for the off-diagonal elements featuring non-cognate trigger/switch RNA pairs.

Figure 18B:
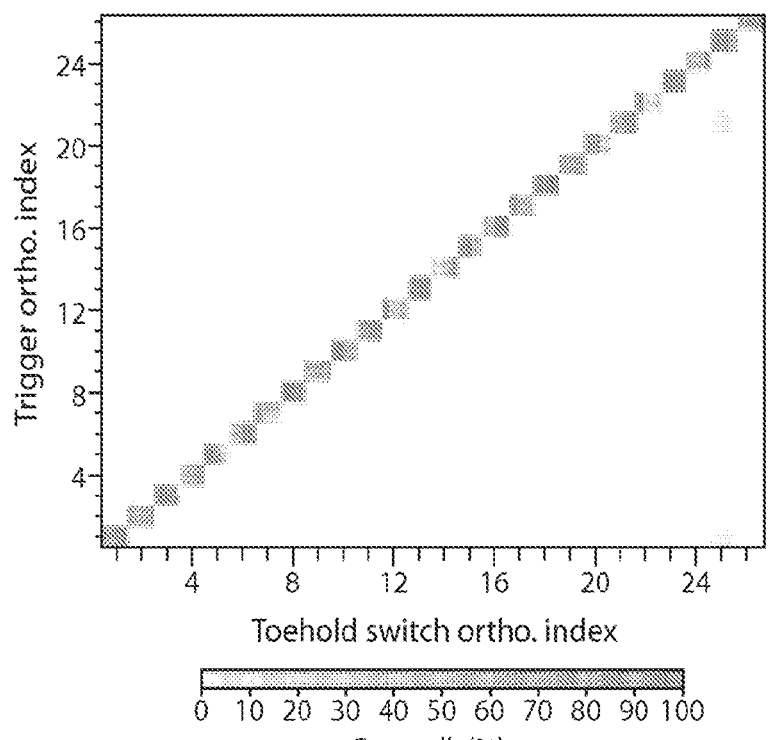

To gain quantitative information, we used flow cytometry to measure the GFP output from all pairwise trigger-switch interactions. Crosstalk was calculated by dividing the GFP fluorescence obtained from a non-cognate trigger and a given switch mRNA by the fluorescence of the switch in its triggered state. The resulting matrix of crosstalk interactions is shown in FIG. 18B. By definition, crosstalk levels along the diagonal are 100%, while those off the diagonal agree with the qualitative output levels from colony images. Based on these data, the toehold switches exhibit an unprecedented degree of orthogonality with the full set of 26 regulators tested displaying under 12% crosstalk. Since the number of regulators in an orthogonal set is defined by its threshold crosstalk level, we identified orthogonal subsets for a range of different crosstalk thresholds. For instance, a subset of 18 of the toehold switches exhibits less than 2% subset-wide crosstalk.

Figure 18C:
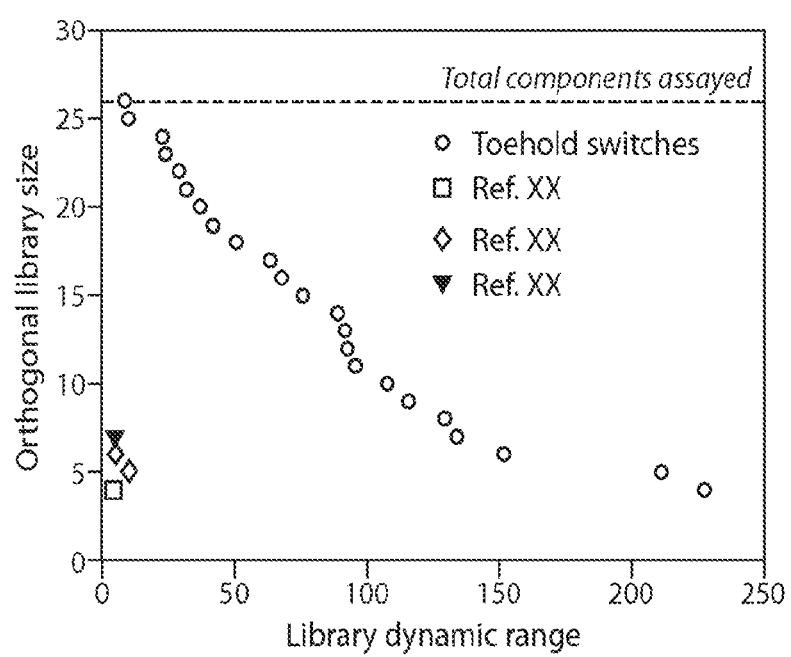

When choosing toehold switches for a given application, a potentially more relevant metric for assessing their performance is the reciprocal of the threshold crosstalk level. For translational activators, this parameter represents the minimum fold change to expect between when using the set of switches to regulate a protein with similar output characteristics to our GFPmut3b-ASV reporter. FIG. 18C plots this library dynamic range metric against the maximum orthogonal subset size for the toehold switches as a well as a number of other RNA-based regulators. The largest previously reported orthogonal riboregulator set consisted of seven transcriptional attenuators displaying 20% crosstalk (Takahashi et al., Nucleic Acids Res., 2013). For that library, 20% crosstalk results in an upper bound in its overall dynamic range of 5 (FIG. 18C). Earlier orthogonal translational activators and repressors have been limited to sets of four (Callura et al., Proc. Natl. Acad. Sci. USA 109: 5850-5855, 2012) and five (Mutalik et al., Nat. Chem. Biol. 8: 447-454, 2012), respectively, at 20% crosstalk. For proteins, an engineered library of five orthogonal eukaryotic transcription factors crosstalk of ~30% was also reported (Khalil et al., Cell 150:647-658, 2012). To our knowledge, the switches provided herein constitute the largest set of orthogonal regulatory elements, RNA- or protein-based, ever reported. Furthermore, subsets of orthogonal toehold switches of comparable size to previously reported libraries exhibit minimum dynamic ranges over an order of magnitude larger than previously reported systems.

Component Analysis and Forward Engineering.

Figure 19A:
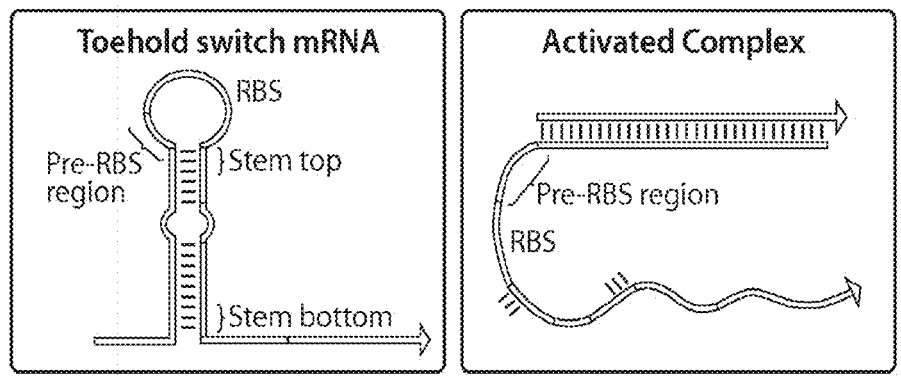
FIG. 19. Sequence analysis and forward engineering of toehold switches. (A) Regions and parameters critical to toehold switch output characteristics. (B) Evaluation of 168-member toehold switch library as a function of the number of G-C base pairs in the top and bottom three base pairs in the switch mRNA stem. Color of the background squares in the figure correspond to the mean on/off GFP fluorescence for the set of riboregulators that satisfy the specified GC base pairing constraints. Color of the circles within each square corresponds to the actual on/off ratio obtained for each of the components that satisfy the constraints. (C) On/off GFP fluorescence ratios obtained for the set of 13 forward engineered toehold switches. Dashed black line marks the mean on/off fluorescence level measured for the full set of 168 random sequence toehold switches. Inset. Time course measurements for forward engineered switches number 6 and number 9. (D) Percentage of random sequence and forward engineered library components that had on/off ratios that exceeded a specific value.
Figure 19B:
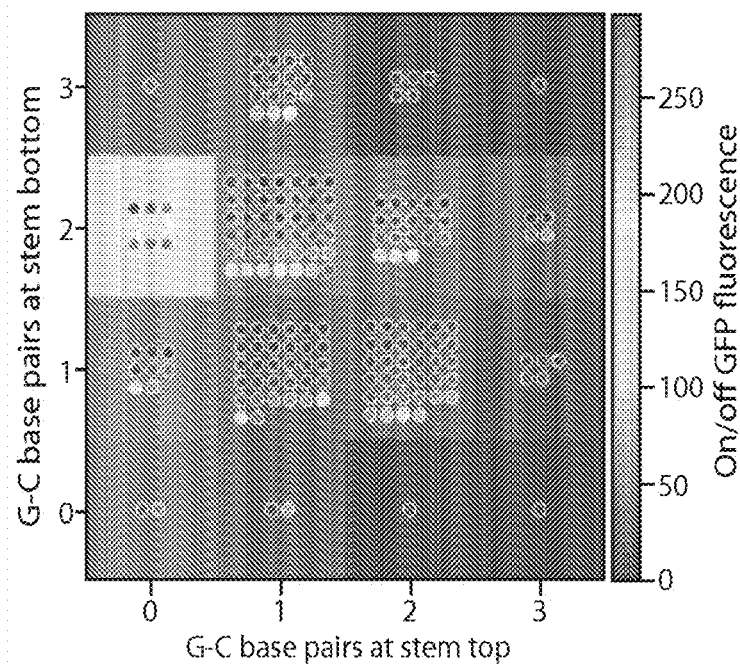

Flow cytometry data from the toehold switches provided a substantial dataset with which to determine sequence-dependent variations in riboregulator performance. As a coarse screen for sequence-dependent effects, we began to investigate toehold switch output as a function of base pairing at the top and bottom in the stem of the riboregulator strand (FIG. 19A). We hypothesized that the strength of the base pairing in these regions would have a strong effect on the repression strength of the hairpin as they are essential to sequestering the start codon, and they could also affect the secondary structure of the RBS and mRNA region once the riboregulator is activated, which in turn influences translational efficiency (Kudla et al., Science 324:255-258, 2009). Analysis of the top and bottom three base pairs in the hairpin module revealed significant variations in the on/off ratio of riboregulators as a function of the G-C base pair content in these regions. FIG. 19B displays the average on/off fluorescence obtained for all 16 possible permutations of G-C content in the two stem regions, as well as the on/off values obtained for each toehold switch that satisfied the specified G-C conditions. Based on the size of the library and secondary structure constraints imposed during in silico design, a number of G-C permutations had only one or two representative toehold switches. Toehold switches containing zero and two G-C base pairs at the top and bottom regions of the stem, respectively, displayed an average on/off fluorescence ratio of 154, over three times higher than the next highest permutation. Mean on/off levels also tended to steadily decrease as G-C combinations deviated further from this combination.

The bias toward low G-C content at the top of the riboregulator stem suggested potential interaction between the bound ribosome and the nearby RNA duplex in the activated riboregulator-trigger complex. In particular, weak base pairing at the end of the RNA duplex could allow the duplex to breathe open, spontaneously freeing bases upstream of the RBS to facilitate ribosome binding. To investigate this effect, we studied a series of riboregulators with different hairpin loop sizes to tune the size of the pre-RBS region (FIG. 19A), defined as the nucleotides between the RNA duplex and the start of the RBS sequence. Measurements of the loop variant riboregulators demonstrated steady increases in the on state fluorescence output as the pre-RBS region was increased from 3- to 19-nts in size through the addition of an A-rich sequence (data not shown). Notably, these increases in on state expression did not result in corresponding increases in system off state until the pre-RBS sequence was 13-nts in length, which corresponded to a loop of 21-nts. These observations are consistent with previous studies that demonstrated translational enhancement through A/U bases placed immediately upstream of the RBS (Vimberg et al., BMC Mol. Biol. 8:1-13, 2007). Furthermore, they provided a straightforward means of increasing toehold switch dynamic range by increasing the length of its hairpin loop. Systematic studies of toehold switch behavior as a function of trigger RNA length were also conducted. These studies revealed a strong positive correlation between system on/off ratios and the length of the toehold domain (data not shown) and demonstrated that switch output could be increased by only partially unwinding the stem of the switch (data not shown).

Previous riboregulators have been designed on a case-by-case basis (Isaacs et al., Nat. Biotechnol. 22:841-847, 2004; and Callura et al., Proc. Natl. Acad. Sci. USA 109:5850-5855, 2012) and those that have utilized computer-assisted design have not demonstrated consistently high on/off levels (Rodrigo et al., Proc. Natl. Acad. Sci. USA 109:15271-15276, 2012). In silico designed riboregulators forward engineered to exhibit high performance in vivo have the potential to significantly reduce the time required for generating new genetic circuits, in turn enabling the realization of more complex cellular logic. Consequently, we integrated the above findings into designs for a set of toehold switches forward engineered for high dynamic range. Our forward engineered systems retain the same general secondary structure and interaction mechanisms of the library of 168 toehold switches, but adopt several of the insights described above to significantly improve their dynamic range. First, we incorporated the combination of switch mRNA sequence constraints revealed in FIG. 19B. Specifically, the top three bases of the hairpin stem were restricted to weak A-U base pairs. The bottom three base pairs of the stem were specified to contain two strong G-C base pairs and one A-U base pair. Second, we increased the length of the switch toehold from 12- to 15-nts. This change strengthened the initial binding between the trigger and the switch. Third, we increased the size of the hairpin loop from 11- to 15-nts to enhance translation of the output protein upon switch activation. We selected a fairly conservative loop size of 15-nts to ensure that leakage from the system in its off state remained low. Lastly, we exploited a cognate trigger that only unwound the first 15 of the 18 bases in the switch stem. This design change yielded a number of benefits. It enabled the trigger RNA to bypass binding to the top three bases in the hairpin stem, which were all specified to be A and U bases, thereby eliminating corresponding sequence constraints for the trigger and leaving its length unchanged at 30-nts. Furthermore, avoiding disruption of the top three weak base pairs of the stem allowed them to breathe open spontaneously after lower bases in the stem were unwound. This design change effectively increased the size of the pre-RBS region by adding a 3-nt A/U enhancer element without a concomitant increase in off state leakage.

Figure 19C:
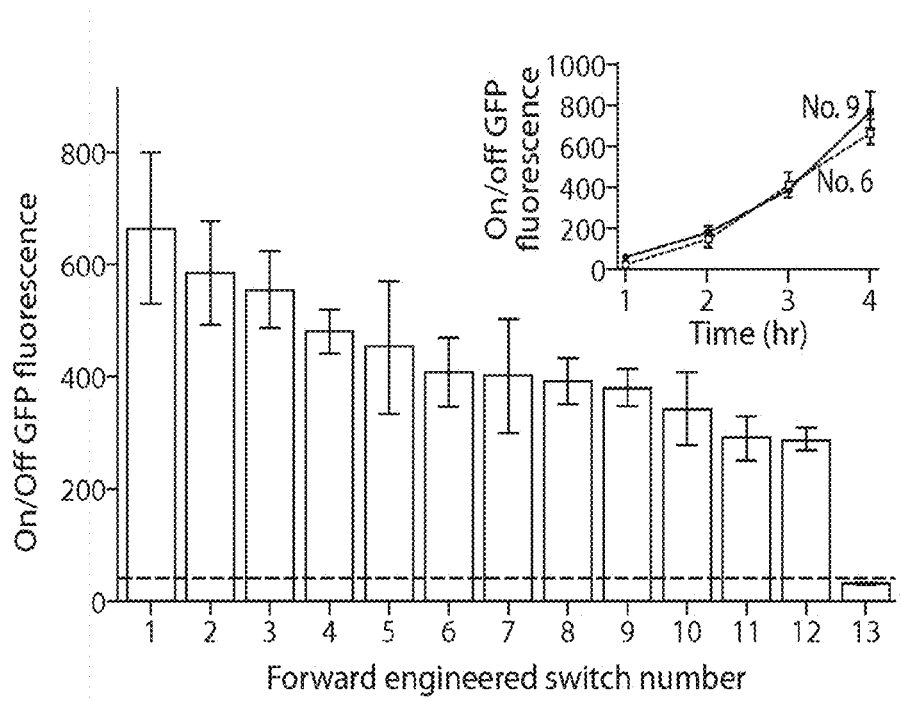

We employed NUPACK to design 13 forward engineered toehold switches with the four system modifications detailed above. FIG. 19C presents the on/off mode fluorescence ratios for the forward engineered translational activators regulating GFP after 3 hours of induction. There is dramatic increase in on/off fluorescence for almost all the systems tested, with 12 out 13 exhibiting a dynamic range that was comparable to or higher than the highest performance toehold switch from the initial library. These forward engineered systems exhibit an average on/off ratio of 406 compared to 43 for the initial toehold switch design. This mean on/off ratio rivals the dynamic range of protein-based regulation systems using a highly programmable system design and without requiring any evolution or large scale screening experiments. Furthermore, even the lowest performing optimized toehold switch displayed an on/off ratio of 33±4, which is still sufficient for many cellular decision making operations. Hourly time course measurements reveal activation of forward engineered switches after 1 or 2 hours of induction (FIG. 19C, inset). Furthermore, on state fluorescence increased steadily over 4 hours, yielding on/off levels well over 600 for both switches.

Figure 19D:
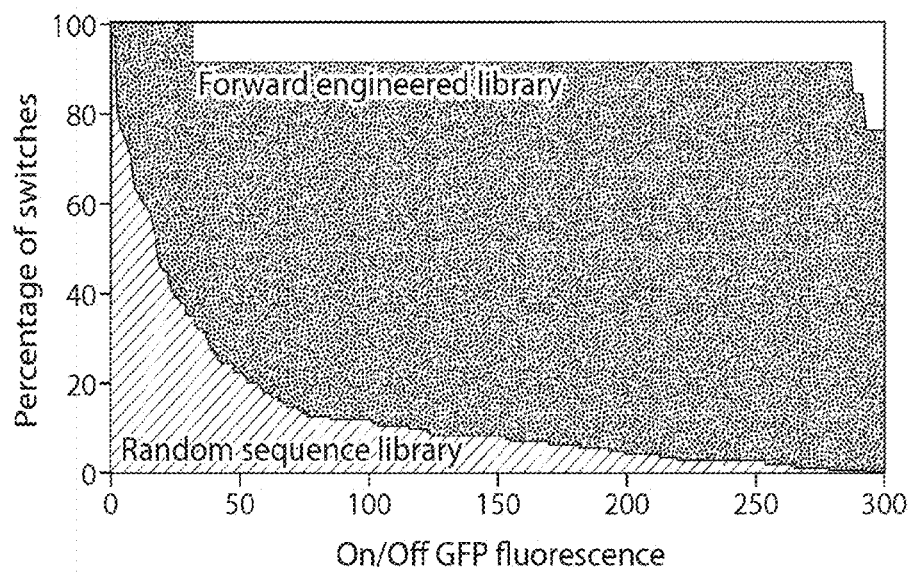

We quantified the effectiveness of our forward engineering strategy by calculating the percentage of forward engineered designs with on/off ratios exceeding a given minimal level and comparing them to the same calculation performed on the library of 168 toehold switches with random sequences (FIG. 19D). The yield of high performance switches is higher for the forward engineered switches for all on/off ratios tested. For instance, 92% of the forward engineered designs had on/off GFP fluorescence of at least 287 compared to a single switch out of 168 for of the random sequence library.

Thermodynamic Analysis of System Performance.

Figure 20A:
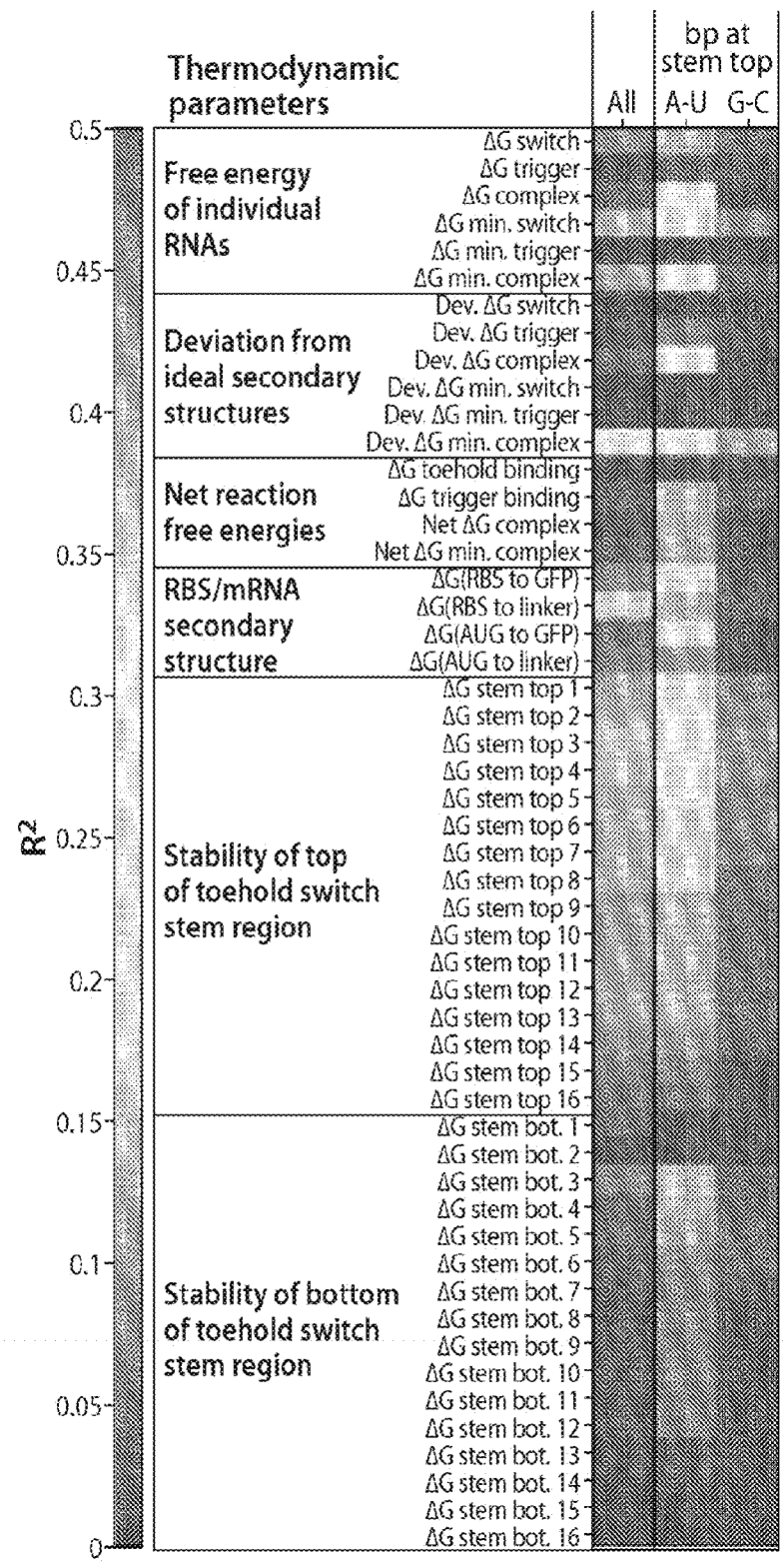
FIG. 20. Thermodynamic analysis of toehold switches. (A) Map of R2 values as a function of different thermodynamic parameters applied to subsets of on/off levels from the random sequence toehold switch library. The strongest correlation is found with the ΔGRBS-linker parameter (shown in red) for the subset of switches with a weak A-U base pair at the top of their stem. (B) Schematic illustrations showing position of the stem top base pair and the sequence range used to define ΔGRBS-linker. (C) Correlation between ΔGRBS-linker and on/off ratio measured for the 68 components in the toehold switch library with an A-U base pair at the top of the hairpin stem. (D) Strong correlation between ΔGRBS-linker and on/off ratio measured for the set of forward engineered systems.

Our forward engineering resulted in riboregulators with 92% likelihood of high dynamic range. To develop a predictive model of riboregulator activity, on/off ratios of the 168 initial switches with random sequences were analyzed in terms of a number of thermodynamic parameters falling into six different categories (FIG. 20A). On/off ratios as opposed to fluorescence output in the on and off states alone were used for quantitative analysis since fluorescence off states varied relatively little over the library, leaving on/off ratios essentially a measure of on state fluorescence. Following the treatment by Salis et al., Nat. Biotechnol. 27: 946-950, 2009, the amount of expressed protein p can be related to thermodynamic free energies through the equation $p \propto \exp(-k\Delta G)$, where k is a fitting parameter. Consequently, relationships between thermodynamic parameters and riboregulator on/off values can be evaluated by the coefficient of determination $R^2$ of a linear regression applied to a semi-logarithmic plot of free energy versus on/off ratio. However, each of the thermodynamic parameters failed to demonstrate any significant correlation with riboregulator output characteristics when applied to the full component library.

Figure 20B:
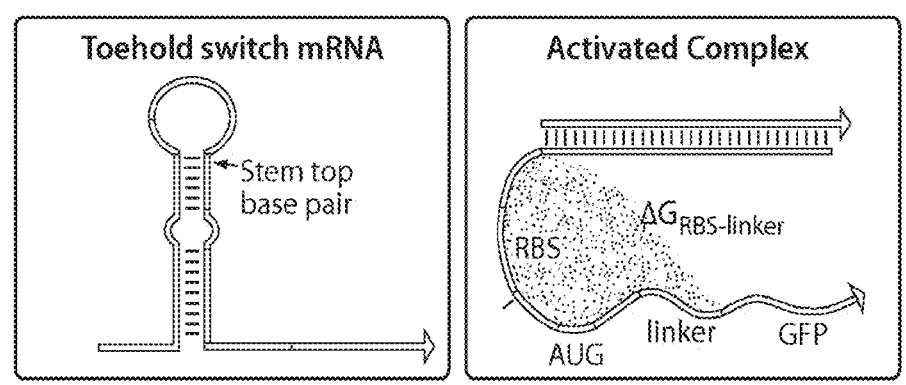
Figure 20C:
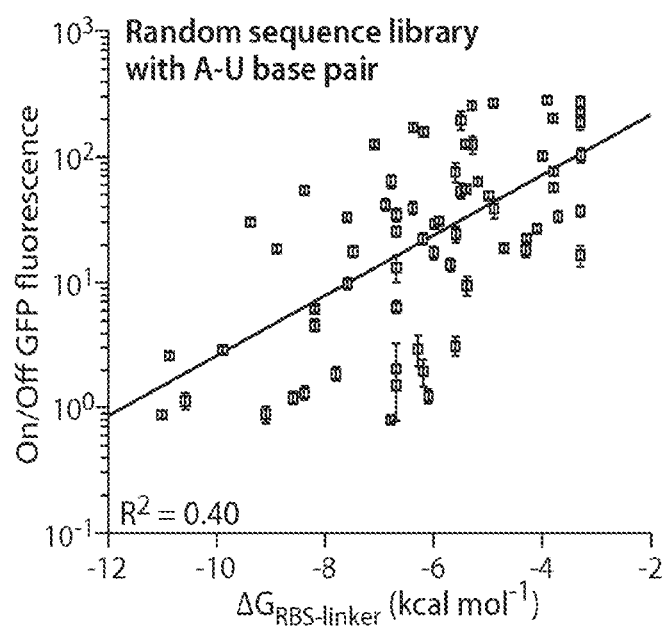

Based on the sequence-dependent effects observed in FIG. 19B, we began to search for relationships between thermodynamic parameters and subsets of toehold switches sharing similar sequence characteristics (FIG. 20A, data not shown). By probing $R^2$ values for a number of switch subsets, we identified a single parameter $\Delta G_{RBS-linker}$ that displayed a clear correlation with system output. $\Delta G$ RBS-linker is the free energy associated with the secondary structure of the region beginning immediately downstream of the RNA duplex of the riboregulator-trigger complex and running through to the end of the common 21-nt linker added after the hairpin module (FIG. 20B). It reflects the amount of energy required by the ribosome to unwind the RBS/early-mRNA region as it binds and begins translation of the output gene. Variations in translational efficiency have previously been linked to secondary structure early in mRNAs and similar thermodynamic factors have been employed to calculate the strength of prokaryotic RBSs (Salis et al., Nat. Biotechnol. 27: 946-950, 2009). FIG. 20C provides an example of the relationship between ΔGRBS-linker and the on/off ratios for a subset of 68 riboregulators each containing a weak A-U base pair at the top of its stem. This set of riboregulators from the library was the largest for which a correlation with ΔGRBS-linker with R2≥0.4 was identified. In contrast, the complementary subset of 100 riboregulators containing a strong GC base pair at the top of their stems displayed no correlation with ΔGRBS-linker with R2=0.024, possibly as a result of sequence dependent interactions with the ribosome at its standby site.

Figure 20D:
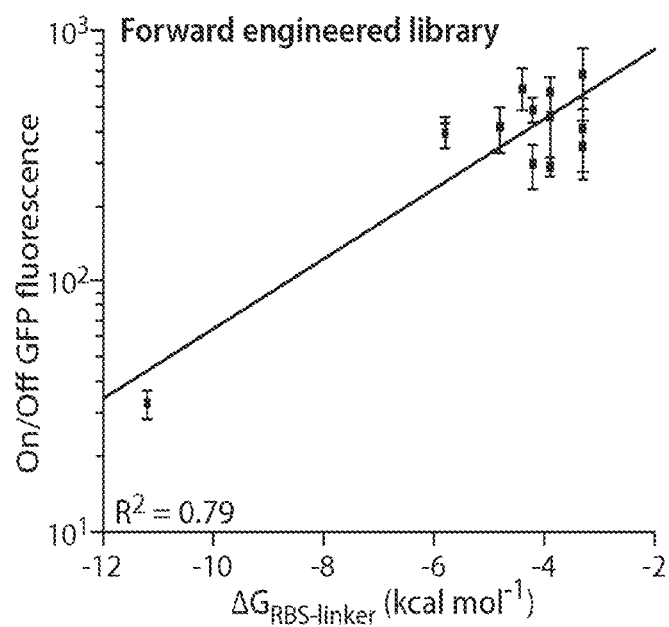

Having identified the importance of ΔGRBS-linker, we proceeded to investigate its relationship with on/off levels from the forward engineered systems. We found that ΔGRBS-linker exhibited a much stronger correlation with on/off levels, yielding $R^2=0.79$ (FIG. 20D). Most importantly, we found that this single thermodynamic term was sufficient to explain the single low performance forward engineered toehold switch. This particular toehold switch possessed relatively high secondary structure in the RBS-linker region that significantly decreased the translational efficiency of the activated switch mRNA.

Multiplexed Regulation.

Figure 21A:
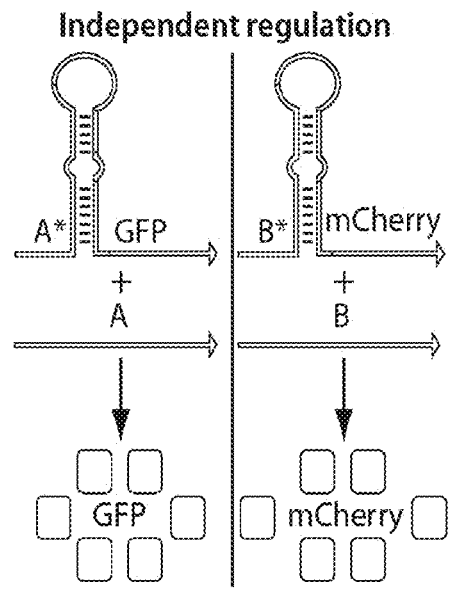
FIG. 21. Independent regulation and mRNA-based triggering using toehold switches. (A) Two orthogonal toehold switches triggered by RNAs A and B that independently regulate GFP and mCherry, respectively. (B) Two dimensional histograms of GFP and mCherry fluorescence for cells expressing all four input combinations of RNAs A and B confirm intended system behavior four hours after induction with IPTG. (C) mRNA-responsive toehold switches utilize an extended toehold domain denoted c* to bind to mRNA triggers with extensive secondary structure and activate expression of a GFP reporter. (D) On/off GFP fluorescence ratios for a series of toehold switches activated by the mCherry mRNA, and cat and aadA mRNAs conferring antibiotic resistance. (E) Mode GFP and mCherry fluorescence obtained from flow cytometry of mCherry sensors in their repressed and active states. Control expression levels were obtained from uninduced cells free of GFP-bearing plasmids and induced cells expressing either GFP or mCherry.
Figure 21B:
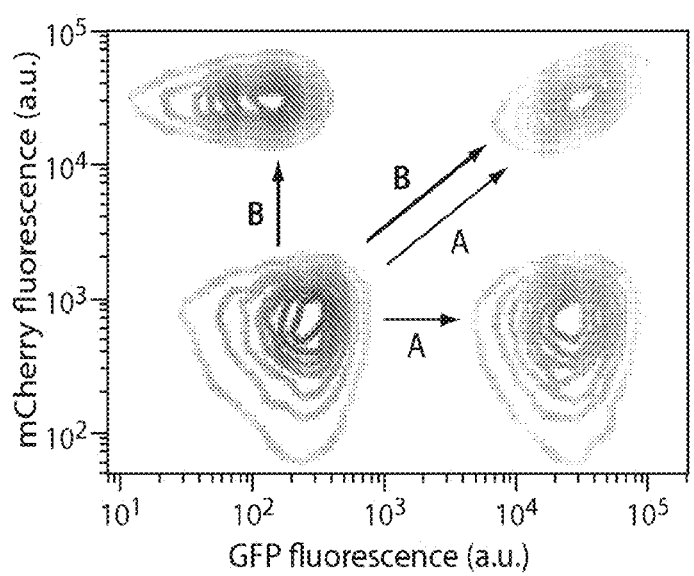

The orthogonality of the toehold switches can enable them to independently regulate multiple proteins simultaneously within the cell. To demonstrate this capability, we transformed cells with plasmids expressing two orthogonal toehold switch mRNAs expressing spectrally distinct fluorescent proteins GFP and mCherry, denoted A* and B*, respectively (FIG. 21A). The cognate trigger RNAs of these toehold switches were then expressed in all four possible combinations with reporter expression quantified using flow cytometry (FIG. 21B). Upon transcription of either the A or B trigger alone, GFP and mCherry fluorescence increases by over an order of magnitude, respectively, while fluorescence levels in the orthogonal channel are virtually unchanged. Co-expression of both A and B trigger RNAs yields strong increases in expression of both fluorophores, as expected for the two toehold switches.

Toehold Switches Triggered by Functional mRNAs.

Figure 21C:
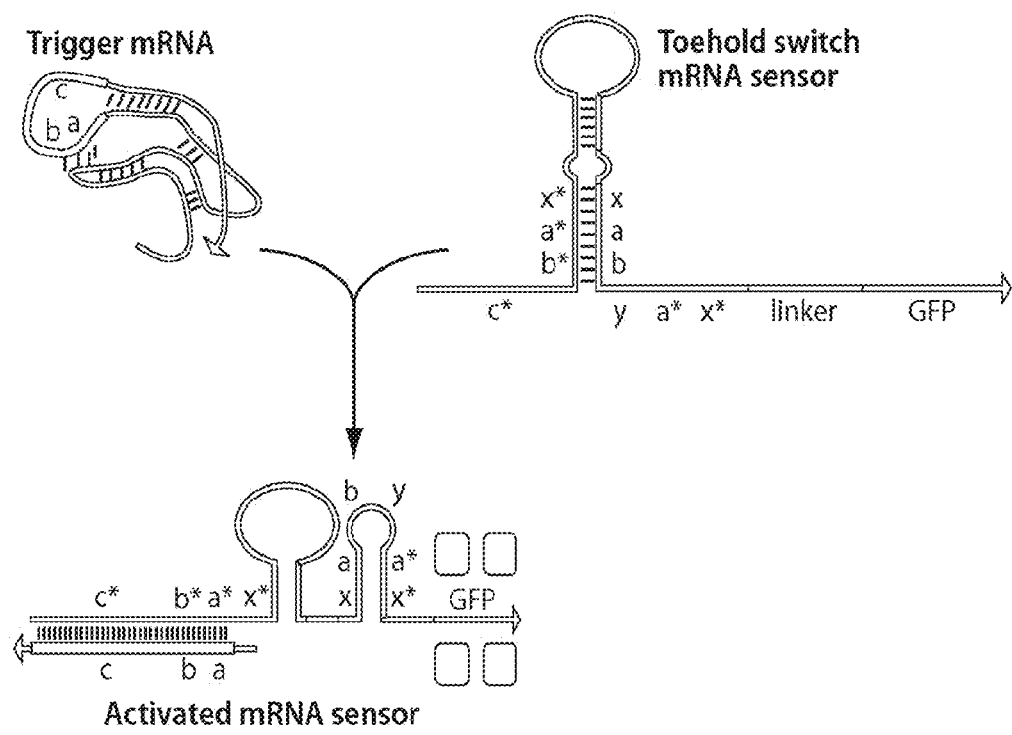

The sequence space afforded by the toehold switch design enables them to be triggered by functional mRNAs (FIG. 21C). However, the fixed sequences of these mRNA triggers present significant challenges for effective system activation. Unlike synthetic trigger RNAs designed to be completely single-stranded, strong secondary structures abound within the mRNAs, frustrating toehold binding and decreasing the thermodynamics driving the branch migration process. The toehold sequences defined by the trigger mRNA can also exhibit base pairing both internally and with sequences downstream of the hairpin module, and thus pose similar challenges to switch activation. In order to counter these effects, we increased the toehold domain length of the mRNA-responsive switches from 12-nts to ≥24-nts. This modification helped shift the importance of single-stranded regions for binding initiation from the trigger mRNA to the toehold switch itself, where only downstream sequences in the switch could hybridize with the binding region. In addition, we exploited a number of design features identified during detailed study of the highest performance toehold switch from the 168 system library. Toehold switch number 1 had an on/off ratio of 290±20 when paired with its complete 30-nt cognate trigger RNA. We found that on/off ratios increased sharply by using shortened trigger RNAs truncated from their 5' end. In particular, we observed that toehold switch number 1 could provide an 1900±200 on/off fluorescence in response to a trigger RNA intended to only unwind the bottom five bases of its stem. Secondary structure and thermodynamic analyses of the toehold switch number 1 system indicated that this extreme dynamic range was due to two factors. First, the stem of switch number 1 contained a relatively high proportion of weak A-U base pairs, and G-C base pairs in the stem were concentrated toward the bottom of the stem. Consequently, when a trigger disrupted the bottom five base pairs, half of the G-C base pairs in the stem were eliminated leaving a weak stem containing predominantly A-U base pairs available for ribosome binding. Furthermore, trigger binding to only the lower bases in the stem increased the pre-RBS region of the activated switch and provided additional enhancement of translation. Second, bases freed from the stem upon trigger binding were shown to interact with downstream bases in the switch linker region forming a weak stem loop (data not shown). This refolding mechanism led to an additional base of the stem being disrupted, which further weakened its repression strength, and decreased the energetic barrier to trigger binding.

We incorporated all the design features discussed above to generate toehold switches that were responsive to mRNAs. The switch hairpin modules were derived from the toehold switch number 1 sequence. Specifically, the top 12-bases and loop of the switch number 1 stem were used in all mRNA sensors (FIG. 21C). In addition, the size of the sensor loop was increased from 11- to 18-nts to increase reporter expression. The toehold and the bottom 6 base pairs of the sensor stem had variable bases programmed to interact with the trigger mRNA. 24- and 30-nt toeholds were used for initial mRNA binding and the bottom 6 base pairs were specified to be unwound by the trigger. To decrease the energetic barrier to stem unwinding by the trigger mRNA, we also explicitly encoded the downstream RNA refolding mechanism discussed above into the sensors. These RNA refolding elements induced the formation of a 6-bp stem loop after disruption of the bottom four base pairs of the switch stem and in turn forced the disruption of two additional bases in the switch stem. Using this bases toehold switch mRNA sensor design, we simulated the secondary structures and thermodynamics of all possible sensors along the full length of the trigger mRNA. We then used in silico screening to identify toehold switches that offered the best combination of sensor secondary structure and mRNA binding site availability.

Figure 21D:
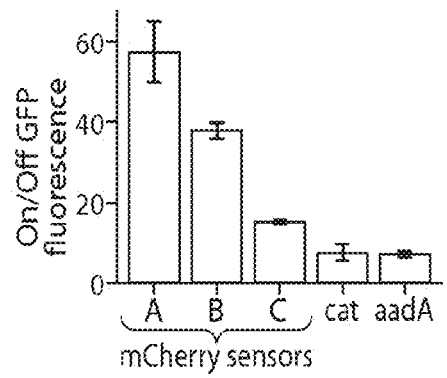

The resulting mRNA sensors were tested in the same manner as previous experiments, with the trigger mRNA expressed from a high copy ColE1 origin vector and toehold switches regulating GFP expressed from a medium copy ColA origin vector. We selected a trio of exogenous mRNA triggers, mCherry, chloramphenicol acetyltransferase (cat, conferring chloramphenicol resistance), and aadA (conferring spectinomycin resistance), for sensing experiments to minimize the likelihood of switch activation by endogenous RNAs. The mCherry trigger RNA featured an RBS region to enable efficient translation, while the two antibiotic resistance conferring mRNAs lacked an RBS, as translation by the ribosome could interfere with recognition and binding of the toehold switch. FIG. 21D presents the on/off GFP fluorescence measured from five toehold switches. The three sensors triggered by the translatable mCherry mRNA provide the strongest activation with design A displaying best on/off ratio of 57±10. The toehold switches triggered by the non-translatable mRNAs displayed more modest ~7-fold activation levels.

Figure 21E:
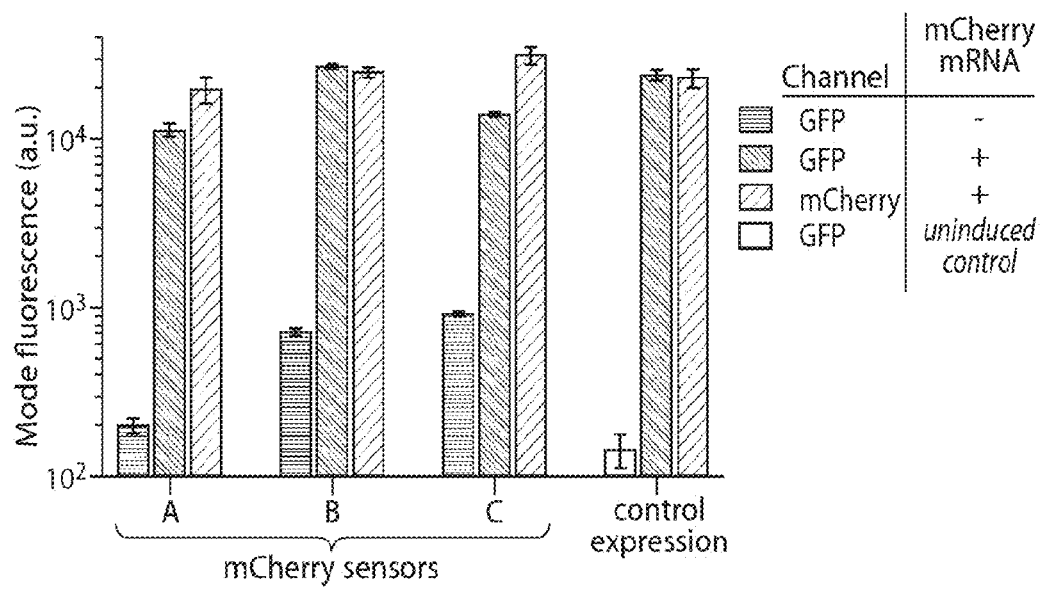

To establish the effect of toehold switch binding to translation from the trigger mRNA, we also performed experiments measuring mCherry output in the presence or absence of the mCherry sensor. FIG. 21E contains the fluorescence of GFP measured for the three mCherry-responsive switches in their active and repressed states in addition to the mCherry fluorescence measured from the activated cells. For comparison, fluorescence measurements obtained from control experiments are also presented showing background GFP fluorescence measured from uninduced cells as well as fluorescence measured from unregulated expression of GFP and mCherry from ColA and ColE1 origin vectors, respectively. Expression of mCherry is not strongly affected by transcription of the toehold switch RNA. This suggests that binding between the trigger and switch does not inhibit translation by the ribosome, although the molar excess of trigger RNA compared to switch dampens the strength of this effect in our experiments. The GFP expression levels from the activated switches vary within a factor of only 2.5, while leakage from the repressed switches varies by about 5-fold. This variation in leakage is the determining factor explaining variations in on/off levels of the mCherry sensors and is due to the use of the highly sensitive parent toehold switch as the parent design for the mRNA sensors.

Discussion

Toehold switches represent a versatile and powerful new platform for regulating translation at the post-transcriptional level. They combine an unprecedented degree of component orthogonality with system dynamic range comparable to widely used protein-based regulatory elements22. Comprehensive evaluation of in vivo switch-trigger pairwise interactions resulted in a set of 26 toehold switches with sub-12% cross talk levels. To our knowledge, this represents the largest library of orthogonal regulatory elements ever reported and exceeds previous libraries by a factor of over three in size (Takahashi et al., Nucleic Acids Res., 2013). At this point, the ultimate size of the orthogonal sets of toehold switches is limited by the throughput of our cross talk assay, not design features intrinsic to the riboregulators. Furthermore, forward engineering of 13 toehold switch systems yielded a subset of 12 new high performance components that exhibited an average on/off fluorescence ratio of 406, with the performance of the complete set predicted by a two parameter thermodynamic model.

Crucial to these advances was the adoption of new mechanisms for translational repression and initiation of RNA-RNA interactions in vivo. Toehold switches strongly repress translation in their off state by sequestering the sequences nearby the initiation codon of the regulated gene within RNA duplexes, in contrast to previous riboregulators that repress by blocking access to the RBS and in some cases the start codon (Isaacs et al., Nat. Biotechnol. 22:841-847, 2004; Rodrigo et al., Proc. Natl. Acad. Sci. USA 109:15271-15276, 2012; and Mutalik et al., Nat. Chem. Biol. 8:447-454, 2012). While earlier riboregulators have relied on loop-linear (Isaacs et al., Nat. Biotechnol. 22:841-847, 2004; and Mutalik et al., Nat. Chem. Biol. 8:447-454, 2012) and loop-loop (Lucks et al., Proc. Natl. Acad. Sci. USA 108: 8617-8622, 2011; Rodrigo et al., Proc. Natl. Acad. Sci. USA 109:15271-15276, 2012; and Takahashi et al., Nucleic Acids Res. 2013) interactions, toehold switches exploit toehold-mediated linear-linear RNA interactions to initiate binding between the riboregulator mRNA and trigger RNA. Taken together, these operating mechanisms enable the toehold switches to accept trigger RNAs with nearly arbitrary sequences, greatly expanding the sequence space for orthogonal operation, and they promote RNA-RNA interactions with high reaction kinetics by using extended toehold domains 12- to 15-nts in length. In contrast to earlier reports, thermodynamic analyses of toehold switch performance did not reveal significant correlations between riboregulator on/off levels and the free energy of the riboregulator-trigger interaction nor the free energy of toehold-trigger binding Mutalik et al., Nat. Chem. Biol. 8:447-454, 2012). These observations suggest that RNA-RNA interactions for the toehold switches are strongly thermodynamically and kinetically favoured.

We attribute the increased dynamic range of our toehold switches to three main factors. First, the increased kinetics and thermodynamic free energy driving trigger-switch interaction causes a higher percentage of the total switch mRNAs present in the cell to be triggered to produce the output produce. We found that the fraction of activated switch mRNAs was around 100% based on comparison measurements with unrepressed versions of the switch mRNA (FIG. 17C). Second, the design of the toehold switches, in which no bases of the RBS are enclosed within a stem, provides a much better platform through which to engineer the RBS and its surrounding bases for optimal expression of the regulated gene. Experiments varying the loop size of the toehold switch mRNA demonstrated a very strong dependence between the on state fluorescence of the switch and the presence of longer A-rich regions upstream of the RBS (data not shown). Importantly, this RBS enhancement required only additional bases to be added to the loop region and did not require corresponding changes in the sequence of the trigger RNA. In contrast, for many previous riboregulator systems, similar RBS engineering would require modifications to be made to both pairs of riboregulator RNAs, complicating the design and requiring deconvolution of effects from RBS and the RNA-RNA interactions to properly interpret results. Lastly, the toehold switches were designed in silico to provide RBS and early mRNA regions with very little secondary structure to promote efficient translation of the regulated gene. Although this was accomplished by adding additional bases and a linker to the N-terminal of the output gene, algorithms to select optimal codons with respect to mRNA secondary structure can be used to produce toehold switches without adding N-terminal bases. Synonymous codons should also enable the construction of large orthogonal sets of such N-terminal restricted of switches.

Sequences for various riboregulators described herein:

TABLE 1

Sequence and performance information for certain toehold switches and triggers from the initial set of 24 random sequence toehold switches.

| Toehold switch number | Switch sequence | Trigger sequence | On/off |
|---|---|---|---|
| 4 | GGGAAUUGAUAUUGUGAUUAUGU GAUGAUUGUAAACAGAGGAGAUA CAAUAUGCACAUAAUCAACCUGG CGGCAGCGCAAAAGAUGCGUAAA (SEQ ID NO: 1) | GGGACAUACGGACUCACGUGUC CGUAUGUCAAUACAAUCAUCAC AUAAUCACAAUAUCAAUUACU (SEQ ID NO: 2) | 264.6 ± 19.9 |
| 10 | GGGAAUUGAUAUUGUUCGUUUCG UAUGAUCUAAGACAGAGGAGAUU AGAUAUGACGAAACGAAACCUGG CGGCAGCGCAAAAGAUGCGUAAA (SEQ ID NO: 3) | GGGACAUACGGACUCACGUGUC CGUAUGUAACUUAGAUCAUACG AAACGAACAAUAUCAAUUACU (SEQ ID NO: 4) | 192.4 ± 26.9 |
| 14 | GGGAAUUGAUAUUGUAGUAUGUU GAAGUGAUUGAACAGAGGAGACA AUCAAUGCAACAUACUAACCUGG CGGCAGCGCAAAAGAUGCGUAAA (SEQ ID NO: 5) | GGGACAUACGGACUCACGUGUC CGUAUGUCAGCAAUCACUUCAA CAUACUACAAUAUCAAUUACU (SEQ ID NO: 6) | 153.4 ± 10.1 |

TABLE 2

Sequence and performance information for certain toehold switches and triggers from the set of 144 orthogonal random sequence toehold switches.

| Toehold switch number | Switch sequence | Trigger sequence | On/off |
|---|---|---|---|
| 1 | GGGUGAAUGAAUUGUAGGCUUGU UAUAGUUAUGAACAGAGGAGACA UAACAUGAACAAGCCUAACCUGG CGGCAGCGCAAAAGAUGCGUAAA (SEQ ID NO: 7) | GGGACCGUGGACCGCAUGAGGU CCACGGUAAACAUAACUAUAAC AAGCCUACAAUUCAUUCAAAC (SEQ ID NO: 8) | 292.0 ± 19.5 |
| 2 | GGGUAUAAGUAAAUCGCUUGCUG UAUGUCGUUAAACAGAGGAGAUA ACGAAUGACAGCAAGCAACCUGG CGGCAGCGCAAAAGAUGCGUAAA (SEQ ID NO: 9) | GGGAUGCCCGUAGUUCAUUCUA CGGGCAUGAAUAACGACAUACA GCAAGCGAUUUACUUAUACUA (SEQ ID NO: 10) | 279.6 ± 17.6 |
| 3 | GGGUGAUGGAAUAAGGCUGUGUA UAUGAUGUUAGACAGAGGAGAUA ACAUAUGAUACACAGCAACCUGG CGGCAGCGCAAAAGAUGCGUAAA (SEQ ID NO: 11) | GGGUCAGUUCCUGAGGUACCAG GAACUGAAACUAACAUCAUAUA CACAGCCUUAUUCCAUCACAC (SEQ ID NO: 12) | 265.3 ± 28.2 |
| 5 | GGGUAGAUAUUGAAUGCUGCUGU UAUGUCGUUAAACAGAGGAGAUA ACGAAUGAACAGCAGCAACCUGG CGGCAGCGCAAAAGAUGCGUAAA (SEQ ID NO: 13) | GGGACGCGAAAUGCUAUUCCAU UUCGCGUGACUAACGACAUAAC AGCAGCAUUCAAUAUCUAAAC (SEQ ID NO: 14) | 253.0 ± 12.5 |
| 6 | GGGAUAAGUAGAUAAGAUUGUUA GAUGGCUUCGAACAGAGGAGACG AAGCAUGCUAACAAUCAACCUGG CGGCAGCGCAAAAGAUGCGUAAA (SEQ ID NO: 15) | GGGUCGUGCGCUCUGAGCCGAG CGCACGAGAACGAAGCCAUCUA ACAAUCUUAUCUACUUAUCAC (SEQ ID NO: 16) | 219.8 ± 16.5 |
| 7 | GGGAUCACUUAUUGUCGUCUUUG UAUGUCUGUAAACAGAGGAGAUA CAGAAUGACAAAGACGAACCUGG CGGCAGCGCAAAAGAUGCGUAAA (SEQ ID NO: 17) | GGGACGUCGAUUCACCGUCGAA UCGACGUAGAUACAGACAUACA AAGACGACAAUAAGUGAUAGA (SEQ ID NO: 18) | 213.3 ± 28.3 |
| 8 | GGGACAAAGAUUGGUCGUUUCAU UACCGUUAGAAACAGAGGAGAUC UAACAUGAAUGAAACGAACCUGG CGGCAGCGCAAAAGAUGCGUAAA (SEQ ID NO: 19) | GGGACUCCAGGCGGAAUAACGC CUGGAGUAAAUCUAACGGUAAU GAAACGACCAAUCUUUGUAUG (SEQ ID NO: 20) | 200.8 ± 13.5 |

TABLE 2-continued

Sequence and performance information for certain toehold switches and triggers from the set of 144 orthogonal random sequence toehold switches.

| Toehold switch number | Switch sequence | Trigger sequence | On/off |
|---|---|---|---|
| 9 | GGGCGAAAGUGUAUGGCUGAUAU GAUGUAGUUAAACAGAGGAGAUA ACUAAUGCAUAUCAGCAACCUGG CGGCAGCGCAAAAGAUGCGUAAA (SEQ ID NO: 21) | GGGUCGCACGGUUCCGCCUAAC CGUGCGAGAAUAACUACAUCAU AUCAGCCAUACACUUUCGAAC (SEQ ID NO: 22) | 194.4 ± 31.3 |
| 11 | GGGUAAGAUUUGAUGGCUAUUUG UACGUGUUCGAACAGAGGAGACG AACAAUGACAAAUGCAACCUGG CGGCAGCGCAAAAGAUGCGUAAA (SEQ ID NO: 23) | GGGACCAUUCGCCCUACUUGGC GAAUGGUAAGCGAACACGUACA AAUAGCCAUCAAAUCUUAACU (SEQ ID NO: 24) | 181.2 ± 13.0 |
| 12 | GGGAAUUGGAUGAAGGCGGUAAG UAUGAUUGUAGACAGAGGAGAUA CAAUAUGACUUACCGCAACCUGG CGGCAGCGCAAAAGAUGCGUAAA (SEQ ID NO: 25) | GGGUCCAGUCUAGACUGACCUA GACUGGACAAUACAAUCAUACU UACCGCCUUCAUCCAAUUACU (SEQ ID NO: 26) | 169.9 ± 16.7 |
| 13 | GGGUAGAAUUUGAUACUUGAUUU GAUGGCUUGAAACAGAGGAGAUC AAGCAUGCAAAUCAAGAACCUGG CGGCAGCGCAAAAGAUGCGUAAA (SEQ ID NO: 27) | GGGUCUAAUGCGAGUAAAGUCG CAUUAGAAUAUCAAGCCAUCAA AUCAAGUAUCAAAUUCUAAAG (SEQ ID NO: 28) | 155.3 ± 8.6 |
| 15 | GGGCGUUAUACUUUGUCGUUCUG CGUGUCGUUAAACAGAGGAGAUA ACGAAUGGCAGAACGAAACCUGG CGGCAGCGCAAAAGAUGCGUAAA (SEQ ID NO: 29) | GGGACUGAGGUACCUCGAAGUA CCUCAGUAGAUAACGACACGCA GAACGACAAAGUAUAACGAAA (SEQ ID NO: 30) | 124.7 ± 11.0 |
| 16 | GGGUAAGAAUGAUAAAGGUAAGU AGUGAGUUGAAACAGAGGAGAUC AACUAUGUACUUACCUAACCUGG CGGCAGCGCAAAAGAUGCGUAAA (SEQ ID NO: 31) | GGGCCAUGACUCCUAAUUCGGA GUCAUGGAAAUCAACUCACUAC UUACCUUUAUCAUUCUUACUU (SEQ ID NO: 32) | 123.2 ± 23.0 |
| 17 | GGGCGAUAAAGACUGAGGCUGGG UAUGGUUAGAAACAGAGGAGAUC UAACAUGACCCAGCCUAACCUGG CGGCAGCGCAAAAGAUGCGUAAA (SEQ ID NO: 33) | GGGCCUCGACGUUCGUGAUAAC GUCGAGGCAAUCUAACCAUACC CAGCCUCAGUCUUUAUCGCAA (SEQ ID NO: 34) | 122.6 ± 0.8 |
| 18 | GGGAUAGAUGAUUGUGCUUAGUU UAUGAUUCUGAACAGAGGAGACA GAAUAUGAAACUAAGCAACCUGG CGGCAGCGCAAAAGAUGCGUAAA (SEQ ID NO: 35) | GGGACAUCCUAAGUUGACUCUU AGGAUGUAAACAGAAUCAUAAA CUAAGCACAAUCAUCUAUACA (SEQ ID NO: 36) | 115.1 ± 7.9 |
| 19 | GGGAUAAUGAUGAUGAGUAUGUU GAAGGUGUAAGACAGAGGAGAUU ACACAUGCAACAUACUAACCUGG CGGCAGCGCAAAAGAUGCGUAAA (SEQ ID NO: 37) | GGGUCGUGUGAUGCUAUCUCAU CACACGACAAUUACACCUUCAA CAUACUCAUCAUCAUUAUCAC (SEQ ID NO: 38) | 103.5 ± 10.5 |
| 20 | GGGCGUUAAUCUCUGGCUUGCUU UAUGUCUGUAAACAGAGGAGAUA CAGAAUGAAAGCAAGCAACCUGG CGGCAGCGCAAAAGAUGCGUAAA (SEQ ID NO: 39) | GGGUCAUGACUGGGACACGCCA GUCAUGAGAAUACAGACAUAAA GCAAGCCAGAGAUUAACGAAG (SEQ ID NO: 40) | 101.9 ± 8.4 |
| 21 | GGGUAAAGAUGAAACGCGUGAAU GAUAGUAUUGAACAGAGGAGACA AUACAUGCAUUCACGCAACCUGG CGGCAGCGCAAAAGAUGCGUAAA (SEQ ID NO: 41) | GGGUCACCUCCAGGCACGACUG GAGGUGAAUACAAUACUAUCAU UCACGCGUUUCAUCUUUACUU (SEQ ID NO: 42) | 86.6 ± 14.5 |
| 22 | GGGCAUUAAGAUUGUACUUGUAA GAUCGUGUCGAACAGAGGAGACG ACACAUGCUUACAAGUAACCUGG CGGCAGCGCAAAAGAUGCGUAAA (SEQ ID NO: 43) | GGGACCUAGCGGAGCGCAGUCC GCUAGGUAAACGACACGAUCUU ACAAGUACAAUCUUAAUGAAA (SEQ ID NO: 44) | 83.1 ± 2.0 |

TABLE 2-continued

Sequence and performance information for certain toehold switches and triggers from the set of 144 orthogonal random sequence toehold switches.

| Toehold switch number | Switch sequence | Trigger sequence | On/off |
|---|---|---|---|
| 23 | GGGUAUGAAUUGAUGUCGAUUGU UAUGUCUUGAGACAGAGGAGAUC AAGAAUGAACAAUCGAAACCUGG CGGCAGCGCAAAAGAUGCGUAAA (SEQ ID NO: 45) | GGGACCCGACCGCGUCCUGGCG GUCGGGUAAAUCAAGACAUAAC AAUCGACAUCAAUUCAUACUA (SEQ ID NO: 46) | 75.2 ± 4.9 |
| 24 | GGGUAAAGAUGAGAACGCUUGUG AAUGAUGUGAAACAGAGGAGAUC ACAUAUGUCACAAGCGAACCUGG CGGCAGCGCAAAAGAUGCGUAAA (SEQ ID NO: 47) | GGGUCGGGACACGGGCAUACGU GUCCCGACAAUCACAUCAUUCA CAAGCGUUCUCAUCUUUACUU (SEQ ID NO: 48) | 74.8 ± 13.0 |
| 25 | GGGUGAUAGAUGAAGGCAGGCGU UAUAGUUUAGAACAGAGGAGACU AAACAUGAACGCCUGCAACCUGG CGGCAGCGCAAAAGAUGCGUAAA (SEQ ID NO: 49) | GGGUCGUGGGCCUGCCUAAAGG CCCACGAGAACUAAACUAUAAC GCCUGCCUUCAUCUAUCAAAC (SEQ ID NO: 50) | 72.6 ± 3.7 |
| 26 | GGGUAAGUAAUGAAGUCUAAGUG UAUCGUGUCGGACAGAGGAGACG ACACAUGACACUUAGAAACCUGG CGGCAGCGCAAAAGAUGCGUAAA (SEQ ID NO: 51) | GGGACGAACUUGAUCAAAUUCA AGUUCGUAAACGACACGAUACA CUUAGACUUCAUUACUUACAU (SEQ ID NO: 52) | 68.2 ± 10.3 |
| 27 | GGGAUAGAAUUAGAAAUGAAAUA GAUGGUUACGAACAGAGGAGACG UAACAUGCUAUUUCAUAACCUGG CGGCAGCGCAAAAGAUGCGUAAA (SEQ ID NO: 53) | GGGUCGCUUGUACUCUUGCGUA CAAGCGAAAGCGUAACCAUCUA UUUCAUUUCUAAUUCUAUCUA (SEQ ID NO: 54) | 67.3 ± 10.7 |
| 28 | GGGAUAGAAAUUGAUCGUUAGUU UAUGUUGCCGGACAGAGGAGACG GCAAAUGAAACUAACGAACCUGG CGGCAGCGCAAAAGAUGCGUAAA (SEQ ID NO: 55) | GGGUAUCUACUCGACUUCGCGA GUAGAUAAAGCGGCAACAUAAA CUAACGAUCAAUUUCUAUAAC (SEQ ID NO: 56) | 66.9 ± 8.0 |
| 29 | GGGAGUUUGAAUAUGGCGAAAUG AAUGCUUUGAAACAGAGGAGAUC AAAGAUGUCAUUUCGCAACCUGG CGGCAGCGCAAAAGAUGCGUAAA (SEQ ID NO: 57) | GGGACGAGAGCUCCUAGCAGAG CUCUCGUAUAUCAAAGCAUUCA UUUCGCCAUAUUCAAACUAAC (SEQ ID NO: 58) | 63.1 ± 6.6 |
| 30 | GGGUAAAGAUGAUAAGAUGUGAG UAAGGUAGUAAACAGAGGAGAUA CUACAUGACUCACAUCAACCUGG CGGCAGCGCAAAAGAUGCGUAAA (SEQ ID NO: 59) | GGGCACGACUAGAAACCGAUCU AGUCGUGCAAUACUACCUUACU CACAUCUUAUCAUCUUUACUU (SEQ ID NO: 60) | 63.0 ± 5.6 |
| 31 | GGGAUCUAAAUGUAUUCGUUCGU UAUGGUAUUGAACAGAGGAGACA AUACAUGAACGAACGAAACCUGG CGGCAGCGCAAAAGAUGCGUAAA (SEQ ID NO: 61) | GGGCGUCGCUGUUCGGGUAAAC AGCGACGGAACAAUACCAUAAC GAACGAAUACAUUUAGAUACU (SEQ ID NO: 62) | 62.0 ± 62 |
| 32 | GGGUCAAUUUCGUAUUAGUAUGU UAUGGUUCUGAACAGAGGAGACA GAACAUGAACAUACUAAACCUGG CGGCAGCGCAAAAGAUGCGUAAA (SEQ ID NO: 63) | GGGACUCGGUCUCUAUGUCGAG ACCGAGUAAACAGAACCAUAAC AUACUAAUACGAAAUUGAAGC (SEQ ID NO: 64) | 59.4 ± 7.6 |
| 33 | GGGAAUUUGGAAGUAGAGUAGUA GAUAGUUUAUGAACAGAGGAGACA UAACAUGCUACUACUCAACCUGG CGGCAGCGCAAAAGAUGCGUAAA (SEQ ID NO: 65) | GGGCAGAGCGGUCUGUUUCGAC CGCUCUGAAACAUAACUAUCUA CUACUCUACUUCCAAAUUCUA (SEQ ID NO: 66) | 58.5 ± 9.6 |
| 34 | GGGAGUAAUGAUGAUAUAGUUUG AAUGUAGUGAAACAGAGGAGAUC ACUAAGUGCAAACUAUAACCUGG CGGCAGCGCAAAAGAUGCGUAAA (SEQ ID NO: 67) | GGGACCGUCACCCUACAUCGGG UGACGGUAAAUCACUACAUUCA AACUAUAUCAUCAUUACUAAC (SEQ ID NO: 68) | 57.1 ± 5.0 |

TABLE 2-continued

Sequence and performance information for certain toehold switches and triggers from the set of 144 orthogonal random sequence toehold switches.

| Toehold switch number | Switch sequence | Trigger sequence | On/off |
|---|---|---|---|
| 35 | GGGAUAAUGGAGAUGGAGUAGGG UAUGAUUGUAGACAGAGGAGAUA CAAUAUGACCCUACUCAACCUGG CGGCAGCGCAAAAGAUGCGUAAA (SEQ ID NO: 69) | GGGCCUAGAAACUGUACGAAGU UUCUAGGCAUUACAAUCAUACC CUACUCCAUCUCCAUUAUCUU (SEQ ID NO: 70) | 53.9 ± 4.5 |
| 36 | GGGAUGAAUAUGGACAGUUGAGU AGUGAUGUGAAACAGAGGAGAUC ACAUAUGUACUCAACUAACCUGG CGGCAGCGCAAAAGAUGCGUAAA (SEQ ID NO: 71) | GGGAGUCAGGACCGCAUCAGGU CCUGACUAAAUCACAUCACUAC UCAACUGUCCAUAUUCAUCUU (SEQ ID NO: 72) | 53.4 ± 6.7 |
| 37 | GGGAUGGAGAUUGAUUAUGAUUG GAUGUGCUUAAACAGAGGAGAUA AGCAAUGCCAAUCAUAAACCUGG CGGCAGCGCAAAAGAUGCGUAAA (SEQ ID NO: 73) | GGGUCGACCGCUCCUGCUCGAG CGGUCGACAAUAAGCACAUCCA AUCAUAAUCAAUCUCCAUAAC (SEQ ID NO: 74) | 52.7 ± 1.8 |
| 38 | GGGAGUAAGAAUUGUGAUAAAGU AAUGUGCGUGAACAGAGGAGACA CGCAAUGUACUUUAUCAACCUGG CGGCAGCGCAAAAGAUGCGUAAA (SEQ ID NO: 75) | GGGUCACGGAGCGGAUUUGCGC UCCGUGAGAACACGCACAUUAC UUUAUCACAAUUCUUACUUCA (SEQ ID NO: 76) | 51.0 ± 4.5 |

TABLE 3

Sequence and performance information for the set of forward engineered toehold switches.

| Toehold switch number | Switch sequence | Trigger sequence | On/off |
|---|---|---|---|
| 1 | GGGUCUUAUCUUAUCUAUCUCGUUU AUCCCUGCAUACAGAAACAGAGGAG AUAUGCAAUGAUAAACGAGAACCUG GCGGCAGCGCAAAAGAUGCGUAAA (SEQ ID NO: 77) | GGGACUGACUAUUCUGUGCAAU AGUCAGUAAAGCAGGGAUAAAC GAGAUAGAUAAGAUAAGAUAG (SEQ ID NO: 78) | 665 ± 135 |
| 2 | GGGAGUUUGAUUACAUUGUCGUUUA GUUUAGUGAUACAUAAACAGAGGAG AUAUCACAUGACUAAACGAAACCUG GCGGCAGCGCAAAAGAUGCGUAAA (SEQ ID NO: 79) | GGGACAGAUCCACUGAGGCGUG GAUCUGUGAACACUAAACUAAA CGACAAUGUAAUCAAACUAAC (SEQ ID NO: 80) | 586 ± 92 |
| 3 | GGGAUCUAUUACUACUUACCAUUGU CUUGCUCUAUACAGAAACAGAGGAG AUAUAGAAUGAGACAAUGGAACCUG GCGGCAGCGCAAAAGAUGCGUAAA (SEQ ID NO: 81) | GGGUGAUGGGACAUUCCGAUGU CCCAUCAAUAAGAGCAAGACAA UGGUAAGUAGUAAUAGAUAAG (SEQ ID NO: 82) | 557 ± 68 |
| 4 | GGGCGAUUAUGGAUUAGAGCUCCGU UUACUGUCAUACAAGAACAGAGGAG AUAUGACAUGAAACGGAGCAACCUG GCGGCAGCGCAAAAGAUGCGUAAA (SEQ ID NO: 83) | GGGACGAAUUCACCCUAAUGUG AAUUCGUAAAGACAGUAAACGG AGCUCUAAUCCAUAAUCGAAC (SEQ ID NO: 84) | 483 ± 40 |
| 5 | GGGUAUGUAAUUGAUUUGGCUUCUG UUAGUUUCAUACAAGAACAGAGGAG AUAUGAAAUGAACAGAAGCAACCUG GCGGCAGCGCAAAAGAUGCGUAAA (SEQ ID NO: 85) | GGGUCCAUUCUAGGUGAUACUA GAAUGGAGCAGAAACUAACAGA AGCCAAAUCAAUUACAUACUA (SEQ ID NO: 86) | 453 ± 119 |
| 6 | GGGCUUAAUCUUACCUUCGCUUGUU CUGUUCCGAUACAGAAACAGAGGAG AUAUCGGAUGAGAACAAGCAACCUG GCGGCAGCGCAAAAGAUGCGUAAA (SEQ ID NO: 87) | GGGACAAUCGGGACGACACUCC CGAUUGUGAACGGAACAGAACA AGCGAAGGUAAGAUUAAGGUA (SEQ ID NO: 88) | 409 ± 62 |

TABLE 3-continued

Sequence and performance information for the set of forward engineered toehold switches.

| Toehold switch number | Switch sequence | Trigger sequence | On/off |
|---|---|---|---|
| 7 | GGGUCACUUAAUCAUUUGUCGUCGU UUCUAUCUAUACAAGAACAGAGGAG AUAUAGAAUGAAACGACGAAACCUG GCGGCAGCGCAAAAGAUGCGUAAA (SEQ ID NO: 89) | GGGUCGAGUAGACAGAGCUGUC UACUCGAAUAAGAUAGAAACGA CGACAAAUGAUUAAGUGAGAA (SEQ ID NO: 90) | 403 ± 99 |
| 8 | GGGACCUCUACUUACUCUCACUCUU ACUUCUGCAUAGUAGAACAGAGGAG AUAUGCAAUGGUAAGAGUGAACCUG GCGGCAGCGCAAAAGAUGCGUAAA (SEQ ID NO: 91) | GGGACUGAGCUGCUAUCACGCA GCUCAGUAGAGCAGAAGUAAGA GUGAGAGUAAGUAGAGGUAGA (SEQ ID NO: 92) | 393 ± 41 |
| 9 | GGGCUUACUACUUUGACACCUGAUU CUGACACGAUAACAGAACAGAGGAG AUAUCGUAUGAGAAUCAGGAACCUG GCGGCAGCGCAAAAGAUGCGUAAA (SEQ ID NO: 93) | GGGUCAAUUACCCGUGGUAGGG UAAUUGAAAGCGUGUCAGAAUC AGGUGUCAAAGUAGUAAGUAG (SEQ ID NO: 94) | 381 ± 32 |
| 10 | GGGAAUGGAAUGAAUGAACUGCUUG UCUUAUGUAUACAGAAACAGAGGAG AUAUACAAUGGACAAGCAGAACCUG GCGGCAGCGCAAAAGAUGCGUAAA (SEQ ID NO: 95) | GGGCGAAGUGUCCGUAUGAGGA CACUUCGACGACAUAAGACAAG CAGUUCAUUCAUUCCAUUUAG (SEQ ID NO: 96) | 343 ± 64 |
| 11 | GGGCGAAUAGAAAUGAAGGCUAGUG UCGUUGUCAUACAGAAACAGAGGAG AUAUGACAUGGACACUAGCAACCUG GCGGCAGCGCAAAAGAUGCGUAAA (SEQ ID NO: 97) | GGGACUCCACGCCGACCGUGGC GUGGAGUAAAGACAACGACACU AGCCUUCAUUUCUAUUCGAUU (SEQ ID NO: 98) | 292 ± 40 |
| 12 | GGGCAAUUUCGUAUAUGUUCGUCUU UGCUGUUCAUACAAGAACAGAGGAG AUAUGAAAUGCAAAGACGAAACCUG GCGGCAGCGCAAAAGAUGCGUAAA (SEQ ID NO: 99) | GGGCGACGAUGCCAGGUAUGGC AUCGUCGGACGAACAGCAAAGA CGAACAUAUACGAAAUUGAAA (SEQ ID NO: 100) | 288 ± 19 |
| 13 | GGGAUGGAAUUGAGAUGGGCUUUCG CGAGAUUGAUACAGAAACAGAGGAG AUAUCAAAUGCGCAAAGCAACCUG GCGGCAGCGCAAAAGAUGCGUAAA (SEQ ID NO: 101) | GGGUGCGGUAGUAGGUUCCUAC UACCGCAAUACAAUCUCGCGAA AGCCCAUCUCAAUUCCAUACU (SEQ ID NO: 102) | 33 ± 3 |

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A toehold riboregulator comprising
an RNA comprising in a 5' to 3' order
   (1) a single-stranded toehold domain,
   (2) a fully or partially double-stranded stem domain comprising
      (i) an initiation codon, and
      (ii) a loop domain comprising a ribosome binding site, and
   (3) a coding domain.

2. The riboregulator of claim 1, further comprising a spacer domain.

3. The riboregulator of claim 2, wherein the spacer domain encodes low molecular weight amino acids.

4. The riboregulator of claim 2, wherein the spacer is about 9-33 nucleotides in length.

5. The riboregulator of claim 2, wherein the spacer is about 21 nucleotides in length.

6. The riboregulator of claim 2, wherein the spacer domain is situated between the stem domain and the coding domain.

7. The riboregulator of claim 1, wherein the stem domain comprises sequence upstream (5') and/or downstream (3') of the initiation codon.

8. The riboregulator of claim 7, wherein the sequence upstream of the initiation codon is about 6 nucleotides.

9. The riboregulator of claim 7, wherein the sequence downstream of the initiation codon is about 9 nucleotides.

10. The riboregulator of claim 7, wherein the sequence downstream of the initiation codon does not encode a stop codon.

11. The riboregulator of claim 1, wherein the coding domain encodes a reporter protein.

12. The riboregulator of claim 11, wherein the reporter protein is green fluorescent protein (GFP).

13. The riboregulator of claim 1, wherein the coding domain encodes a non-reporter protein.

14. The riboregulator of claim 1, wherein the toehold domain is complementary in sequence to a naturally occurring RNA.

15. The riboregulator of claim 1, wherein the toehold domain is complementary in sequence to a non-naturally occurring RNA.

16. A trans-activating RNA (taRNA) comprising
a first domain that hybridizes to a toehold domain of a riboregulator of claim 1 and that comprises no or minimal secondary structure, and a second domain that hybridizes to a sequence in the stem domain of the riboregulator of claim 1.

17. The trans-activating RNA of claim 16, wherein the first domain is 100% complementary to the toehold domain.

18. A system comprising
the riboregulator of claim 1, and
the trans-activating RNA (taRNA) of claim 16.

19. The system of claim 18, wherein the system is a cell.

20. The system of claim 19, wherein the cell is a prokaryotic cell.

21. The system of claim 18, wherein the system is a cell-free in vitro system.

22. The system of claim 18, wherein the riboregulator and the taRNA are hybridized to each other.

23. The system of claim 18, wherein the ratio of riboregulator to taRNA is less than 1, less than 0.5, or less than 0.1.

24. The system of claim 18, wherein the riboregulator is comprised in a first nucleic acid and the taRNA is comprised in a second nucleic acid.

25. The system of claim 24, wherein the first nucleic acid is a first plasmid and the second nucleic acid is a second plasmid.

26. The system of claim 24, wherein the first plasmid comprises a medium copy origin of replication and the second plasmid comprises a high copy origin of replication.

27. A nucleic acid comprising
the riboregulator of claim 1.

28. A host cell comprising the nucleic acid of claim 27.

29. A nucleic acid comprising
the trans-activating RNA (taRNA) of claim 16.

30. A host cell comprising the nucleic acid of claim 29.

31. A method of detecting presence of an RNA in a sample, comprising
combining a riboregulator of claim 1 with a sample, wherein the riboregulator comprises a toehold domain that is complementary to an endogenous RNA, and wherein the riboregulator comprises a coding domain that encodes a reporter protein, under conditions that allow translation of the coding domain in the presence of the endogenous RNA but not in the absence of the endogenous RNA, and
detecting the reporter protein as an indicator of the endogenous RNA.

32. A method of detecting presence of an RNA in a cell, comprising
introducing into the cell a riboregulator of claim 1, wherein the riboregulator comprises a toehold domain that is complementary to an endogenous RNA in the cell, and wherein the riboregulator comprises a coding domain that encodes a reporter protein, and
detecting the reporter protein as an indicator of the endogenous RNA.

33. The method of claim 31, wherein the reporter protein is green fluorescent protein (GFP).

34. The method of claim 31, wherein amount of reporter protein is an indicator of amount of endogenous RNA.

35. A method of controlling protein translation, comprising
combining a riboregulator of claim 1 with a taRNA of claim 16, wherein the riboregulator comprises a toehold domain that is complementary to the taRNA, and wherein the riboregulator comprises a coding domain that encodes a non-reporter protein, under conditions that allow translation of the coding domain in the presence of the taRNA but not in the absence of the taRNA.

\* \* \* \* \*

UNITED STATES PATENT AND TRADEMARK OFFICE
CERTIFICATE OF CORRECTION

| | |
|---|---|
| PATENT NO. | : 9,550,987 B2 |
| APPLICATION NO. | : 14/440917 |
| DATED | : January 24, 2017 |
| INVENTOR(S) | : Alexander A. Green et al. |

It is certified that error appears in the above-identified patent and that said Letters Patent is hereby corrected as shown below:

In the Specification

Column 1, Lines 17-21 (approx.), the paragraph under the heading FEDERALLY SPONSORED RESEARCH should be replaced with the following paragraph:

This invention was made with U.S. Government support under grant number HR0011-12-C0061 awarded by DARPA/DOD and grant number 1DP2OD007292 awarded by the National Institutes of Health. The Government has certain rights in the invention.

Signed and Sealed this
Fourth Day of April, 2017

Michelle K. Lee
*Director of the United States Patent and Trademark Office*

SEQUENCE LISTING

```
<160> NUMBER OF SEQ ID NOS: 102

<210> SEQ ID NO 1
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 1
gggaauugau auugugauua ugugaugauu guaaacagag gagauacaau augcacauaa      60
ucaaccuggc ggcagcgcaa aagaugcgua aa                                    92

<210> SEQ ID NO 2
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 2
gggacauacg gacucacgug uccguauguc aauacaauca ucacauaauc acaauaucaa      60
uuacu                                                                  65

<210> SEQ ID NO 3
<211> LENGTH: 92
<212> TYPE: RNA
<213> ORGANISM: Artificial Sequence
<220> FEATURE:
<223> OTHER INFORMATION: Synthetic polynucleotide
```

<400> SEQUENCE: 3
gggaauugau auuguucguu ucguaugauc uaagacagag gagauuagau augacgaaac    60
gaaaccuggc ggcagcgcaa aagaugcgua aa    92

<210> SEQ ID NO 4
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 4
gggacauacg gacucacgug uccguaugua acuuagauca uacgaaacga acaauaucaa    60
uuacu    65

<210> SEQ ID NO 5
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 5
gggaauugau auuguaguau guugaaguga uugaacagag gagacaauca augcaacaua    60
cuaaccuggc ggcagcgcaa aagaugcgua aa    92

<210> SEQ ID NO 6
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 6
gggacauacg gacucacgug uccguauguc agcaaucacu ucaacauacu acaauaucaa    60
uuacu    65

<210> SEQ ID NO 7
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 7
gggugaauga auuguaggcu uguuauaguu augaacagag gagacauaac augaacaagc    60
cuaaccuggc ggcagcgcaa aagaugcgua aa    92

<210> SEQ ID NO 8
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 8
gggaccgugg accgcaugag guccacggua aacauaacua uaacaagccu acaauucauu    60
caaac    65

<210> SEQ ID NO 9

```
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 9
ggguauaagu aaaucgcuug cuguaugucg uuaaacagag gagauaacga augacagcaa    60
gcaaccuggc ggcagcgcaa aagaugcgua aa                                 92

<210> SEQ ID NO 10
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 10
gggaugcccg uaguucauuc uacgggcaug aauaacgaca uacagcaagc gauuuacuua    60
uacua                                                               65

<210> SEQ ID NO 11
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 11
gggugaugga auaaggcugu guauaugaug uuagacagag gagauaacau augauacaca    60
gcaaccuggc ggcagcgcaa aagaugcgua aa                                 92

<210> SEQ ID NO 12
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 12
gggucaguuc cugagguacc aggaacugaa acuaacauca uauacacagc cuuauuccau    60
cacac                                                               65

<210> SEQ ID NO 13
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 13
ggguagauau ugaaugcugc uguuaugucg uuaaacagag gagauaacga augaacagca    60
gcaaccuggc ggcagcgcaa aagaugcgua aa                                 92

<210> SEQ ID NO 14
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 14
gggacgcgaa augcuauucc auuucgcgug acuaacgaca uaacagcagc auucaauauc    60
``` uaaac 65

<210> SEQ ID NO 15
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 15
gggauaagua gauaagauug uuagauggcu ucgaacagag gagacgaagc augcuaacaa    60
ucaaccuggc ggcagcgcaa aagaugcgua aa    92

<210> SEQ ID NO 16
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 16
gggucgugcg cucugagccg agcgcacgag aacgaagcca ucuaacaauc uuaucuacuu    60
aucac    65

<210> SEQ ID NO 17
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 17
gggaucacuu auugucgucu uuguaugucu guaaacagag gagauacaga augacaaaga    60
cgaaccuggc ggcagcgcaa aagaugcgua aa    92

<210> SEQ ID NO 18
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 18
gggacgucga uucaccgucg aaucgacgua gauacagaca uacaaagacg acaauaagug    60
auaga    65

<210> SEQ ID NO 19
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 19
gggacaaaga uuggucguuu cauuaccguu agaaacagag gagaucuaac augaaugaaa    60
cgaaccuggc ggcagcgcaa aagaugcgua aa    92

<210> SEQ ID NO 20
<211> LENGTH: 65
<212> TYPE: RNA
<213> ORGANISM: Artificial Sequence
<220> FEATURE:

<223> OTHER INFORMATION: Synthetic polynucleotide

<400> SEQUENCE: 20
gggacuccag gcggaauaac gccuggagua aaucuaacgg uaaugaaacg accaaucuuu    60
guaug    65

<210> SEQ ID NO 21
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 21
gggcgaaagu guauggcuga uaugauguag uuaaacagag gagauaacua augcauauca    60
gcaaccuggc ggcagcgcaa aagaugcgua aa    92

<210> SEQ ID NO 22
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 22
gggucgcacg guccgccua accgugcgag aauaacuaca ucauaucagc cauacacuuu    60
cgaac    65

<210> SEQ ID NO 23
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 23
ggguaagauu ugauggcuau uuguacgugu ucgaacagag gagacgaaca augacaaaua    60
gcaaccuggc ggcagcgcaa aagaugcgua aa    92

<210> SEQ ID NO 24
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 24
gggaccauuc gcccuacuug gcgaauggua agcgaacacg uacaaauagc caucaaaucu    60
uaacu    65

<210> SEQ ID NO 25
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 25
gggaauugga ugaaggcggu aaguaugauu uagacagag gagauacaau augacuuacc    60
gcaaccuggc ggcagcgcaa aagaugcgua aa    92

```
<210> SEQ ID NO 26
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 26
ggguccaguc uagacugacc uagacuggac aauacaauca uacuuaccgc cuucauccaa      60
uuacu                                                                 65

<210> SEQ ID NO 27
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 27
ggguagaauu ugauacuuga uuugauggcu ugaaacagag gagaucaagc augcaaauca      60
agaaccuggc ggcagcgcaa aagaugcgua aa                                   92

<210> SEQ ID NO 28
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 28
gggucuaaug cgaguaaagu cgcauuagaa uaucaagcca ucaaaucaag uaucaaauuc      60
uaaag                                                                 65

<210> SEQ ID NO 29
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 29
gggcguuaua cuuugucguu cugcgugucg uuaaacagag gagauaacga auggcagaac      60
gaaaccuggc ggcagcgcaa aagaugcgua aa                                   92

<210> SEQ ID NO 30
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 30
gggacugagg uaccucgaag uaccucagua gauaacgaca cgcagaacga caaaguauaa      60
cgaaa                                                                 65

<210> SEQ ID NO 31
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 31
```

```
ggguaagaau gauaaaggua aguagugagu ugaaacagag gagaucaacu auguacuuac    60
cuaaccuggc ggcagcgcaa aagaugcgua aa                                 92
```

<210> SEQ ID NO 32
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 32

```
gggccaugac uccuaauucg gagucaugga aaucaacuca cuacuuaccu uuaucauucu    60
uacuu                                                               65
```

<210> SEQ ID NO 33
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 33

```
gggcgauaaa gacugaggcu ggguaugguu agaaacagag gagaucuaac augacccagc    60
cuaaccuggc ggcagcgcaa aagaugcgua aa                                 92
```

<210> SEQ ID NO 34
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 34

```
gggccucgac guucgugaua acgucgaggc aaucuaacca uacccagccu cagucuuuau    60
cgcaa                                                               65
```

<210> SEQ ID NO 35
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 35

```
gggauagaug auugugcuua guuuaugauu cugaacagag gagacagaau augaaacuaa    60
gcaaccuggc ggcagcgcaa aagaugcgua aa                                 92
```

<210> SEQ ID NO 36
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 36

```
gggacauccu aaguugacuc uuaggaugua aacagaauca uaaacuaagc acaaucaucu    60
auaca                                                               65
```

<210> SEQ ID NO 37
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 37
gggauaauga ugaugaguau guugaagguug uaagacagag gagauuacac augcaacaua    60
cuaaccuggc ggcagcgcaa aagaugcgua aa    92

<210> SEQ ID NO 38
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 38
gggucgugug augcuaucuc aucacacgac aauuacaccu ucaacauacu caucaucauu    60
aucac    65

<210> SEQ ID NO 39
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 39
gggcguuaau cucuggcuug cuuuaugucu guaaacagag gagauacaga augaaagcaa    60
gcaaccuggc ggcagcgcaa aagaugcgua aa    92

<210> SEQ ID NO 40
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 40
gggucaugac ugggacacgc cagucaugag aauacagaca uaaagcaagc cagagauuaa    60
cgaag    65

<210> SEQ ID NO 41
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 41
ggguaaagau gaaacgcgug aaugauagua uugaacagag gagacaauac augcauucac    60
gcaaccuggc ggcagcgcaa aagaugcgua aa    92

<210> SEQ ID NO 42
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 42
gggucaccuc caggcacgac uggaggugaa uacaauacua ucauucacgc guuucaucuu    60
uacuu    65

<210> SEQ ID NO 43
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 43
gggcauuaag auuguacuug uaagaucgug ucgaacagag gagacgacac augcuuacaa    60
guaaccuggc ggcagcgcaa aagaugcgua aa                                 92

<210> SEQ ID NO 44
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 44
gggaccuagc ggagcgcagu ccgcuaggua acgacacga ucuuacaagu acaaucuuaa    60
ugaaa                                                               65

<210> SEQ ID NO 45
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 45
ggguaugaau ugaugucgau uguuaugucu ugagacagag gagaucaaga augaacaauc    60
gaaaccuggc ggcagcgcaa aagaugcgua aa                                 92

<210> SEQ ID NO 46
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 46
gggacccgac cgcguccugg cggucgggua aaucaagaca uaacaaucga caucaauuca    60
uacua                                                               65

<210> SEQ ID NO 47
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 47
ggguaaagau gagaacgcuu ugaaugaug ugaaacagag gagaucacau augucacaag    60
cgaaccuggc ggcagcgcaa aagaugcgua aa                                 92

<210> SEQ ID NO 48
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 48

```
ggucgggac acgggcauac gugucccgac aaucacauca uucacaagcg uucucaucuu    60
uacuu                                                               65
```

<210> SEQ ID NO 49
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 49

```
gggugauaga ugaaggcagg cguuauaguu uagaacagag gagacuaaac augaacgccu    60
gcaaccuggc ggcagcgcaa aagaugcgua aa                                 92
```

<210> SEQ ID NO 50
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 50

```
gggucguggg ccugccuaaa ggcccacgag aacuaaacua uaacgccugc cuucaucuau    60
caaac                                                               65
```

<210> SEQ ID NO 51
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 51

```
ggguaaguaa ugaagucuaa guguaucgug ucggacagag gagacgacac augacacuua    60
gaaaccuggc ggcagcgcaa aagaugcgua aa                                 92
```

<210> SEQ ID NO 52
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 52

```
gggacgaacu ugaucaaauu caaguucgua aacgacacga uacacuuaga cuucauuacu    60
uacau                                                               65
```

<210> SEQ ID NO 53
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 53

```
gggauagaau uagaaaugaa auagaugguu acgaacagag gagacguaac augcuauuuc    60
auaaccuggc ggcagcgcaa aagaugcgua aa                                 92
```

<210> SEQ ID NO 54
<211> LENGTH: 65
<212> TYPE: RNA

```
<213> ORGANISM: Artificial Sequence
<220> FEATURE:
<223> OTHER INFORMATION: Synthetic polynucleotide

<400> SEQUENCE: 54
gggucgcuug uacucuugcg uacaagcgaa agcguaacca ucuauuucau uucuaauucu    60
aucua                                                                65

<210> SEQ ID NO 55
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 55
gggauagaaa uugaucguua guuuauguug ccggacagag gagacggcaa augaaacuaa    60
cgaaccuggc ggcagcgcaa aagaugcgua aa                                  92

<210> SEQ ID NO 56
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 56
ggguaucuac ucgacuucgc gaguagauaa agcggcaaca uaaacuaacg aucaauuucu    60
auaac                                                                65

<210> SEQ ID NO 57
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 57
gggaguuuga auauggcgaa augaaugcuu ugaaacagag gagaucaaag augucauuuc    60
gcaaccuggc ggcagcgcaa aagaugcgua aa                                  92

<210> SEQ ID NO 58
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 58
gggacgagag cuccuagcag agcucucgua uaucaaagca uucauuucgc cauauucaaa    60
cuaac                                                                65

<210> SEQ ID NO 59
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 59
ggguaaagau gauaagaugu gaguaaggua guaaacagag gagauacuac augacucaca    60
ucaaccuggc ggcagcgcaa aagaugcgua aa                                  92
```

<210> SEQ ID NO 60
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 60
gggcacgacu agaaaccgau cuagucgugc aauacuaccu uacucacauc uuaucaucuu   60
uacuu                                                              65

<210> SEQ ID NO 61
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 61
gggaucuaaa uguauucguu cguuaugguu uugaacagag gagacaauac augaacgaac   60
gaaaccuggc ggcagcgcaa aagaugcgua aa                                92

<210> SEQ ID NO 62
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 62
gggcgucgcu guucggguaa acagcgacgg aacaauacca uaacgaacga auacauuuag   60
auacu                                                              65

<210> SEQ ID NO 63
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 63
gggucaauuu cguauuagua uguuaugguu cugaacagag gagacagaac augaacauac   60
uaaaccuggc ggcagcgcaa aagaugcgua aa                                92

<210> SEQ ID NO 64
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 64
gggacucggu cucuaugucg agaccgagua aacagaacca uaacauacua auacgaaauu   60
gaagc                                                              65

<210> SEQ ID NO 65
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 65
gggaauuugg aaguagagua guagauaguu augaacagag gagacauaac augcuacuac    60
ucaaccuggc ggcagcgcaa aagaugcgua aa                                 92

<210> SEQ ID NO 66
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 66
gggcagagcg gucuguuucg accgcucuga aacauaacua ucuacuacuc uacuuccaaa    60
uucua                                                               65

<210> SEQ ID NO 67
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 67
gggaguaaug augauauagu uugaauguag ugaaacagag gagaucacua augucaaacu    60
auaaccuggc ggcagcgcaa aagaugcgua aa                                 92

<210> SEQ ID NO 68
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 68
gggaccguca cccuacaucg ggugacggua aaucacuaca uucaaacuau aucaucauua    60
cuaac                                                               65

<210> SEQ ID NO 69
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 69
gggauaaugg agauggagua ggguaugauu guagacagag gagauacaau augcccuac     60 ucaaccuggc ggcagcgcaa aagaugcgua aa                                 92

<210> SEQ ID NO 70
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 70
gggccuagaa acuguacgaa guuucuaggc auuacaauca uacccuacuc caucccauu     60 aucuu                                                               65

<210> SEQ ID NO 71
<211> LENGTH: 92

```
<212> TYPE: RNA
<213> ORGANISM: Artificial Sequence
<220> FEATURE:
<223> OTHER INFORMATION: Synthetic polynucleotide

<400> SEQUENCE: 71
gggaugaaua uggacaguug aguagugaug ugaaacagag gagaucacau auguacucaa    60
cuaaccuggc ggcagcgcaa aagaugcgua aa                                 92

<210> SEQ ID NO 72
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 72
gggagucagg accgcaucag guccugacua aaucacauca cuacucaacu guccauauuc    60
aucuu                                                               65

<210> SEQ ID NO 73
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 73
gggauggaga uugauuauga uuggaugugc uuaaacagag gagauaagca augccaauca    60
uaaaccuggc ggcagcgcaa aagaugcgua aa                                 92

<210> SEQ ID NO 74
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 74
gggucgaccg cuccugcucg agcggucgac aauaagcaca uccaaucaua aucaaucucc    60
auaac                                                               65

<210> SEQ ID NO 75
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 75
gggaguaaga auugugauaa aguaaugugc gugaacagag gagacacgca auguacuuua    60
ucaaccuggc ggcagcgcaa aagaugcgua aa                                 92

<210> SEQ ID NO 76
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 76 ggguncacgga gcggauuugc gcuccgugag aacacgcaca uuacuuuauc acaauucuua    60
``` cuuca                                                                     65

<210> SEQ ID NO 77
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 77
gggucuuauc uuaucuaucu cguuuauccc ugcauacaga aacagaggag auaugcaaug      60
auaaacgaga accuggcggc agcgcaaaag augcguaaa                             99

<210> SEQ ID NO 78
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 78
gggacugacu auucugugca auagucagua aagcagggau aaacgagaua gauaagauaa      60
gauag                                                                  65

<210> SEQ ID NO 79
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 79
gggaguuuga uuacauuguc guuuaguuua gugauacaua aacagaggag auaucacaug      60
acuaaacgaa accuggcggc agcgcaaaag augcguaaa                             99

<210> SEQ ID NO 80
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 80
gggacagauc cacugaggcg uggaucugug aacacuaaac uaaacgacaa uguaaucaaa      60
cuaac                                                                  65

<210> SEQ ID NO 81
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 81
gggaucuauu acuacuuacc auugucuugc ucuauacaga aacagaggag auauagaaug      60
agacaaugga accuggcggc agcgcaaaag augcguaaa                             99

<210> SEQ ID NO 82
<211> LENGTH: 65
<212> TYPE: RNA
<213> ORGANISM: Artificial Sequence
<220> FEATURE:
<223> OTHER INFORMATION: Synthetic polynucleotide -continued

```
<400> SEQUENCE: 82
gggugauggg acauuccgau gucccaucaa uaagagcaag acaaugguaa guaguaauag      60
auaag                                                                 65

<210> SEQ ID NO 83
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 83
gggcgauuau ggauuagagc uccguuuacu gucauacaag aacagaggag auaugacaug      60
aaacggagca accuggcggc agcgcaaaag augcguaaa                            99

<210> SEQ ID NO 84
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 84
gggacgaauu cacccuaaug ugaauucgua aagacaguaa acggagcucu aauccauaau      60
cgaac                                                                 65

<210> SEQ ID NO 85
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 85
ggguauguaa uugauuuggc uucuguuagu uucauacaag aacagaggag auaugaaaug      60
aacagaagca accuggcggc agcgcaaaag augcguaaa                            99

<210> SEQ ID NO 86
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 86
ggguccauuc uaggugauac uagaauggag cagaaacuaa cagaagccaa aucaauuaca      60
uacua                                                                 65

<210> SEQ ID NO 87
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 87
gggcuuaauc uuaccuucgc uuguucuguu ccgauacaga aacagaggag auaucggaug      60
agaacaagca accuggcggc agcgcaaaag augcguaaa                            99

<210> SEQ ID NO 88
```

```
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 88
gggacaaucg ggacgacacu cccgauugug aacggaacag aacaagcgaa gguaagauua      60
aggua                                                                  65

<210> SEQ ID NO 89
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 89
gggucacuua aucauuuguc gucguuucua ucuauacaag aacagaggag auauagaaug      60
aaacgacgaa accuggcggc agcgcaaaag augcguaaa                             99

<210> SEQ ID NO 90
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 90
gggucgagua gacagagcug ucuacucgaa uaagauagaa acgacgacaa augauuaagu      60
gagaa                                                                  65

<210> SEQ ID NO 91
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 91
gggaccucua cuuacucuca cucuuacuuc ugcauaguag aacagaggag auaugcaaug      60
guaagaguga accuggcggc agcgcaaaag augcguaaa                             99

<210> SEQ ID NO 92
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 92
gggacugagc ugcuaucacg cagcucagua gagcagaagu aagagugaga guaaguagag      60
guaga                                                                  65

<210> SEQ ID NO 93
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 93
gggcuuacua cuuugacacc ugauucugac acgauaacag aacagaggag auaucguaug      60
```
agaaucagga accuggcggc agcgcaaaag augcguaaa                                 99

<210> SEQ ID NO 94
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 94
gggucaauua cccgugguag gguaauugaa agcgugucag aaucaggugu caaaguagua      60
aguag                                                                  65

<210> SEQ ID NO 95
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 95
gggaauggaa ugaaugaacu gcuugucuua uguauacaga aacagaggag auauacaaug      60
gacaagcaga accuggcggc agcgcaaaag augcguaaa                             99

<210> SEQ ID NO 96
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 96
gggcgaagug uccguaugag gacacuucga cgacauaaga caagcaguuc auucauucca      60
uuuag                                                                  65

<210> SEQ ID NO 97
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 97
gggcgaauag aaaugaaggc uagugucguu gucauacaga aacagaggag auaugacaug      60
gacacuagca accuggcggc agcgcaaaag augcguaaa                             99

<210> SEQ ID NO 98
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 98
gggacuccac gccgaccgug gcguggagua aagacaacga cacuagccuu cauuucuauu      60
cgauu                                                                  65

<210> SEQ ID NO 99
<211> LENGTH: 99
<212> TYPE: RNA
<213> ORGANISM: Artificial Sequence
<220> FEATURE:

```
<223> OTHER INFORMATION: Synthetic polynucleotide

<400> SEQUENCE: 99
gggcaauuuc guauauguuc gucuuugcug uucauacaag aacagaggag auaugaaaug      60
caaagacgaa accuggcggc agcgcaaaag augcguaaa                            99

<210> SEQ ID NO 100
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 100
gggcgacgau gccagguaug gcaucgucgg acgaacagca aagacgaaca uauacgaaau      60
ugaaa                                                                 65

<210> SEQ ID NO 101
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 101
gggauggaau ugagaugggc uuucgcgaga uugauacaga aacagaggag auaucaaaug      60
cgcgaaagca accuggcggc agcgcaaaag augcguaaa                            99

<210> SEQ ID NO 102
<211> LENGTH: 65
<212> TYPE: RNA
<213> ORGANISM: Artificial Sequence
<220> FEATURE:
<223> OTHER INFORMATION: Synthetic polynucleotide

<400> SEQUENCE: 102
gggugcggua guagguuccu acuaccgcaa uacaaucucg cgaaagccca ucucaauucc      60
auacu                                                                 65
```